United States Patent
Wong et al.

(10) Patent No.: US 11,046,731 B2
(45) Date of Patent: Jun. 29, 2021

(54) ZINC-BINDER BASED EBNA1-SPECIFIC COMPOUNDS

(71) Applicant: Hong Kong Baptist University, Hong Kong (HK)

(72) Inventors: Ka Leung Wong, Hong Kong (HK); Nai Ki Mak, Hong Kong (HK); Lijun Jiang, Hong Kong (HK)

(73) Assignee: Hong Kong Baptist University, Hong Kong (CN)

( * ) Notice: Subject to any disclaimer, the term of this patent is extended or adjusted under 35 U.S.C. 154(b) by 80 days.

(21) Appl. No.: 16/249,987

(22) Filed: Jan. 17, 2019

(65) Prior Publication Data

US 2019/0382444 A1 Dec. 19, 2019

Related U.S. Application Data

(60) Provisional application No. 62/619,093, filed on Jan. 18, 2018, provisional application No. 62/652,304, filed on Apr. 3, 2018, provisional application No. 62/682,161, filed on Jun. 7, 2018.

(51) Int. Cl.

| | |
|---|---|
| *A61K 38/08* | (2019.01) |
| *A61K 38/10* | (2006.01) |
| *A61K 47/54* | (2017.01) |
| *C07K 7/02* | (2006.01) |
| *C07K 7/06* | (2006.01) |
| *C07K 7/08* | (2006.01) |
| *G01N 33/58* | (2006.01) |
| *A61P 35/00* | (2006.01) |
| *A61K 47/55* | (2017.01) |
| *A61K 38/00* | (2006.01) |

(52) U.S. Cl.
CPC ............... *C07K 7/06* (2013.01); *A61K 38/08* (2013.01); *A61K 38/10* (2013.01); *A61K 47/545* (2017.08); *A61K 47/55* (2017.08); *A61K 47/558* (2017.08); *A61P 35/00* (2018.01); *C07K 7/02* (2013.01); *C07K 7/08* (2013.01); *G01N 33/582* (2013.01); *A61K 38/00* (2013.01); *G01N 2333/05* (2013.01)

(58) Field of Classification Search
CPC ...... A61K 38/08; A61K 38/10; A61K 47/545; A61K 47/55; A61K 47/558; C07K 7/02; C07K 7/06; G01N 33/582; G01N 2333/05
See application file for complete search history.

(56) References Cited

U.S. PATENT DOCUMENTS

2007/0208007 A1* 9/2007 Saitou .................. C07D 405/14
514/218
2017/0304284 A1 10/2017 Wong et al.

FOREIGN PATENT DOCUMENTS

WO  WO-2007002587 A2 *  1/2007  ......... A61K 31/7076

OTHER PUBLICATIONS

Jiang et al.; EBNA1-specific luminescent small molecules for the imaging and inhibition of latent EBV-infected tumor cells; Chemical Communications; Jun. 21, 2014; p. 6517-6519 vol. 50, Issue 49; The Royal Society of Chemistry.

(Continued)

*Primary Examiner* — Jeffrey E. Russel
(74) *Attorney, Agent, or Firm* — Spruson & Ferguson (Hong Kong) Limited

(57) ABSTRACT

The present disclosure relates to compounds useful in the treatment, imaging, and/or diagnosis of Epstein-Barr virus (EBV)-positive cells, such as cancer.

20 Claims, 81 Drawing Sheets
Specification includes a Sequence Listing.

(56) References Cited

OTHER PUBLICATIONS

Jiang et al.; EBNA1-targeted probe for the imaging and growth inhibition of tumours associated with the Epstein-Barr virus; Nature Biomedical Engineering; Mar. 13, 2017; p. 1-10; vol. 1, Issue 4; Macmillan Publishers Limited.

* cited by examiner

L5-NME

Zn²⁺-L5-NME

L5-NME (calculated structure)
ZTF (crystal structure)

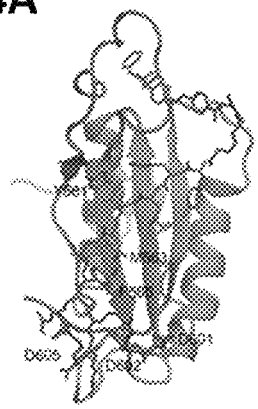
FIG. 14A L5P4-EBNA1 Simulation #1
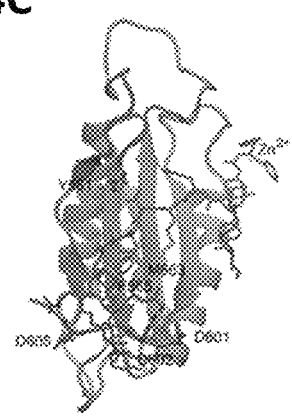
FIG. 14C Zn²⁺-L5P4-EBNA1 Simulation #1
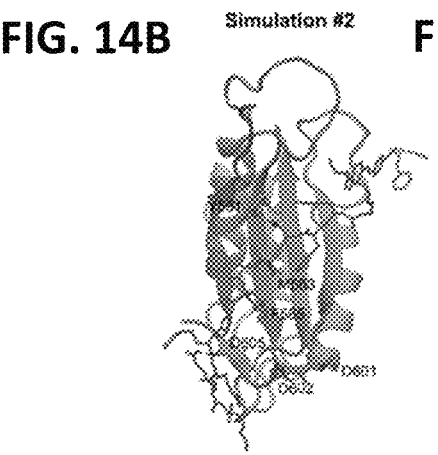
FIG. 14B Simulation #2
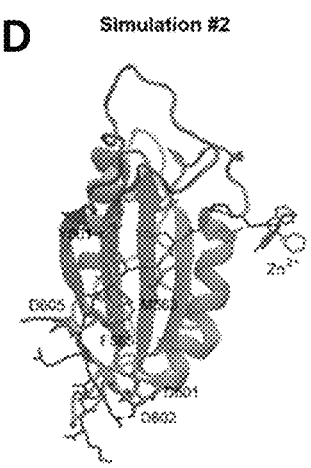
FIG. 14D Simulation #2

ZINC-BINDER BASED EBNA1-SPECIFIC COMPOUNDS

CROSS-REFERENCE TO RELATED APPLICATIONS

This application claims priority from U.S. Provisional Patent Application No. 62/619,093, filed on Jan. 18, 2018, U.S. Provisional Patent Application No. 62/652,304 filed on Apr. 3, 2018, and U.S. Provisional Patent Application No. 62/682,161, filed on Jun. 7, 2018, the disclosures of which are hereby incorporated by reference in their entirety.

REFERENCE TO SEQUENCE LISTING

The specification further incorporates by reference the Substitute Sequence Listing submitted herewith via EFS on Aug. 10, 2020. The Sequence Listing text file, identified as Sequence_Listing_034590-000004.txt, is 2,010 bytes and was created on Jun. 23, 2020. The Substitute Sequence Listing, electronically filed herewith, does not extend beyond the scope of the specification and thus does not contain new matter.

FIELD OF INVENTION

The present disclosure generally relates to compounds useful as therapeutic, imaging, and/or diagnostic agents. More particularly, the present disclosure relates to compounds of binding zinc and EBNA1 with responsive imaging properties and robust inhibition of EBNA1 for the treatment of EBV-positive cells, such as cancers.

BACKGROUND

Epstein-Barr virus (EBV) infects the majority of the human population worldwide and can establish lifelong latent infection in hosts. The association between latent EBV infection and the development of certain lymphomas and epithelial malignancies is well known. EBV encoded Nuclear Antigen 1 (EBNA1) is a highly restricted gene that is expressed in the latent phase of EBV infection and is the only protein that expressed in all EBV latently-infected cells, EBV encoded Nuclear Antigen 1 (EBNA1), making it a promising and effective target for the treatment of EBV-positive cancers.

Despite its importance, neither the precise role(s) of EBNA1 in EBV latent infection is well understood, nor have any therapies targeting EBNA1 for the treatment of EBV-positive cancers have been approved. This emphasizes that continuous efforts are needed to develop potent EBNA1 inhibitors. In the past few years, several strategies have been used to inhibit EBNA1 or EBNA1-dependent cellular functions, including the inhibiting the expression of EBNA1, EBNA1-DNA binding activities, EBNA1-RNA interactions, and EBNA1 homo-dimerization. Although these inhibitors were shown to inhibit their targets in vitro and in vivo, there were problems with them, such as lack of specificity, poor cellular permeability and poorly understood mechanisms of action. These problems stemmed, in part, from the fact that the inhibitors were identified using screening-based approaches and failed to show the direct binding to EBNA1, which largely limited their application.

Furthermore, due to the non-fluorescent nature of conventional EBNA1 inhibitors, this presents obstacles to track and study inhibitor distribution and their cellular functions. Fluorescence imaging is useful for sensing biomolecules in living systems due to its unique potential advantages, such as excellent sensitivity and selectivity, high spatial and temporal resolution, simplicity and implementation, facile visualization, and real-time analysis of intracellular dynamics and biomolecular localization at subcellular levels.

There thus exists a need for improved EBNA1 inhibitors that address one or more of the aforementioned needs.

SUMMARY

The present disclosure relates to zinc-binding EBNA1-specific probes for the detection and regulation of EBNA1 and which are useful in the treatment of EBV-positive cancer.

In a first aspect, provided herein is a compound of Formula I:

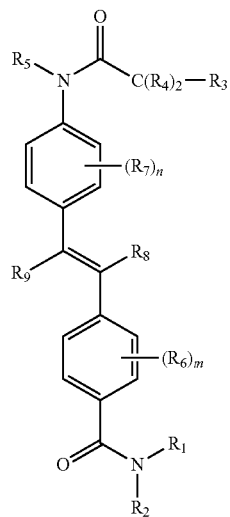

or a pharmaceutically acceptable salt thereof, wherein
m is a whole number selected from 0-4;
n is a whole number selected from 0-4;
p is a whole number selected from 0-4;
X is $H_2$, S, or O;
each instance of R is independently H or alkyl;
$R_1$ is selected from the group consisting of SEQ ID NO:1, SEQ ID NO:2, SEQ ID NO:3, SEQ ID NO:4, SEQ ID NO:5, and SEQ ID NO:6;
$R_2$ is H or alkyl;
$R_3$ is selected from the group consisting of:

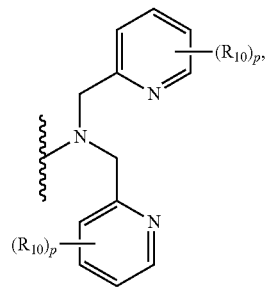

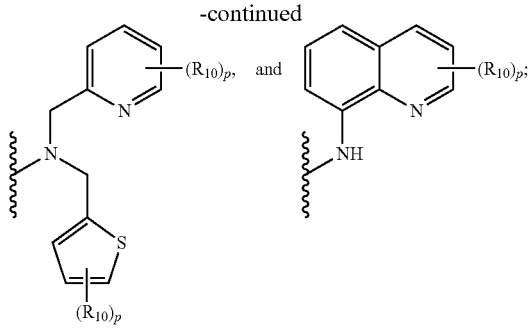

each instance of $R_4$ is independently H or alkyl;

$R_5$ is H or alkyl;

each instance of $R_6$ is independently H, alkyl, alkene, alkyne, cycloalkyl, aryl, heteroaryl, halide, nitrile, nitro, OR, or $NR_2$;

each instance of $R_7$ is independently H, alkyl, alkene, alkyne, cycloalkyl, aryl, heteroaryl, halide, nitrile, nitro, OR, or $NR_2$;

each of $R_8$ and $R_9$ is independently H or alkyl; and each instance of $R_{10}$ is independently H, alkyl, alkene, alkyne, cycloalkyl, aryl, heteroaryl, halide, nitrile, nitro, OR, or $NR_2$.

In a first embodiment of the first aspect, provided herein is the compound of the first aspect, wherein each of $R_6$, $R_7$, and $R_{10}$ for each occurrence is independently selected from the group consisting of H, alkyl, halide, nitrile, and nitro.

In a second embodiment of the first aspect, provided herein is the compound of the first aspect, wherein each of $R_2$ and $R_5$ is H.

In a third embodiment of the first aspect, provided herein is the compound of the first aspect, wherein each of $R_4$, $R_8$, and $R_9$ is H.

In a fourth embodiment of the first aspect, provided herein is the compound of the first aspect, wherein X is O and $R_3$ is:

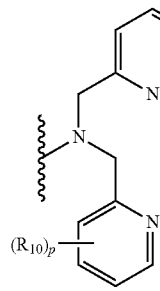
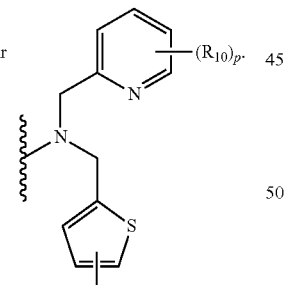

In a fifth embodiment of the first aspect, provided herein is the compound of the fourth embodiment of the first aspect, wherein $R_6$, $R_7$, and $R_{10}$ for each occurrence is independently selected from the group consisting of H, alkyl, halide, nitrile, and nitro.

In a sixth embodiment of the first aspect, provided herein is the compound of the fifth embodiment of the first aspect, wherein each of $R_4$, $R_8$, and $R_9$ is H.

In a seventh embodiment of the first aspect, provided herein is the compound of the first aspect, wherein the compound has Formula II:

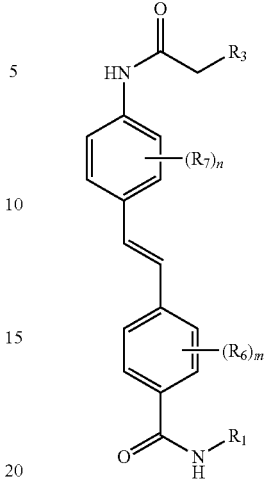

or a pharmaceutically acceptable salt thereof, wherein m is a whole number selected from 0-4;

n is a whole number selected from 0-4;

p is a whole number selected from 0-4;

$R_1$ is selected from the group consisting of SEQ ID NO:1, SEQ ID NO:2, SEQ ID NO:3, SEQ ID NO:4, SEQ ID NO:5, and SEQ ID NO:6;

$R_3$ is selected from the group consisting of:

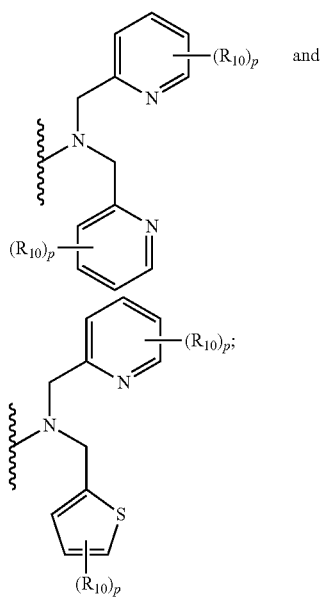

each instance of $R_6$ is independently H, alkyl, alkene, alkyne, cycloalkyl, aryl, heteroaryl, halide, nitrile, nitro, OR, or $NR_2$;

each instance of $R_7$ is independently H, alkyl, alkene, alkyne, cycloalkyl, aryl, heteroaryl, halide, nitrile, nitro, OR, or $NR_2$;

each of $R_8$ and $R_9$ is independently H or alkyl; and each instance of $R_{10}$ is independently H, alkyl, alkene, alkyne, cycloalkyl, aryl, heteroaryl, halide, nitrile, nitro, OR, or $NR_2$.

In an eighth embodiment of the first aspect, provided herein is the compound of the first aspect, wherein the compound has the Formula III:

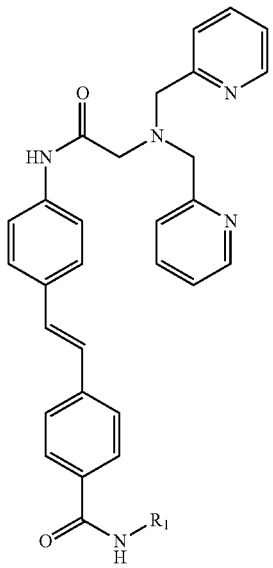

III or a pharmaceutically acceptable salt thereof, wherein $R_1$ is selected from the group consisting of SEQ ID NO:1, SEQ ID NO:2, SEQ ID NO:3, SEQ ID NO:4, SEQ ID NO:5, and SEQ ID NO:6.

In a ninth embodiment of the first aspect, provided herein is the compound of the first aspect, wherein X is $H_2$ and $R_3$ is:

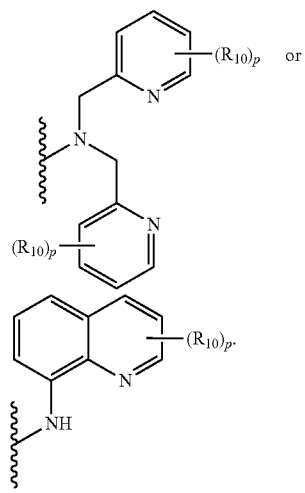

In a tenth embodiment of the first aspect, provided herein is the compound of the ninth embodiment of the first aspect, wherein each of $R_6$, $R_7$, and $R_{10}$ for each occurrence is independently selected from the group consisting of H, alkyl, halide, nitrile, and nitro.

In an eleventh embodiment of the first aspect, provided herein is the compound of the tenth embodiment of the first aspect, wherein each of $R_2$ and $R_5$ is H.

In a twelfth embodiment of the first aspect, provided herein is the compound of the eleventh embodiment of the first aspect, wherein each of $R_4$, $R_8$, and $R_9$ is H.

In a thirteenth embodiment of the first aspect, provided herein is the compound of the twelfth embodiment of the first aspect, wherein each of $R_6$, $R_7$, and $R_{10}$ is H.

In a second aspect, provided herein is a method of treating an Epstein-Barr virus (EBV)-positive cell in a patient in need thereof comprising administering a therapeutically effective amount of a compound of the first aspect to the patient.

In a first embodiment of the second aspect, provided herein is the method of the second aspect, wherein the EBV-positive cell is a cancerous cell.

In a second embodiment of the second aspect, provided herein is the method of the first method of the second aspect, wherein the cancerous cell is Burkitt's lymphoma, non-Hodgkin's lymphoma, Hodgkin's disease, T-cell lymphoma, B-cell lymphoma, transplant-associated lymphoproliferative disorders, nasopharyngeal carcinoma, gastric adenocarcinoma, parotid carcinoma, or leiomyosarcoma.

In a third embodiment of the second aspect, provided herein is the method of the second aspect, wherein the compound has the Formula III:

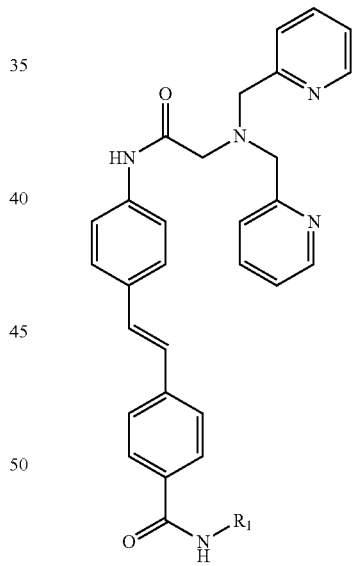

III or a pharmaceutically acceptable salt thereof, wherein $R_1$ is selected from the group consisting of SEQ ID NO:1, SEQ ID NO:2, SEQ ID NO:3, SEQ ID NO:4, SEQ ID NO:5, and SEQ ID NO:6.

In a third aspect, provided herein is a method of imaging an EBV-positive cell comprising the step of contacting the EBV-positive cell with a compound of the first aspect and measuring the fluorescence of the compound.

In a first embodiment of the third aspect, provided herein is the method of the third aspect, wherein the compound has the Formula III:

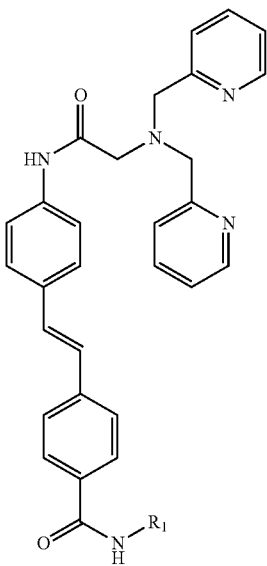

or a pharmaceutically acceptable salt thereof, wherein $R_1$ is selected from the group consisting of SEQ ID NO:1, SEQ ID NO:2, SEQ ID NO:3, SEQ ID NO:4, SEQ ID NO:5, and SEQ ID NO:6.

BRIEF DESCRIPTION OF DRAWINGS

The above and other objects and features of the present invention will become apparent from the following description of the invention, when taken in conjunction with the accompanying drawings, in which.

RMSD of main-chain atoms from $Zn^{2+}$-$ZRL_5P_4$ ligand (YFMVF, SEQ ID NO:2) with regard to the initial and end structure. (E) The salt-bridging between RrRK motif and acid residues in the C-terminus of EBNA1 DBD. (F) The hydrophobic interactions between YFMVF motif and the dimeric interface of EBNA1 DBD.

FIG. 13(A-F) shows 200 ns NPT simulation of $Zn^{2+}$-$ZRL_5P_4$-EBNA1 complex model (#2). (A) RMSF of the putative EBNA1 DBD monomer. (B) RMSF of $Zn^{2+}$-$ZRL_5P_4$. (C) RMSD of main-chain atoms from EBNA1 DBD with regard to (w.r.t) the initial and end structure. (D) RMSD of main-chain atoms from $Zn^{2+}$-$ZRL_5P_4$ (YFMVF, SEQ ID NO:2) with regard to the initial and end structure. (E) The salt-bridging between RrRK motif and acid residues in the C-terminus of EBNA1 DBD. (F) The hydrophobic interactions between YFMVF motif and the dimeric interface of EBNA1 DBD.

FIG. 14(A-D) shows the putative structure of $ZRL_5P_4$-EBNA1 and $Zn^{2+}$-$ZRL_5P_4$-EBNA1 complex. (A, B) Representative conformation of $ZRL_5P_4$-EBNA1 complex resulted from two independent MD simulations. The calculated GB and PB values represented their binding free energy. (C, D) Representative conformation of $Zn^{2+}$-$ZRL_5P_4$-EBNA1 complex resulted from two independent MD simulations. The calculated GB and PB values represented their binding free energy.

FIG. 15(A-B) shows $^1H$ NMR spectra of compound 5 in the presence of $Zn^{2+}$ in $CD_3CN$ (A) and DMSO-$d_6$ (B). The binding of the carbonyl oxygen to $Zn^{2+}$ in $CD_3CN$ blocks the resonance structure of the amide group and shifts the proton 8 upfield; and the binding of the amide nitrogen to $Zn^{2+}$ in DMSO-$d_6$ functions as the electron-withdrawing group to shift the proton 8 downfield.

Figure 16:
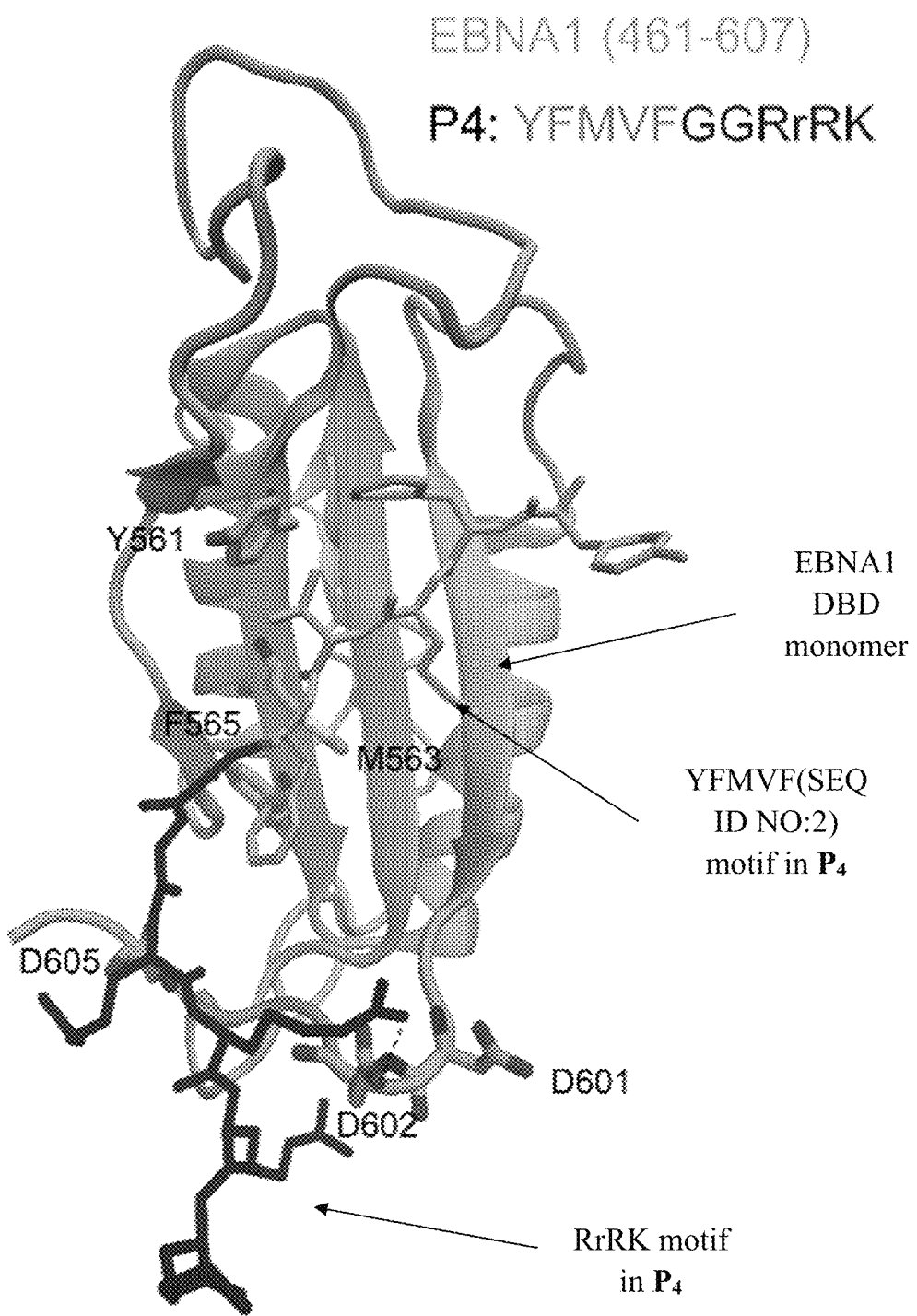
Figure 17A:
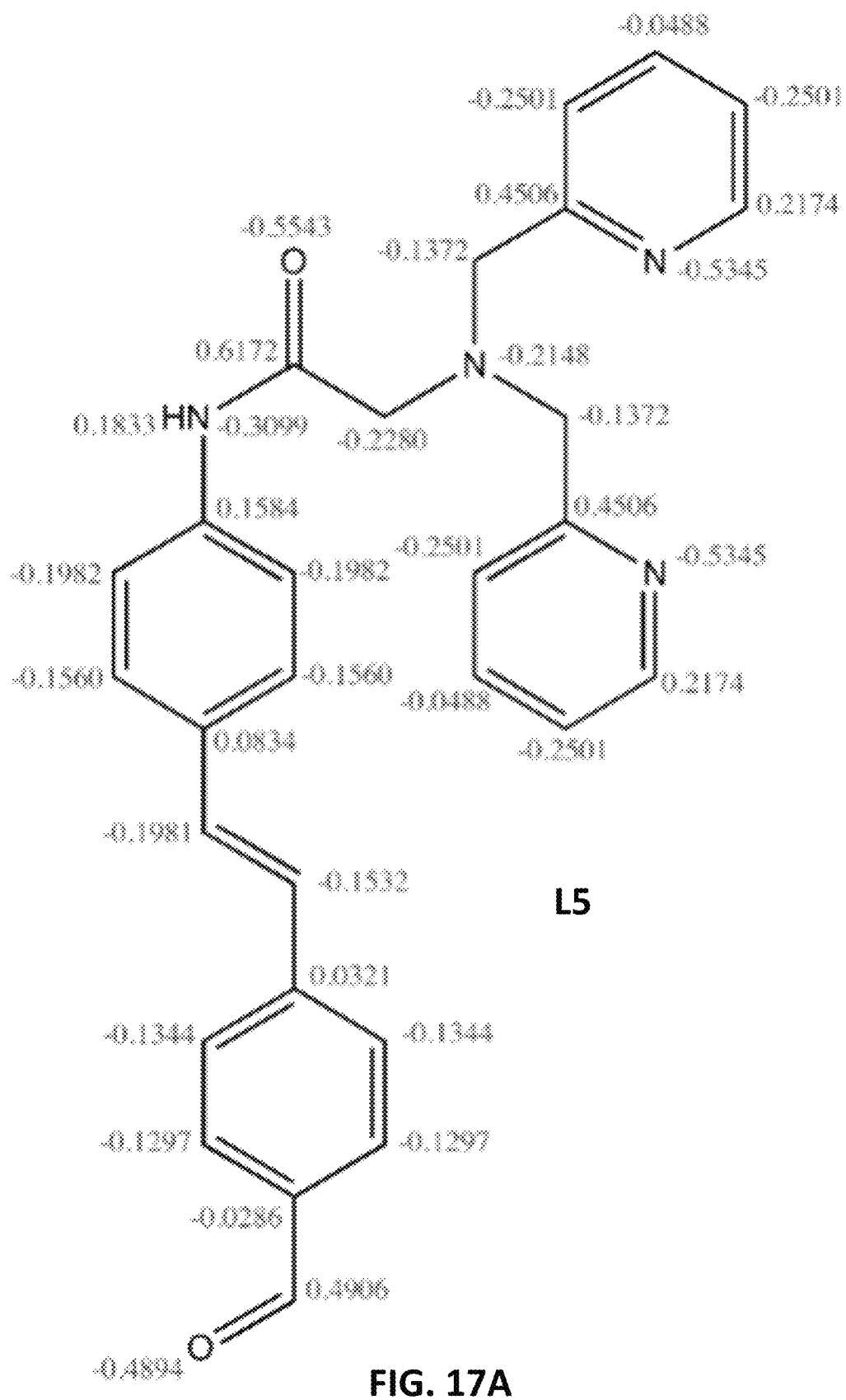
Figure 17B:
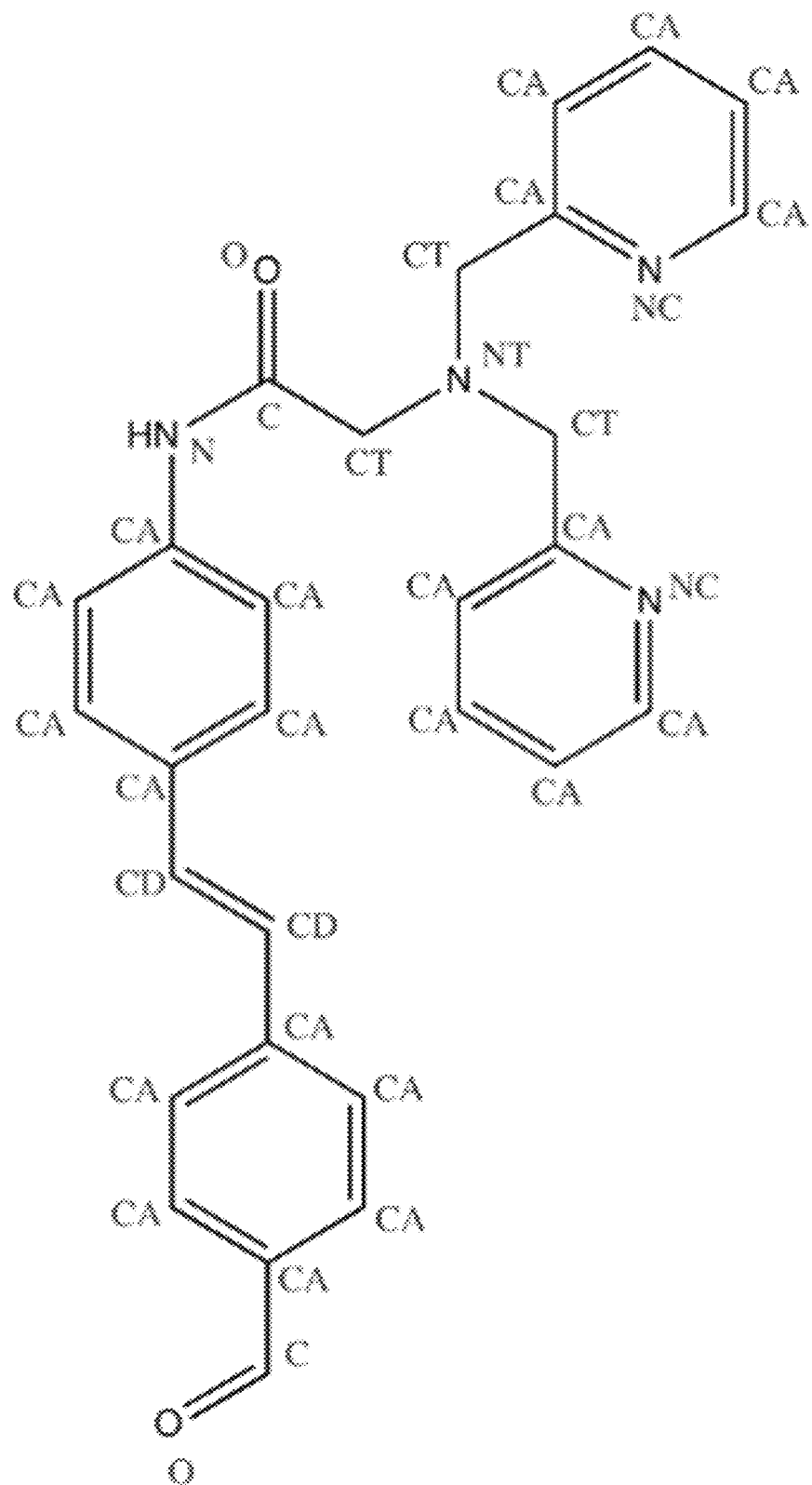
Figure 17C:
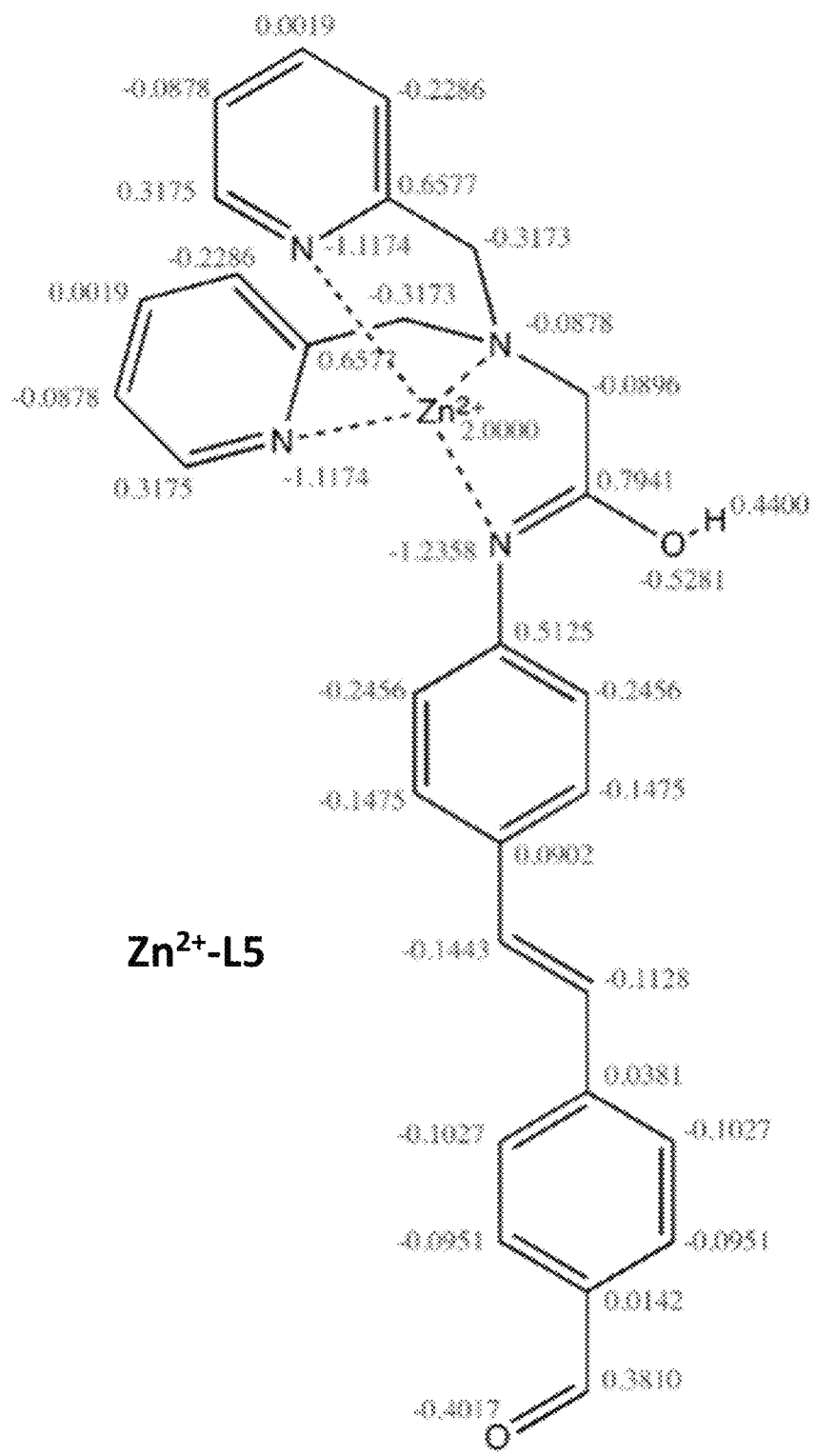
Figure 17D:
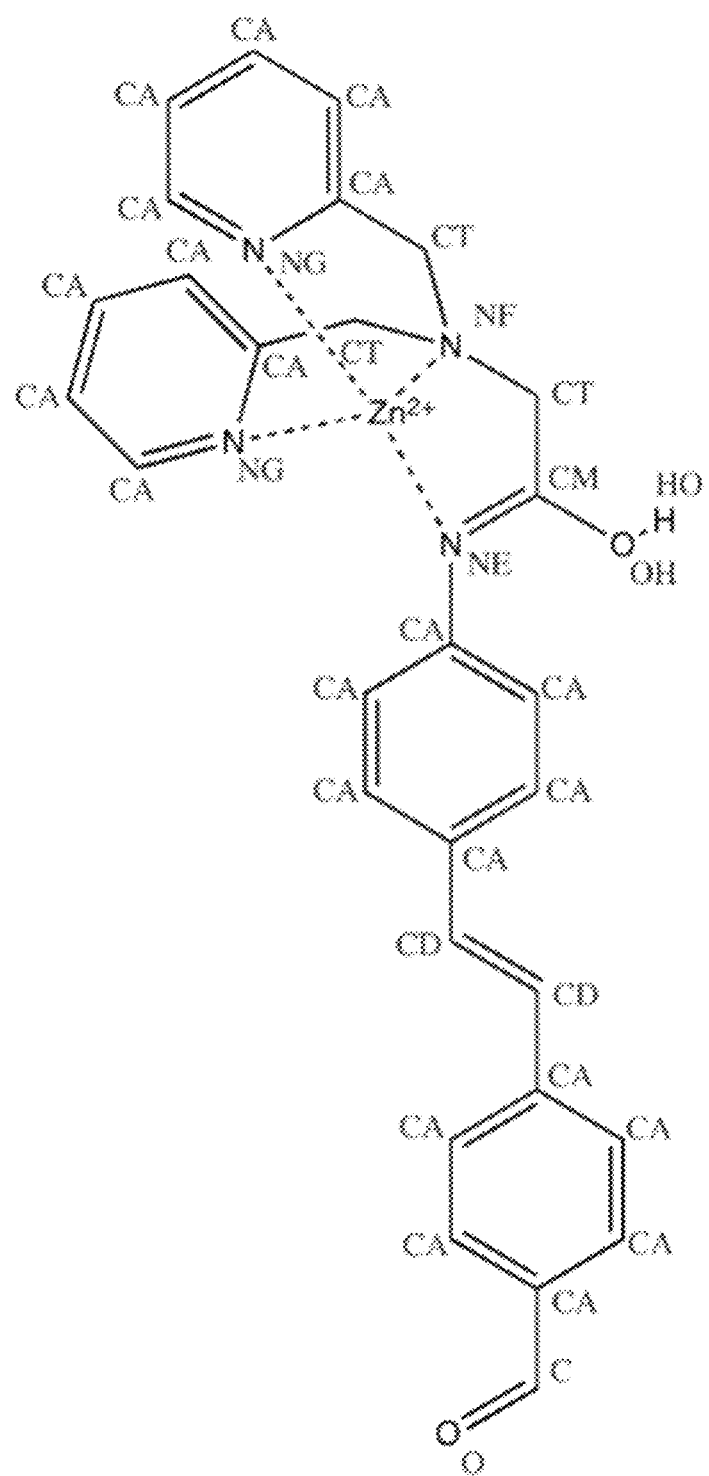

FIG. 16 shows the representative $P_4$-EBNA1 complex structure after 500 ns MD simulations. $P_4$-EBNA1 DBD binding was mediated by both hydrophobic interactions from YFMVF (SEQ ID NO:2) to dimeric interface of EBNA1 DBD and salt bridges from RrRK motif to C-terminus of EBNA1 DBD.

FIG. 17(A-D) shows the partial charge (A, C) and AMBER atom types (B, D) of $ZRL_5$ (A, B) and $Zn^{2+}$-$ZRL_5$ (C, D) for MD simulations.

FIG. 18(A-I) shows $ZRL_5P_4$ inhibited EBNA1 dimerization (A-B) and transactivation by EBNA1 (C-D). MBS-cross-linked, full-length EBNA1 dimerization in the absence/presence of $Zn^{2+}$ by $L_2P_4$/$ZRL_5P_4$ (control in buffer) (A) and their calculated EBNA1 monomer/dimer band intensity (B). EDTA, TPEN, $ZRL_5P_4$ and $L_2P_4$ differentially affect the ability of EBNA1 to transactivate oriP-Cp-luciferase in EBV-positive C666-1 (C) and NPC43 (D) cells. Dashed line in (C) and (D) was plotted for a better comparison of transactivation between different compounds. Cytotoxicity assays of $ZRL_5P_2$, $ZRL_5P_4$, and $ZRL_5P_6$ in EBV-negative HK-1 cells (E) and HONE-1 cells (F) (conc. 1, 5, 10, 20, 50, 100 μM) and EBV-positive NPC43 cells (G), C666-1 cells (H), and Raji cells (I) (conc. 1, 3, 5, 10, 15, 20 μM) were measured. Cells were treated with different probes and then incubated for 5 days to test their cytotoxicity (half of the medium was replaced every 4 days with fresh medium containing the appropriate concentration of the probes).

FIG. 19(A-C) shows two-photon fluorescence imaging of $ZRL_5P_2$, $ZRL_5P_4$, and $ZRL_5P_6$ in living EBV-positive (A) NPC43 cells and (B) C666-1 cells, and EBV-negative (C) HONE-1 cells. $ZRL_5P_n$, signal emitted from the respective EBNA1 probe. DRAQ5 is a fluorescent dye used to label the cell nuclei of the living cells as indicated.

FIG. 20(A-F) shows in vivo anti-tumor activity of $ZRL_5P_2$, $ZRL_5P_4$, and $ZRL_5P_6$ in EBV-positive C666-1 mouse xenograft model. Mice were treated twice weekly with 4 μg/injection of the probes for 18 days. Throughout the treatment period, (A) tumor volumes and (B) body weights were measured. At the experimental endpoint, tumors were excised. (C) Tumor weights and (D) representative photographs of tumors. Data are expressed as the means±SEM. *$P<0.05$; $P<0.005$; *$P<0.005$ vs. vehicle. Scale bars: 10 mm. (E) Representative images of tumor sections derived from the above in vivo animal study. Cell necrosis (acellular areas indicated by *) was observed in the tumor nodules treated with $ZRL_5P_4$ and $ZRL_5P_6$. H&E, hematoxylin and eosin. T, adjacent area with tumor cells. Magnification, 40×. Scale bar, 20 μm. (F) In vitro emission spectra (from confocal microscopy) of $ZRL_5P_2$, $ZRL_5P_4$, and $ZRL_5P_6$ in the nucleus of EBV-positive NPC43 and -negative HONE-1 cells. Emission intensity was much greater for $ZRL_5P_4$ and $ZRL_5P_6$ in EBV-positive cells.

FIG. 21(A-D) shows expression analyses of EBV lytic genes and proteins in response to the EBNA1 probes. (A) IHC analysis of lytic proteins BZLF1 (Zta) and BMRF1 in the transplanted C666-1-derived tumor tissues as described in FIG. 20. Representative results are shown. Nuclear staining of Zta and BMRF1 are observed in the necrotic tumor regions in response to $ZRL_5P_2$, $ZRL_5P_4$ and $ZRL_5P_6$. Magnification, 400×. Scale bar, 2 μm. (B, C) Gene expression analysis of EBV lytic genes, BRLF1 (Rta) and BMRF1, in C666-1 and NPC43 cells cultured with or without 10 μM $ZRL_5P_2$ and $ZRL_5P_4$ for 3 (C666-1 cells) or 7 (NPC43 cells) days. The gene expression was analyzed by qRT-PCR. Fold change of the relative gene expression after each treatment was compared with the solvent control (DMSO) and compared between the two treatments. (D) Protein expression analysis of early (Rta and BMRF1) and late (gp350/220) EBV lytic proteins in EBV-positive NPC43 cells cultured with or without 10 μM $ZRL_5P_2$ and $ZRL_5P_4$ for 7 (NPC43 cells) days. The protein expression was detected with Western blot, and ß-actin serves as the loading control.

FIG. 22(A-B) shows production of EBV particle in response to $ZRL_5P_4$. The HONE-1-EBV cell line, which expresses GFP to indicate the presence of the EBV genome, was used. This cell line was treated with 10 μM $ZRL_5P_2$ or $ZRL_5P_4$ for 4 days, and the viral particles released in the culture medium was detected by the Raji cell assay. The culture medium was added to Raji cells for 3 days, and GFP expression reflects the re-infection by the HONE-1-released EBV particles. (A) Relative average viral titer in response to $ZRL_5P_2$ or $ZRL_5P_4$ was compared with the solvent control (DMSO). The Raji cell assay was performed in triplicates for each treatment. **, $P<0.01$, statistically significant difference. (B) Representative results are shown. The GFP signal was detected by UV light exposure, and the cell morphology was captured by phase-contrast light microscopy and the bright field image was merged with the GFP image. Magnification, 40×. Scale bar, 20 μm.

FIG. 23(A-E) shows effect of $ZRL_5P_2$/$ZRL_5P_4$/$ZRL_5P_6$ on the weights of vital organs. Weights of the (A) heart, (B) lung, (C) liver, (D) kidney and (E) spleen were normalized to mouse body weights at the experimental endpoint. Data are expressed as the mean±SEM. *$P<0.05$; $P<0.005$; *$P<0.005$ vs. control. Treatment with $ZRL_5P_2$, $ZRL_5P_4$, and $ZRL_5P_6$ did not cause any significant changes in organ weights when compared to the control.

FIG. 24(A-D) shows in vivo anti-tumor activity of $ZRL_5P_2$, $ZRL_5P_4$, and $ZRL_5P_6$ in EBV-negative HeLa xenografts. Mice were treated every three days with 4 μg/injection of the probes for 19 days. Throughput the treatment period, (A) tumor volumes and (B) body weights were measured. At the experimental endpoint, tumors were excised and (C) tumor weights and (D) representative photographs of tumors. Data are expressed as means±SEM. *P<0.05; P<0.005; *P<0.005 vs. control. Scale bar: 10 mm. There was no significant difference in both the tumor volume and tumor weight between the control mice and those treated with probes. Also, treatment with $ZRL_5P_2$, $ZRL_5P_4$, and $ZRL_5P_6$ did not cause any significant changes in body weights compared to the control.

DETAILED DESCRIPTION

The present disclosure is not to be limited in scope by any of the specific embodiments described herein. The following embodiments are presented for exemplification only.

Those skilled in the art will appreciate that the methods and compositions described herein are susceptible to variations and modifications other than those specifically described.

The present disclosure includes all such variations and modifications. The present disclosure also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the present invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

As used herein, "halo", "halogen", or halide refer to fluorine, chlorine, bromine, and iodine.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl,-pentyl), hexyl groups, and the like. In various embodiments, an alkyl group can have 1 to 40 carbon atoms (i.e., C1-40 alkyl group), for example, 1-30 carbon atoms (i.e., C1-30 alkyl group). In some embodiments, an alkyl group can have 1 to 6 carbon atoms, and can be referred to as a "lower alkyl group." Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "cycloalkyl" by itself or as part of another substituent means, unless otherwise stated, a monocyclic hydrocarbon having between 3-12 carbon atoms in the ring system and includes hydrogen, straight chain, branched chain, and/or cyclic substituents. Exemplary cycloalkyls include cyclopropyl, cyclobutyl, cyclopentyl, cyclohexyl, cycloheptyl, and the like.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In some embodiments, alkenyl groups can be substituted as described herein. An alkenyl group is generally not substituted with another alkenyl group, an alkyl group, or an alkynyl group.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S-0 bonds. However, one or more N or S atoms in a heteroaryl group can be oxidized (e.g., pyridine Noxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), SiH2, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuryl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The compounds described herein may include one or more groups that can exist as stereoisomers. All such stereoisomer isomers are contemplated by the present disclosure. In instances in which stereochemistry is indicated (for example E/Z double bond isomers), it is understood that for the sake of simplicity that only one stereoisomer is depicted. However, all stereoisomers and mixtures thereof are contemplated by the present disclosure.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "EBV-positive cancer cells" refers to those cancers and cancer cells which express, e.g., in a latent form, EBV. Examples of such cancers include, but are not limited to, nasopharyngeal carcinoma, Burkitt's lymphoma, Hodgkin's Disease, T-cell lymphoma, B-cell lymphoma, transplant-associated lymphoproliferative disorders, gastric carcinoma, parotid carcinoma, breast carcinoma, leiomyosarcoma. In certain embodiments EBV-positive cancers are cancers wherein greater than about 30%, greater than about 40%, greater than about 50%, greater than about 60%, greater than about 70%, or greater than about 80% contain the EBV virus. The most preferred cancer and/or cancer cell for treatment with the method of the invention is nasopharyngeal carcinoma (NPC).

The term a "therapeutically effective amount" of an agent as used herein is that amount sufficient to effect beneficial or desired results, including clinical results, and, as such, a "therapeutically effective amount" depends upon the context in which it is being applied. For example, in the context of administering a compound that inhibits EBV-positive cancer cell proliferation, an effective amount of a compound is, for example, an amount sufficient to achieve such an inhibition as compared to the response obtained without administration of the agent.

The term "pharmaceutically acceptable salt" or "salt" refers to a salt of one or more compounds. Suitable pharmaceutically acceptable salts of compounds include acid addition salts which may, for example, be formed by mixing a solution of the compound with a solution of a pharmaceutically acceptable acid, such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where the compounds carry one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like. Pharmaceutically acceptable salts can also include zwitterions.

The term "composition" is intended to encompass a product comprising the specified ingredients in the specified amounts, as well as any product that results, directly or indirectly, from combinations of the specified ingredients in the specified amounts.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

The term "subject" as used herein, refers to an animal, typically a mammal or a human, that will be or has been the object of treatment, observation, and/or experiment. When the term is used in conjunction with administration of a compound or drug, then the subject has been the object of treatment, observation, and/or administration of the compound or drug.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

To "inhibit" or "suppress" or "reduce" a function or activity, such as EBV-positive cancer cell proliferation, is to reduce the function or activity when compared to otherwise same conditions except for a condition or parameter of interest, or alternatively, as compared to another condition(s).

Other definitions for selected terms used herein may be found within the detailed description of the present disclosure and apply throughout. Unless otherwise defined, all other technical terms used herein have the same meaning as commonly understood to one of ordinary skill in the art to which the present disclosure belongs.

Other aspects and advantages of the present invention will be apparent to those skilled in the art from a review of the ensuing description.

The compounds provided herein can comprise an intramolecular charge transfer (ICT)-characterized fluorophore, a peptide comprising a peptide inhibitor sequence and optionally a nucleus localization sequence (NLS), and a zinc binding moiety to increase the inhibitory effect against EBV-positive cancers and maintain the responsive signal of the compound. The resulting compound has improved inhibition on EBNA1, as indicated by MTT assay. Luminescence titration showed that compounds provided herein are highly selective towards EBNA1 over HSA, in addition, the strong binding to EBNA1 was also demonstrated in the presence of $Zn^{2+}$. The compounds provided herein not only provide a powerful and promising probe for use in the treatment, imaging, and diagnosis of EBV-positive cells (e.g., cancer cells).

Provided herein is a compound of Formula I:

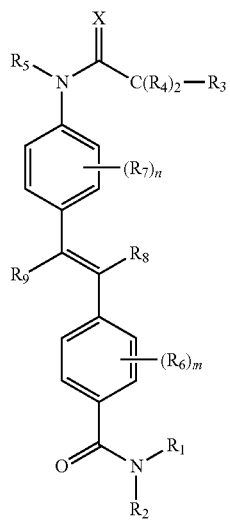

I or a pharmaceutically acceptable salt thereof, wherein
m is a whole number selected from 0-4;
n is a whole number selected from 0-4;
p is a whole number selected from 0-4;
X is $H_2$, S, or O;
each instance of R is independently H or alkyl;
$R_1$ is selected from the group consisting of SEQ ID NO:1 (CYFMVF), SEQ ID NO:2 (YFMVF), SEQ ID NO:3 (CAhxRrRKGGYFMVF), SEQ ID NO:4 (CAhxYFMVFG-GRrRK), SEQ ID NO:5 (AhxYFIVFGGRrRK), and SEQ ID NO:6 (YFIVF);
$R_2$ is H or alkyl;
$R_3$ is selected from the group consisting of:

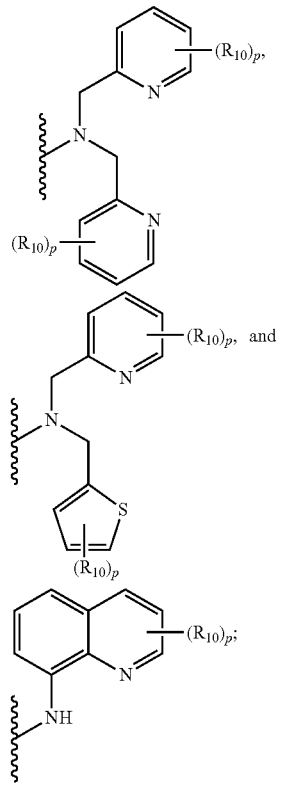

each instance of $R_4$ is independently H or alkyl;
$R_4$ is H or alkyl;
$R_5$ is H or alkyl;
each instance of $R_6$ is independently H, alkyl, alkene, alkyne, cycloalkyl, aryl, heteroaryl, halide, nitrile, nitro, OR, or $NR_2$;
each instance of $R_7$ is independently H, alkyl, alkene, alkyne, cycloalkyl, aryl, heteroaryl, halide, nitrile, nitro, OR, or $NR_2$;
each of $R_8$ and $R_9$ is independently H or alkyl; and
each instance of $R_{10}$ is independently H, alkyl, alkene, alkyne, cycloalkyl, aryl, heteroaryl, halide, nitrile, nitro, OR, or $NR_2$.

The compounds described herein include an olefin. The olefin can exist as an (E)-isomer, a (Z)-isomer, or a combination thereof. In certain embodiments, the olefin is an (E)-isomer.

In instances in which X is $H_2$, the compound of Formula I can be represented by the following structure:

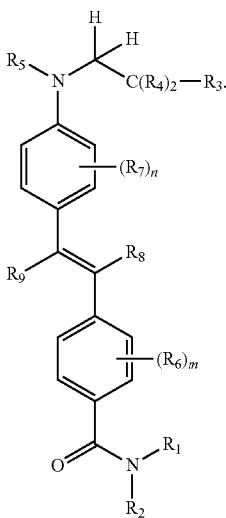

In certain embodiments, $R_1$ is selected from the group consisting of SEQ ID NO:2 (YFMVF), SEQ ID NO:4 (CAhxYFMVFGGRrRK), and SEQ ID NO:6 (YFIVF).

In certain embodiments, each of m, n, and p is independently a whole number selected from 0, 1, and 2. In certain embodiments, each of m, n, and p is independently a whole number selected from 0 and 1.

In certain embodiments, $R_2$ is H or $C_1$-$C_6$ alkyl. In certain embodiments, $R_2$ is H.

In certain embodiments, $R_3$ is selected from the group consisting of:

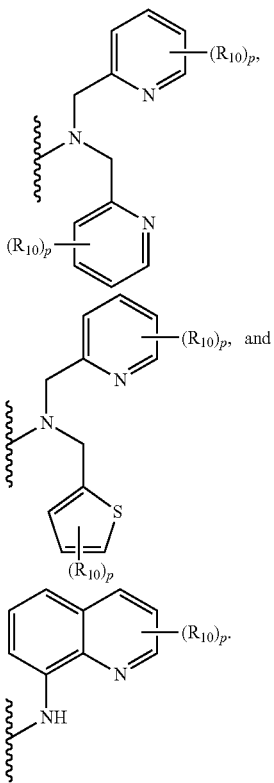

In instances in which $R_3$ is

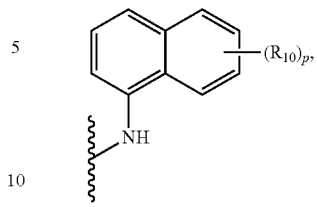

between 1-4 instances of $R_{10}$ can be bound to positions 2, 3, 4, 5, 6, or 7 as shown below:

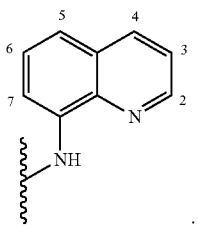

In certain embodiments, $R_4$ is H or $C_1$-$C_6$ alkyl. In certain embodiments, $R_4$ is H.

In certain embodiments, $R_5$ is H or $C_1$-$C_6$ alkyl. In certain embodiments, $R_5$ is H.

In certain embodiments, each of $R_6$, $R_7$, and $R_{10}$ for each occurrence is independently selected from the group consisting of H, $C_1$-$C_6$ alkyl, $C_2$-$C_6$ alkene, $C_2$-$C_6$ alkyne, $C_3$-$C_6$ cycloalkyl, $C_6$-$C_{10}$ aryl, heteroaryl, halide, nitrile, nitro, —OR, and $NR_2$, wherein R for each occurrence is H or $C_1$-$C_6$ alkyl. In certain embodiments, each of $R_6$, $R_7$, and $R_{10}$ for each occurrence is independently selected from the group consisting of H, $C_1$-$C_6$ alkyl, halide, nitrile, and nitro. In certain embodiments, each of $R_6$, $R_7$, and $R_{10}$ is H.

In certain embodiments, each of $R_8$ and $R_9$ is H or $C_1$-$C_6$ alkyl. In certain embodiments, $R_8$ and $R_9$ are each H.

In certain embodiments, the compound has Formula II:

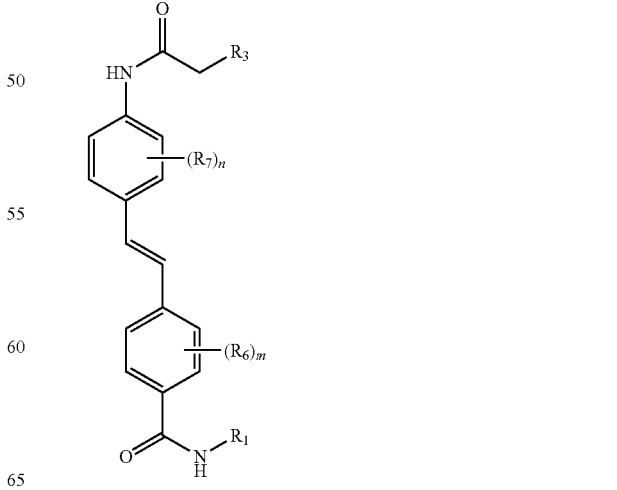

or a pharmaceutically acceptable salt thereof, wherein
m is a whole number selected from 0-4;
n is a whole number selected from 0-4;
p is a whole number selected from 0-4;
$R_1$ is selected from the group consisting of SEQ ID NO:1 (CYFMVF), SEQ ID NO:2 (YFMVF), SEQ ID NO:3 (CAhxRrRKGGYFMVF), SEQ ID NO:4 (CAhxYFMVFGGRrRK), SEQ ID NO:5 (AhxYFIVFGGRrRK), and SEQ ID NO:6 (YFIVF);
$R_3$ is selected from the group consisting of:

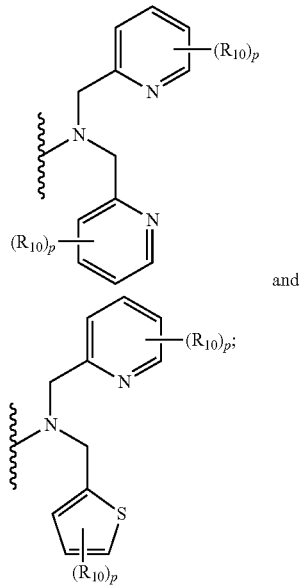

and each instance of $R_6$ is independently H, alkyl, alkene, alkyne, cycloalkyl, aryl, heteroaryl, halide, nitrile, nitro, OR, or $NR_2$;
each instance of $R_7$ is independently H, alkyl, alkene, alkyne, cycloalkyl, aryl, heteroaryl, halide, nitrile, nitro, OR, or $NR_2$;
each of $R_8$ and $R_9$ is independently H or alkyl; and
each instance of $R_{10}$ is independently H, alkyl, alkene, alkyne, cycloalkyl, aryl, heteroaryl, halide, nitrile, nitro, OR, or $NR_2$.

In certain embodiments of the compound of Formula II, each of m, n, and p is independently selected from 0, 1, and 2.

In certain embodiments of the compound of Formula II, each instance of $R_6$ and $R_7$ is independently H, $C_1$-$C_6$ alkyl, $C_2$-$C_6$ alkene, $C_2$-$C_6$ alkyne, $C_3$-$C_6$ cycloalkyl, $C_6$-$C_{10}$ aryl, heteroaryl, halide, nitrile, nitro, —OR, or $NR_2$, wherein R for each occurrence is H or $C_1$-$C_6$ alkyl. In certain embodiments of the compound of Formula II, each instance of $R_6$ and $R_7$ is independently H, $C_1$-$C_6$ alkyl, halide, nitrile, or nitro. In certain embodiments of the compound of Formula II, each $R_6$ and $R_7$ is H.

In certain embodiments of the compound of Formula II, each of $R_8$ and $R_9$ is independently H or $C_1$-$C_6$ alkyl. In certain embodiments of the compound of Formula II, $R_8$ and $R_9$ are each H.

In certain embodiments of the compound of Formula II, each instance of $R_{10}$ is independently H, $C_1$-$C_6$ alkyl, $C_2$-$C_6$ alkene, $C_2$-$C_6$ alkyne, $C_3$-$C_6$ cycloalkyl, $C_6$-$C_{10}$ aryl, heteroaryl, halide, nitrile, nitro, —OR, or $NR_2$, wherein R for each occurrence is H or $C_1$-$C_6$ alkyl. In certain embodiments of the compound of Formula II, each instance of $R_{10}$ is independently H, $C_1$-$C_6$ alkyl, halide, nitrile, or nitro. In certain embodiments of the compound of Formula II, $R_{10}$ is H.

In certain embodiments of the compound is selected from the group consisting of:

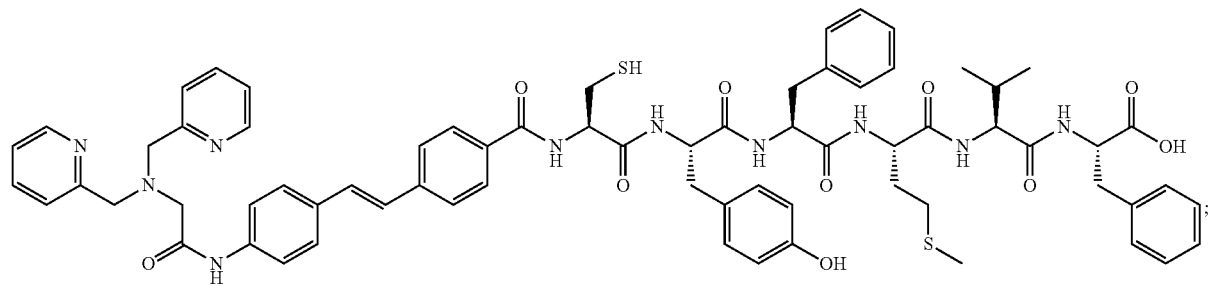

ZRL5P1 [SEQ ID NO: 1 (CYFMVF)]

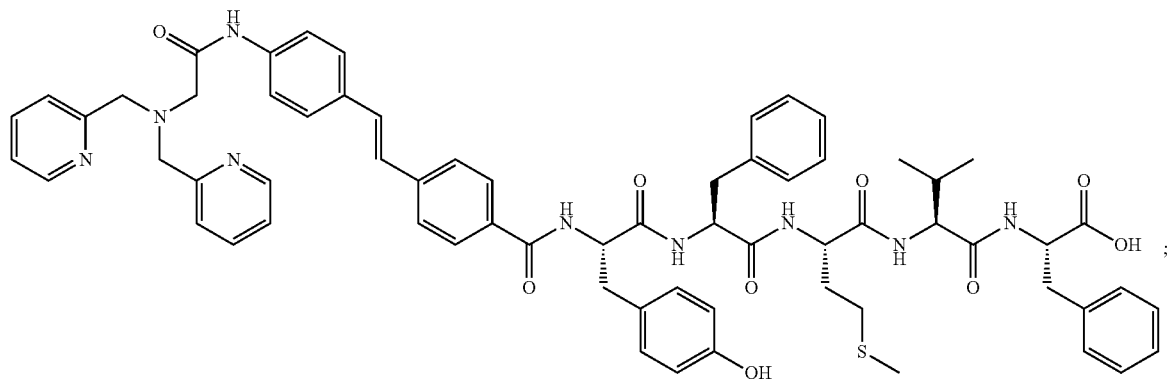

ZRL5P2 [SEQ ID NO: 2 (YFMVF)]

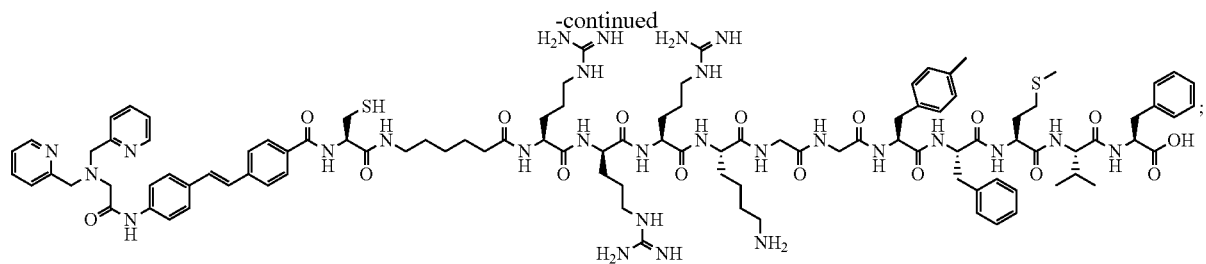
ZRL₅P₃ [SEQ ID NO: 3 (CAhxRrRKGGYFMVF)]
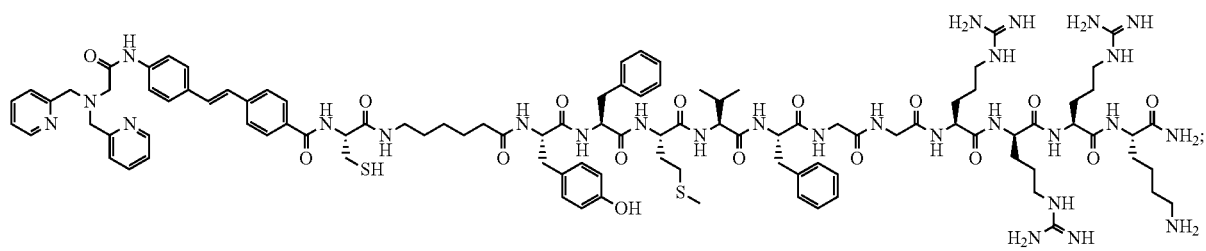
ZRL₅P₄ [SEQ ID NO: 4 (CAhxYFMVFGGRrRK)]
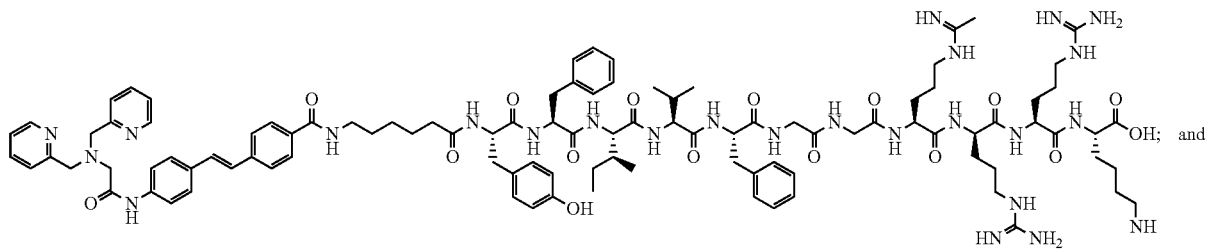
ZRL₅P₆ [SEQ ID NO: 5 (AhxYFIVFGGRrRK)]
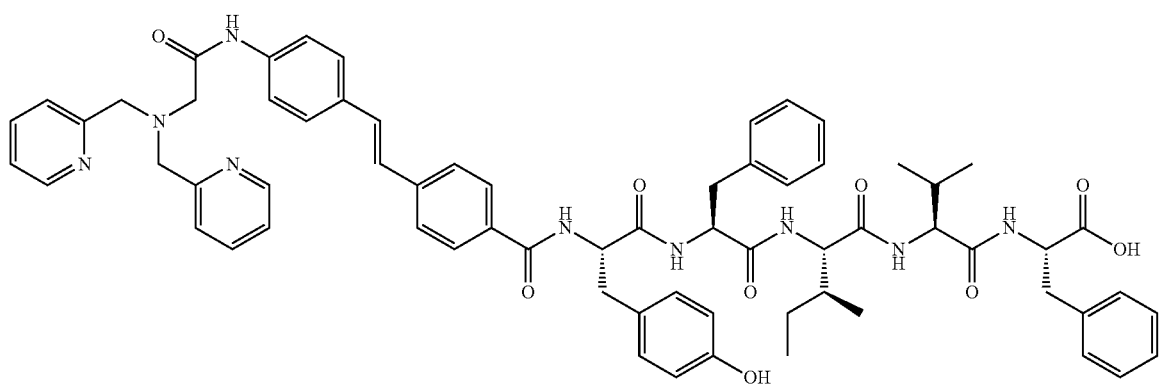
ZRL₅P₅ [SEQ ID NO: 6 (YFIVF)]
or a pharmaceutically acceptable salt thereof.

In certain embodiments, the compound is selected from the group consisting of:

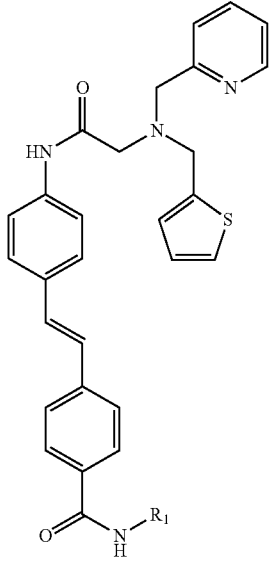

and

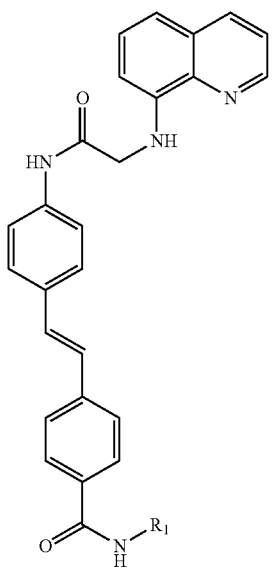

or a pharmaceutically acceptable salt thereof, wherein $R_1$ is selected from the group consisting of SEQ ID NO:1 (CYFMVF), SEQ ID NO:2 (YFMVF), SEQ ID NO:3 (CAhxRrRKGGYFMVF), SEQ ID NO:4 (CAhxYFMVFG-GRrRK), SEQ ID NO:5 (AhxYFIVFGGRrRK), and SEQ ID NO:6 (YFIVF).

In certain embodiments, the compound has the Formula IV:

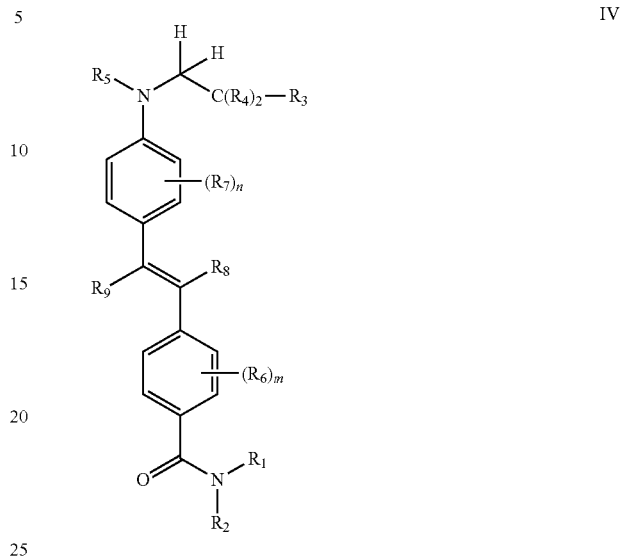

or a pharmaceutically acceptable salt thereof, wherein
m is a whole number selected from 0-4;
n is a whole number selected from 0-4;
p is a whole number selected from 0-4;
each instance of R is independently H or alkyl;
$R_1$ is selected from the group consisting of SEQ ID NO:1 (CYFMVF), SEQ ID NO:2 (YFMVF), SEQ ID NO:3 (CAhxRrRKGGYFMVF), SEQ ID NO:4 (CAhxYFMVFG-GRrRK), SEQ ID NO:5 (AhxYFIVFGGRrRK), and SEQ ID NO:6 (YFIVF);
$R_2$ is H or alkyl;
$R_3$ is selected from the group consisting of:

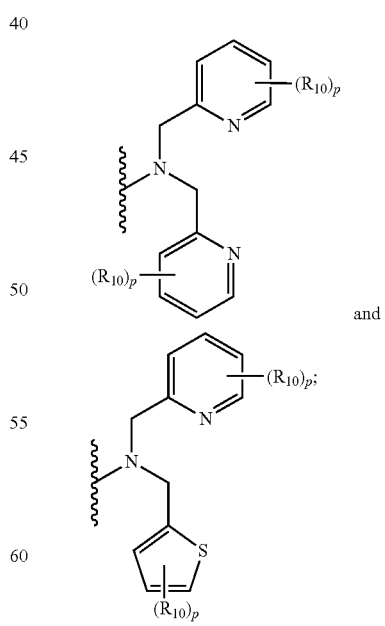

each instance of $R_4$ is independently H or alkyl;
$R_4$ is H or alkyl;
$R_5$ is H or alkyl;

each instance of $R_6$ is independently H, alkyl, alkene, alkyne, cycloalkyl, aryl, heteroaryl, halide, nitrile, nitro, OR, or $NR_2$;

each instance of $R_7$ is independently H, alkyl, alkene, alkyne, cycloalkyl, aryl, heteroaryl, halide, nitrile, nitro, OR, or $NR_2$;

each of $R_8$ and $R_9$ is independently H or alkyl; and each instance of $R_{10}$ is independently H, alkyl, alkene, alkyne, cycloalkyl, aryl, heteroaryl, halide, nitrile, nitro, OR, or $NR_2$.

In certain embodiments of the compound of Formula IV, each of m, n, and p is independently selected from 0, 1, or 2.

In certain embodiments of the compound of Formula IV, $R_2$ and $R_5$ are each H.

In certain embodiments of the compound of Formula IV, $R_6$, $R_7$, and $R_{10}$ for each instance is independently selected from the group consisting of H, $C_1$-$C_6$ alkyl, $C_2$-$C_6$ alkene, $C_2$-$C_6$ alkyne, $C_3$-$C_6$ cycloalkyl, $C_6$-$C_{10}$ aryl, heteroaryl, halide, nitrile, nitro, —OR, and $NR_2$, wherein R for each occurrence is H or $C_1$-$C_6$ alkyl. In certain embodiments, $R_6$, $R_7$, and $R_{10}$ for each instance is independently H, $C_1$-$C_6$ alkyl, halide, nitrile, or nitro. In certain embodiments, $R_6$, $R_7$, and $R_{10}$ are each H.

In certain embodiments of the compound of Formula IV, $R_8$ and $R_9$ are each H.

In certain embodiments of the compound of Formula IV, the compound is selected from the group consisting of:

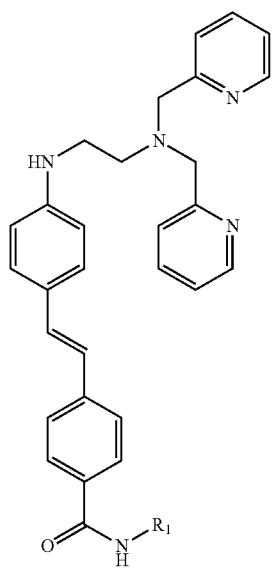

and

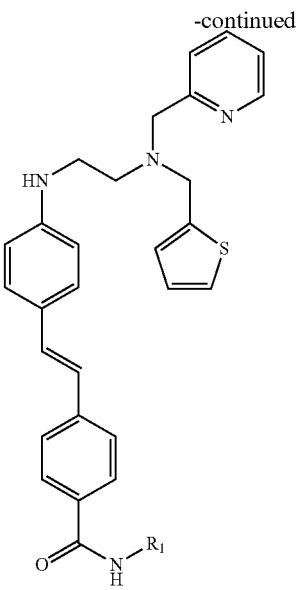

or a pharmaceutically acceptable salt thereof, wherein $R_1$ is selected from the group consisting of SEQ ID NO:1 (CYFMVF), SEQ ID NO:2 (YFMVF), SEQ ID NO:3 (CAhxRrRKGGYFMVF), SEQ ID NO:4 (CAhxYFMVFG-GRrRK), SEQ ID NO:5 (AhxYFIVFGGRrRK), and SEQ ID NO:6 (YFIVF).

The present disclosure also provides a pharmaceutical composition comprising any one of the compounds described herein and at least one pharmaceutically acceptable excipient.

The compounds described herein and their pharmaceutically acceptable salts can be administered to a subject either alone or in combination with pharmaceutically acceptable carriers or diluents in a pharmaceutical composition according to standard pharmaceutical practice. The compounds can be administered orally or parenterally. Parenteral administration includes intravenous, intramuscular, intraperitoneal, subcutaneous and topical, the preferred method being intravenous administration.

Accordingly, the present disclosure provides pharmaceutically acceptable compositions, which comprise a therapeutically-effective amount of one or more of the compounds described herein, formulated together with one or more pharmaceutically acceptable carriers (additives) and/or diluents. The pharmaceutical compositions of the present disclosure may be specially formulated for administration in solid or liquid form, including those adapted for the following: (1) parenteral administration, for example, by subcutaneous, intramuscular, intravenous or epidural injection as, for example, a sterile solution or suspension, or sustained-release formulation; and (2) oral administration, for example, drenches (aqueous or non-aqueous solutions or suspensions), tablets, e.g., those targeted for buccal, sublingual, and systemic absorption, boluses, powders, granules, pastes for application to the tongue. The preferred method of administration of compounds of the present invention is parental administration (intravenous).

As set out herein, certain embodiments of the compounds described herein may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the bromide, chloride, sulfate, bisulfate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like.

The pharmaceutically acceptable salts of the compounds of the present disclosure include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds described herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing these formulations or compositions include the step of bringing into association a compound described herein with the carrier and, optionally, one or more accessory ingredients. In general, the formulations are prepared by uniformly and intimately bringing into association a compound of the present invention with liquid carriers (liquid formulation), liquid carriers followed by lyophilization (powder formulation for reconstitution with sterile water or the like), or finely divided solid carriers, or both, and then, if necessary, shaping or packaging the product.

Pharmaceutical compositions of the present disclosure suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, chelating agents, solutes which render the formulation isotonic with the blood of the intended recipient or suspending or thickening agents. In the examples, the active ingredients are brought together with the pharmaceutically acceptable carriers in solution and then lyophilized to yield a dry powder. The dry powder is packaged in unit dosage form and then reconstituted for parental administration by adding a sterile solution, such as water or normal saline, to the powder.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the compounds of the present invention may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Synthesis.

An exemplary synthesis of $ZRL_5P_n$ is shown in Scheme 1. The synthetic route started from a Horner-Wadsworth-Emmons olefination to prepare 2. Reduction of the nitro group in 2 using stannous chloride gave 3, which was then reacted with chloroacetyl chloride to produce 4. Reaction of 4 with di-2-picolylamine (DPA) using N,N-diisopropylethylamine (DIPEA) as base followed by ester saponification and peptide conjugation gave 7. Cleavage of the resin on 7 produced the target probe $ZRL_5P_n$.

Scheme 1 Synthetic route of ZRL$_5$P$_2$/ZRL$_5$P$_4$/ZRL$_5$P$_6$(P$_2$, SEQ ID NO: 2 (YFMVF); P$_4$, SEQ ID NO: 4 (CAhxYFMVFGGRrRK); P$_6$, SEQ ID NO: 5 (AhxYFIVFGGRrRK).

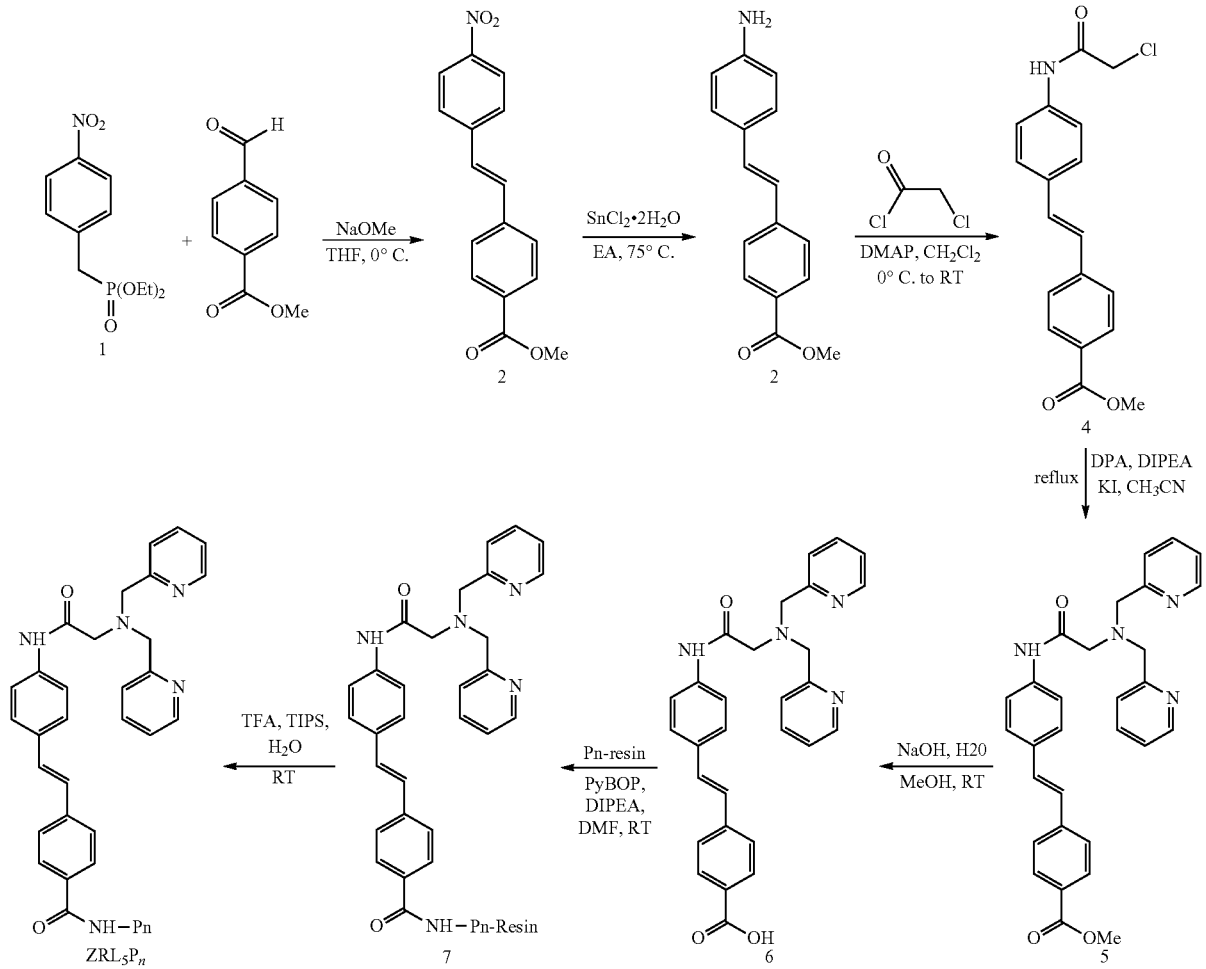

The compound described herein can bind to and inhibit the dimerization of EBNA1. Consequently, the compounds described herein can be used to treat conditions or disease states in which inhibition of the dimerization of EBNA1 has a therapeutic effect. Provided herein is a method of treating an Epstein-Barr virus (EBV)-positive cell in a patient in need thereof comprising administering a therapeutically effective amount of a compound as described herein to the patient. In certain embodiments, the EBV-positive cell is a cancerous cell. In certain embodiments, the cancerous cell is Burkitt's lymphoma, non-Hodgkin's lymphoma, Hodgkin's disease, T-cell lymphoma, B-cell lymphoma, transplant-associated lymphoproliferative disorders, nasopharyngeal carcinoma, gastric adenocarcinoma, parotid carcinoma, or leiomyosarcoma.

Also provided is a method of imaging an EBV-positive cell comprising the step of contacting the EBV-positive cell with a compound as described herein and measuring the fluorescence of the compound. In certain embodiments, the step of measuring the fluorescence comprises two-photon excitation microscopy. In certain embodiments, the step of measuring the fluorescence comprises irradiating the EBV-positive cell in the presence of the compound as described herein with light at a wavelength between 650 to 750 nm and detecting emitted light.

EBNA1 has several functional domains, among them, there is a small domain, termed unique region 1 ("UR1", a.a. 64-89), was reported to coordinate zinc through a pair of cysteines contained within it. Point mutations of the cysteines in UR1 eliminates the ability of EBNA1 to coordinate zinc, self-associate, and activate transcription. Thus, the coordination of zinc is critical for the self-association, transactivation and transactivation-related cellular functions of EBNA1.

The compounds provided herein not only localized to the nucleus where EBNA1 is primarily located, but also showed responsive emission towards the binding of EBNA1.

Figure 6A:
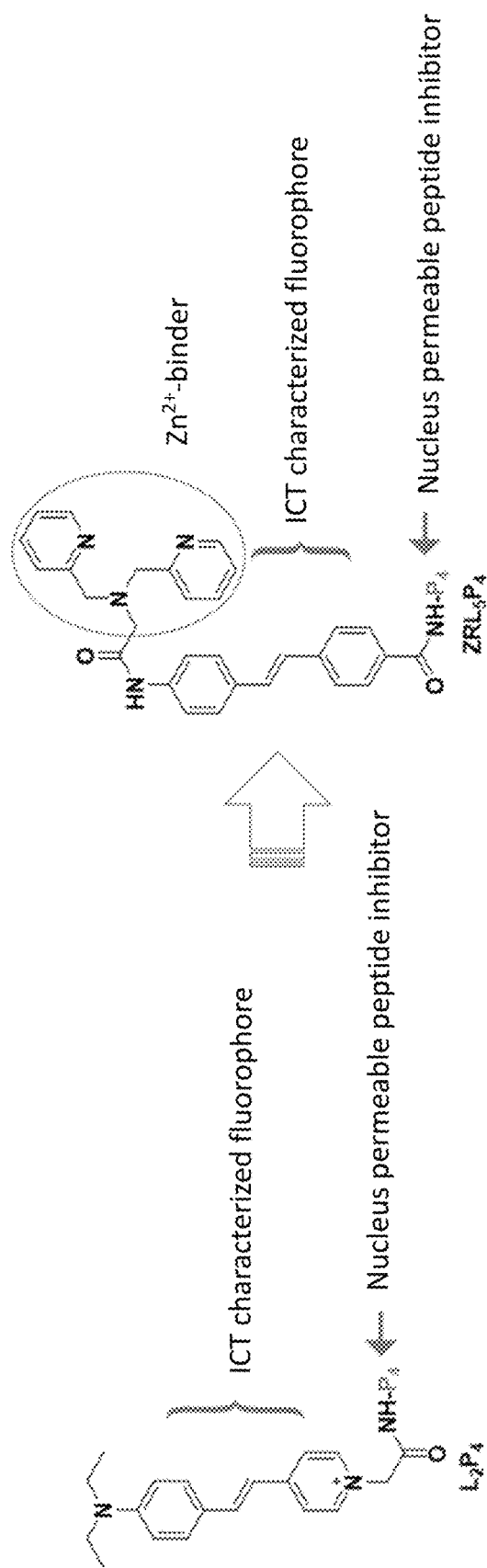
FIG. 6A shows chemical structures of $L_2P_4$ (left) and $ZRL_5P_4$ (right).

In order to determine whether the overall efficacy of a probe could be enhanced by taking advantage of the necessity of zinc coordination by EBNA1, an all-in-one probe, ZRL$_5$P$_4$, was designed and synthesized (FIG. 6A).

Figure 1:
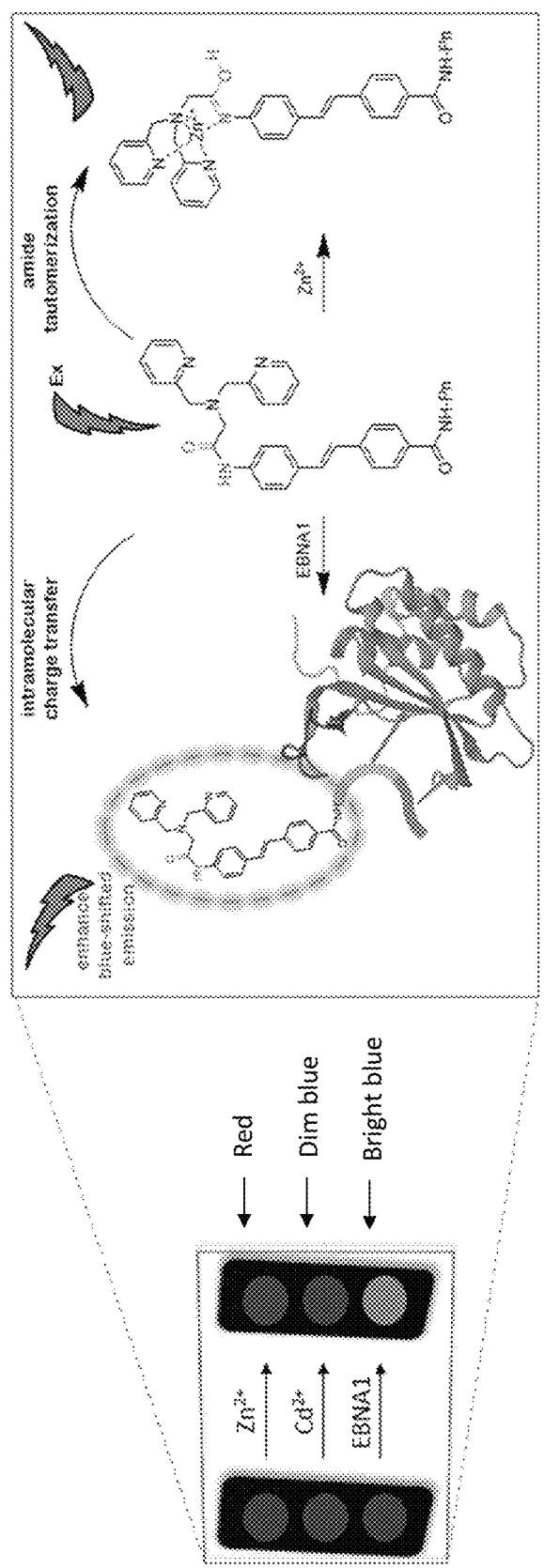
FIG. 1 shows the schematic illustration of the dual-responsive emission for the binding to $Zn^{2+}$/EBNA1 and the blockage on EBNA1 dimerization of a compound as described herein.

In this scaffold, an amide group was used to link two moieties—the peptide conjugated fluorophore and a DPA zinc chelator. The amide linked DPA served as a responsive zinc chelator, and amide tautomerization with red-shifted emission can be triggered when it coordinates zinc. The N atom in the amide linker can also act as donor, with the carbonyl group in the other side of the probe serving as the acceptor, thus the ICT (intramolecular charge transfer) characterized emission with enhanced blue-shifted emission can be triggered if the probe binds EBNA1. Thereby, the dual-responsive emission can be reflected for the probe when binding $Zn^{2+}$ and/or EBNA1. Advantageously, as described in detail below, the zinc binding moiety and the peptide motif in the compound of Formula I can function synergistically to inhibit EBNA1, such as to inhibit in self-association of EBNA1 and transactivation by EBNA1, and the blockage on EBNA1 dimerization, and thus achieved better inhibitory effect as shown in FIG. 1.

A critical constraint for the development of overexpressed protein targeting cancer therapy is the genetic variants in different human species. For EBV associated cancers, as the only viral protein expressed in all EBV-associated tumors, EBNA1 plays a vital role in regulating viral genome in the infected cells. Thus, EBNA1 protein not only serves as a perfect marker for clinical imaging, but also a molecular target for treatment. Yet, current studies present that the gene varies frequently on EBNA1 that exists in Chinese and Indonesian nasopharyngeal carcinoma (NPC) samples. Under this circumstance, the inhibition of EBV associated cancer growth has also been weakened by the reported EBNA1 targeting agents.

It is known that zinc coordination by EBNA1 contributes to EBNA1 self-association and activates transcription by EBNA1. It is show that the blockage of zinc coordination by EBNA1 can increase the inhibitory effect. From preliminary data, the inhibition effect of EBV cancer development can be 4 times stronger than EBNA1 dimerization inhibitors using only a "single" approach (i.e., without a zinc binding site). The "twin" inhibition effect can be "directly" monitored by the dual-responsive emission change (Zn-21 nm red shift of the emission and EBNA1-39 nm blue shift of the emission; kinetic) in aqueous, in vitro/in vivo and the heat change by isothermal calorimetry titration (thermodynamic) in aqueous upon binding to EBNA1 ($K_d$, 19.1 μM). The compounds described herein provide a new cancer inhibition approach—interference in both cellular cofactor and physical binding between the protein dimerization, which can be used in the treatment of EBV latently-infected tumors and puts forward the design strategy by incorporating other co-factors to enhance the overall treatment effect.

Rational Probe Design and Molecular Dynamic Simulations of the New Zinc Chelating Probe $ZRL_5P_4$.

To determine the interactions between $ZRL_5P_4$ and EBNA1 DNA-binding domain (DBD), as well as to determine whether the $Zn^{2+}$-bound $ZRL_5P_4$ might affect its interaction with the DBD, molecular dynamics (MD) simulations were conducted using the previous resolved structure of the EBNA1 DBD. The X-ray crystal structures have been solved only for EBNA1 DBD in its apo and DNA-bound forms, whereas the crystal structures of the rest of an EBNA1 monomer are not available at present. The X-ray crystal structure of EBNA1 DBD (protein database ID, 1B3T; chain A; residue 461 to 607) is an α/β-mixed fold comprised of four α-helix and four β-sheet motifs that are linked by several loops (FIG. 1). The beta sheets, β1-β4, drive formation of the dimer via hydrophobic interaction which represents the first EBNA1 dimerization interface which is located at the carboxyl-terminus. The ligand $P_4$ was first docked into the dimeric interface of the EBNA1 DBD monomer using the flexible peptide docking tool CABS. The previously defined $P_4$—EBNA1 complex model was chosen and subjected to a further 500 ns of simulation (FIG. 7). The penta-peptide $P_2$ (YFMVF (SEQ ID NO:2)) can occupy the dimerization interface through a hydrophobic interaction, and the NLS tetrapeptide-RrRK can form salt bridges with the adjacent negatively charged residues ($D_{601}$, $D_{602}$, $D_{605}$) which further enhances the interaction, confirming that $P_4$ is a physical blocker of the EBNA1 dimerization.

Figure 9A:
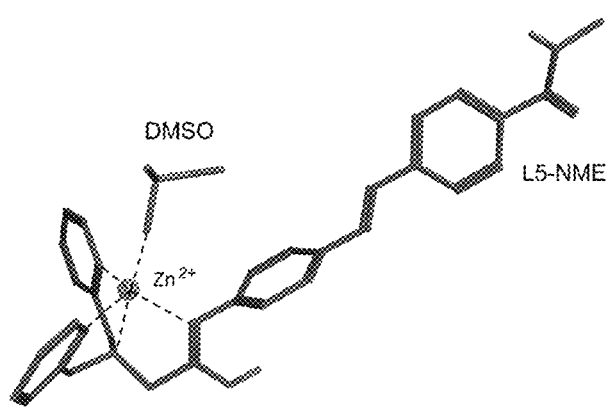
FIG. 9(A-B) shows the putative structures of $Zn^{2+}$-$ZRL_5$-NME complex with 5-coordinated $Zn^{2+}$ where solvent provides 1 coordination site. (A) The calculated 3D structure of DMSO-$Zn^{2+}$-$ZRL_5$-NME. (B) The calculated 3D structure of $H_2O$—$Zn^{2+}$-$ZRL_5$-NME.
Figure 9B:
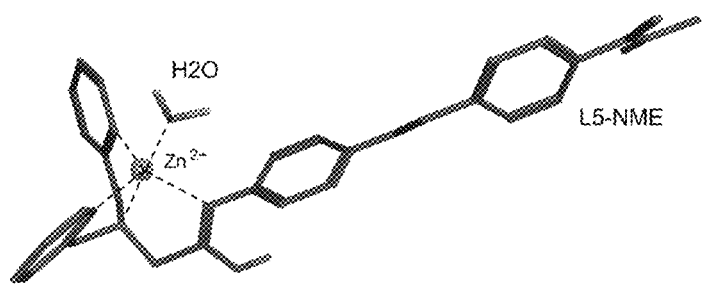
Figure 10A:
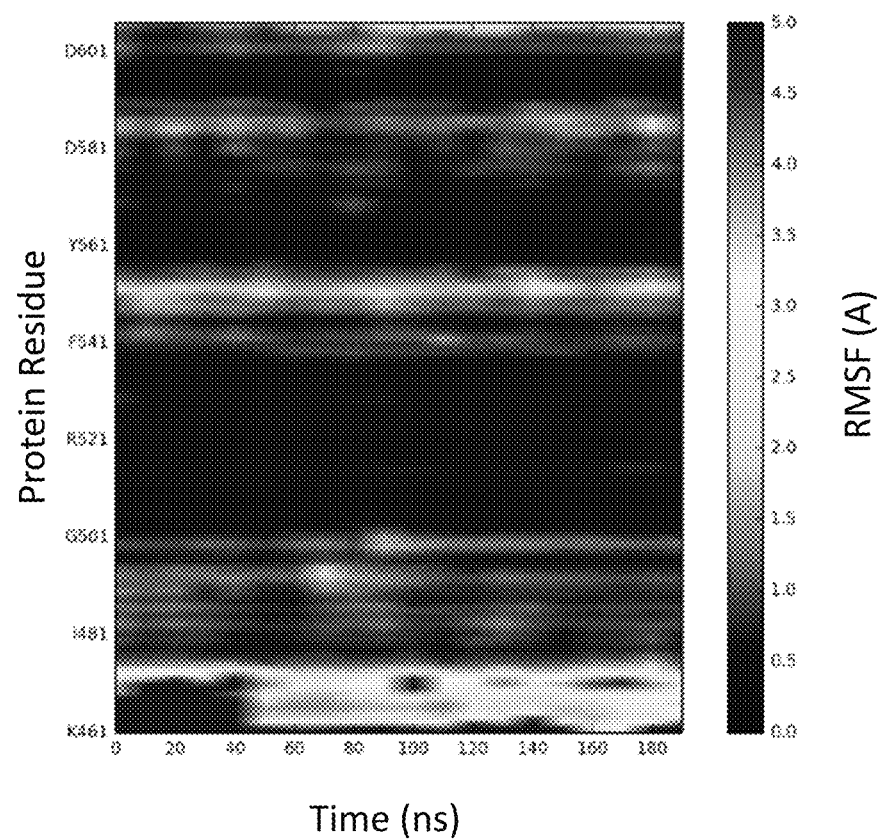
FIG. 10(A-F) shows 200 ns NPT simulation of $ZRL_5P_4$-EBNA1 complex model (#1). (A) RMSF of the putative EBNA1 DBD monomer. (B) RMSF of $ZRL_5P_4$. (C) RMSD of main-chain atoms from EBNA1 DBD with regard to (w.r.t) the initial and end structure. (D) RMSD of main-chain atoms from $ZRL_5P_4$ ligand (YFMVF, SEQ ID NO:2) with regard to the initial and end structure. (E) The salt-bridging between RrRK motif and acid residues in the C-terminus of EBNA1 DBD. (F) The hydrophobic interactions between YFMVF motif and the dimeric interface of EBNA1 DBD.
Figure 10B:
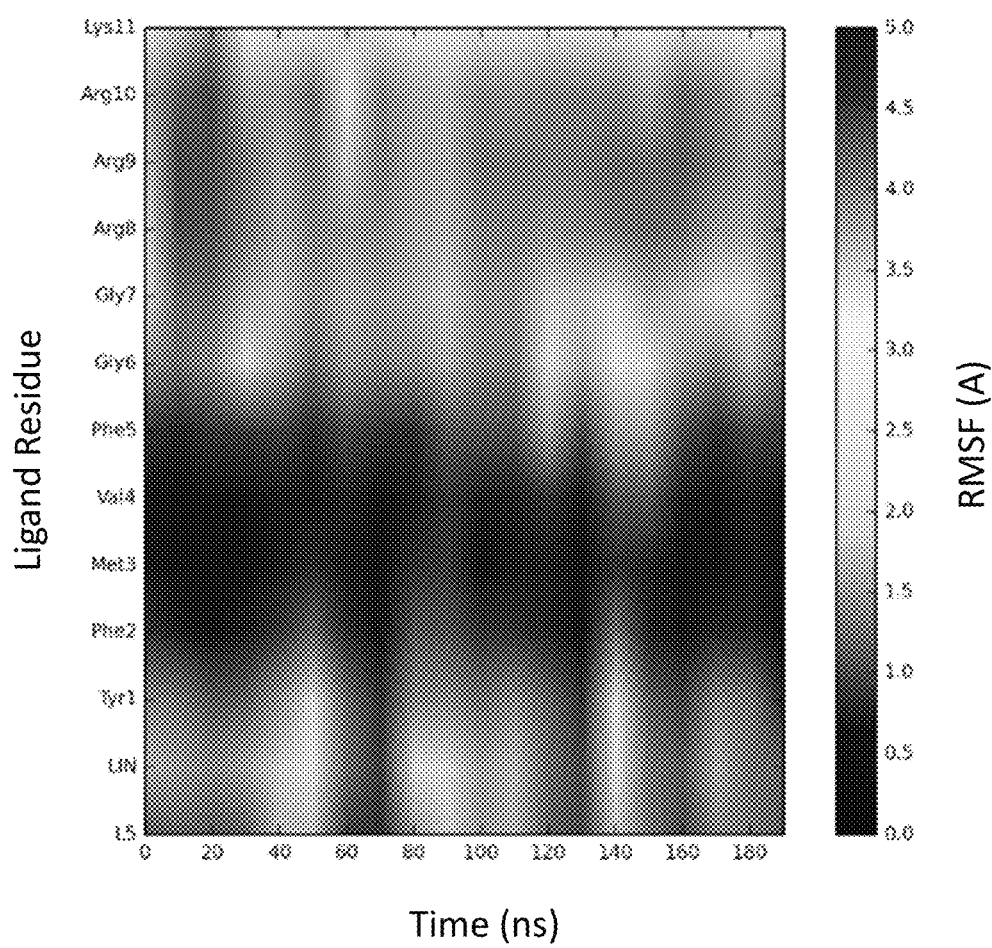
Figure 10C:
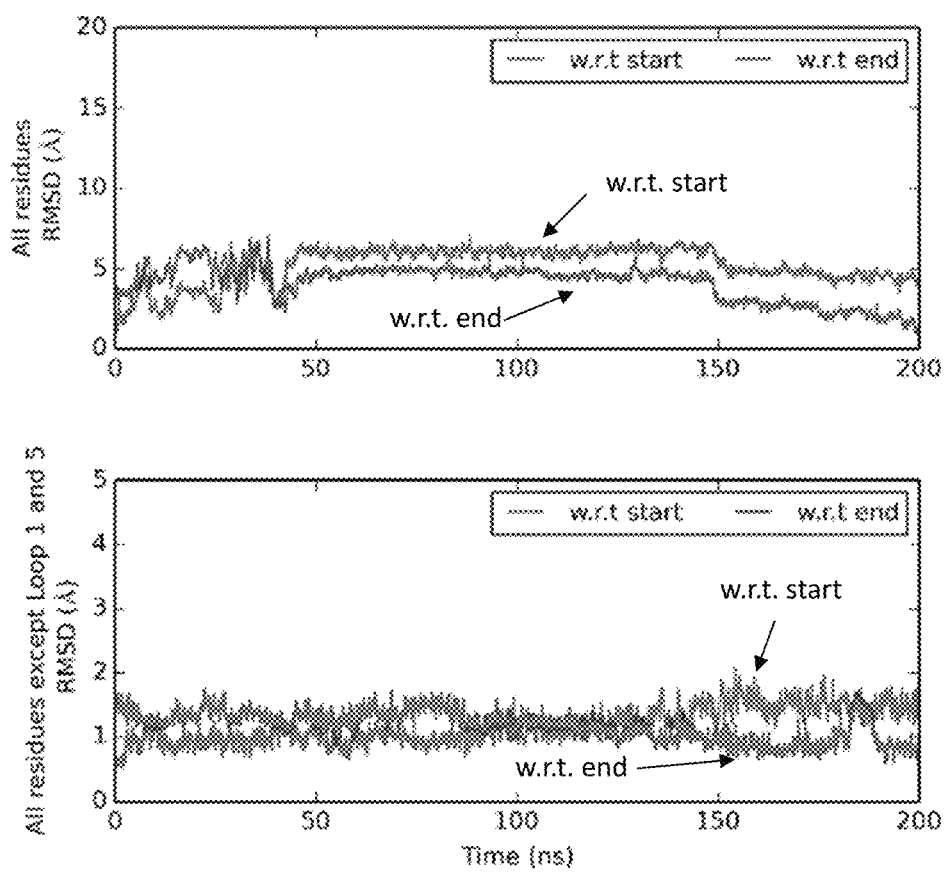
Figure 10D:
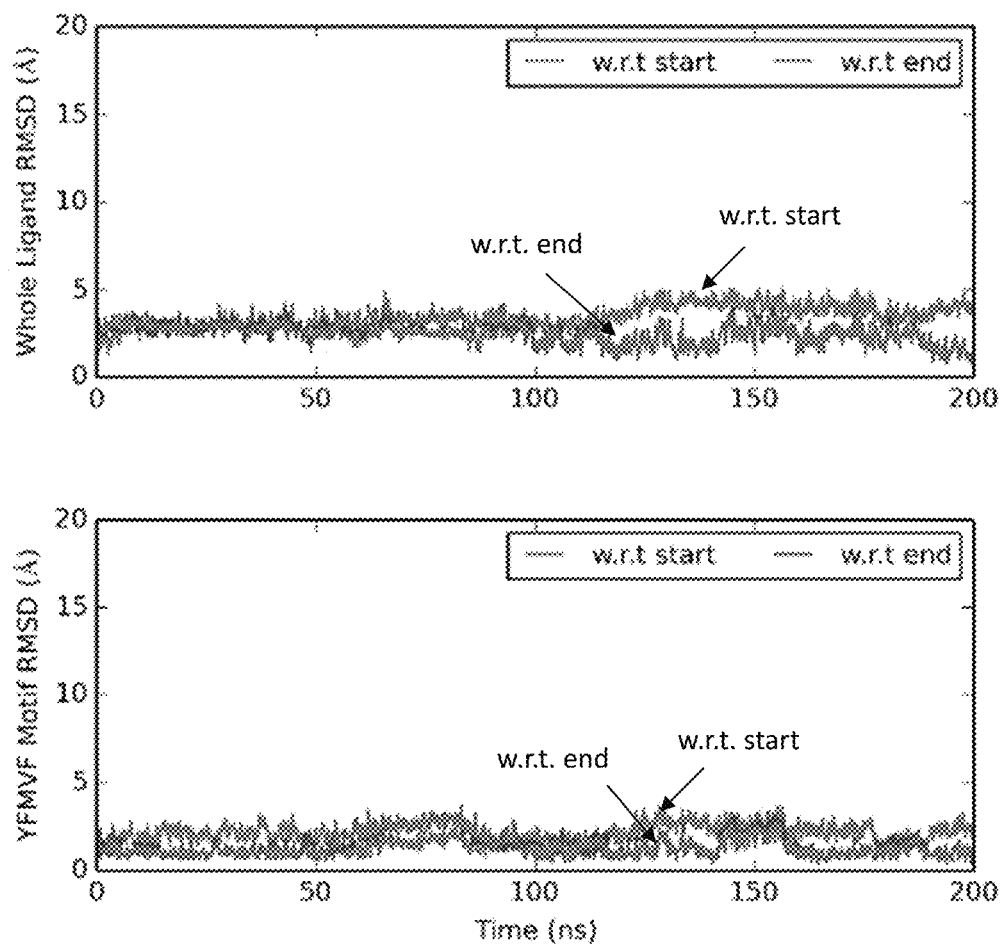
Figure 10E:
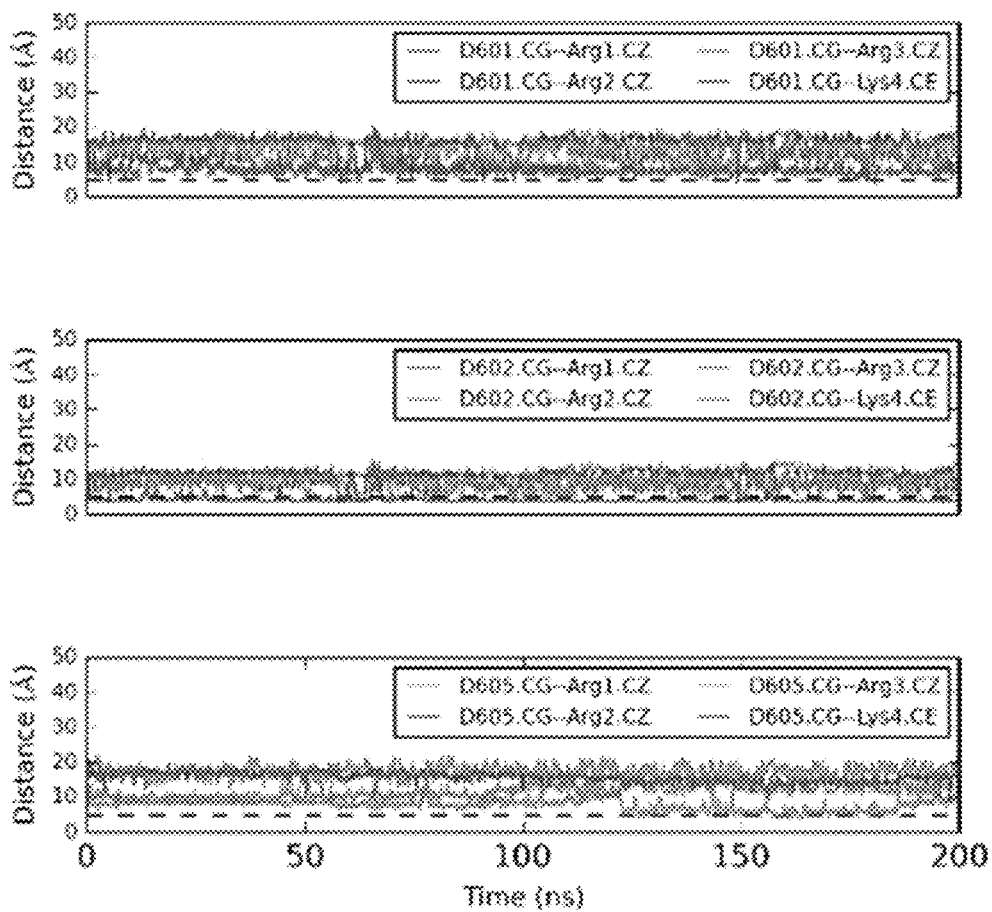
Figure 10F:
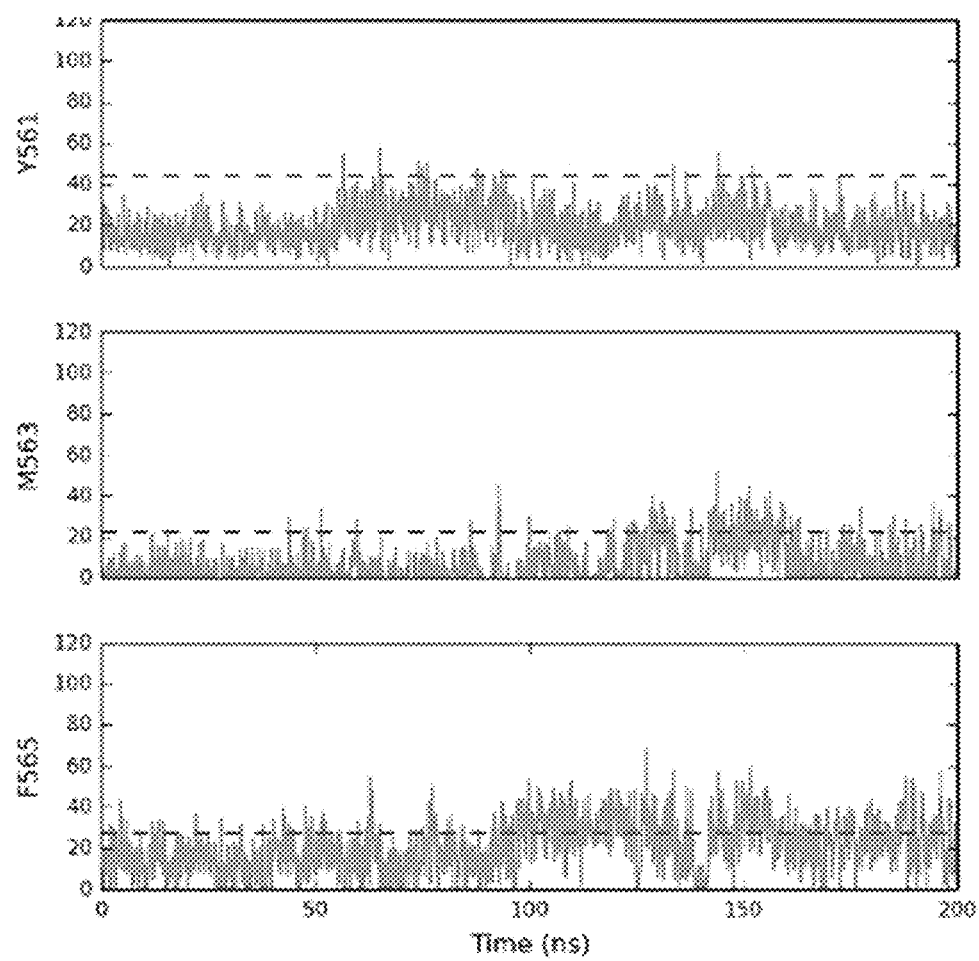
Figure 11A:
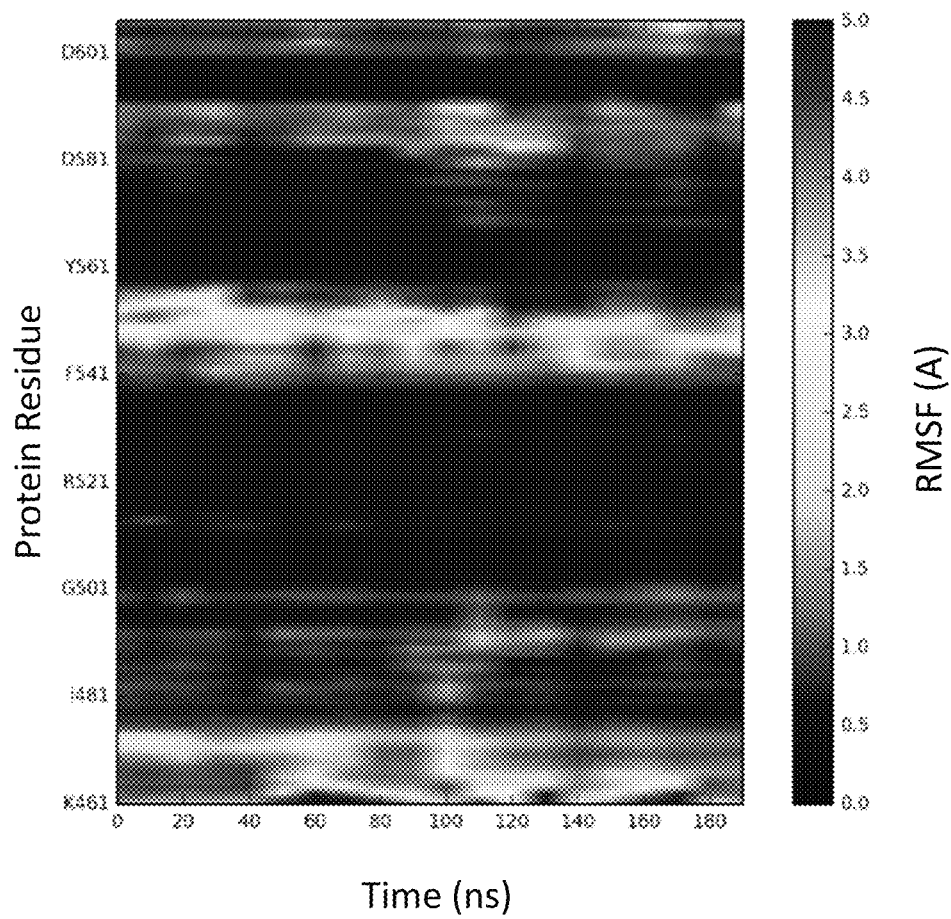
FIG. 11(A-F) shows 200 ns NPT simulation of $ZRL_5P_4$-EBNA1 complex model (#2). (A) RMSF of the putative EBNA1 DBD monomer. (B) RMSF of $ZRL_5P_4$. (C) RMSD of main-chain atoms from EBNA1 DBD with regard to (w.r.t) the initial and end structure. (D) RMSD of main-chain atoms from $ZRL_5P_4$ (YFMVF, SEQ ID NO:2) with regard to the initial and end structure. (E) The salt-bridging between RrRK motif and acid residues in the C-terminus of EBNA1 DBD. (F) The hydrophobic interactions between YFMVF motif and the dimeric interface of EBNA1 DBD.
Figure 11B:
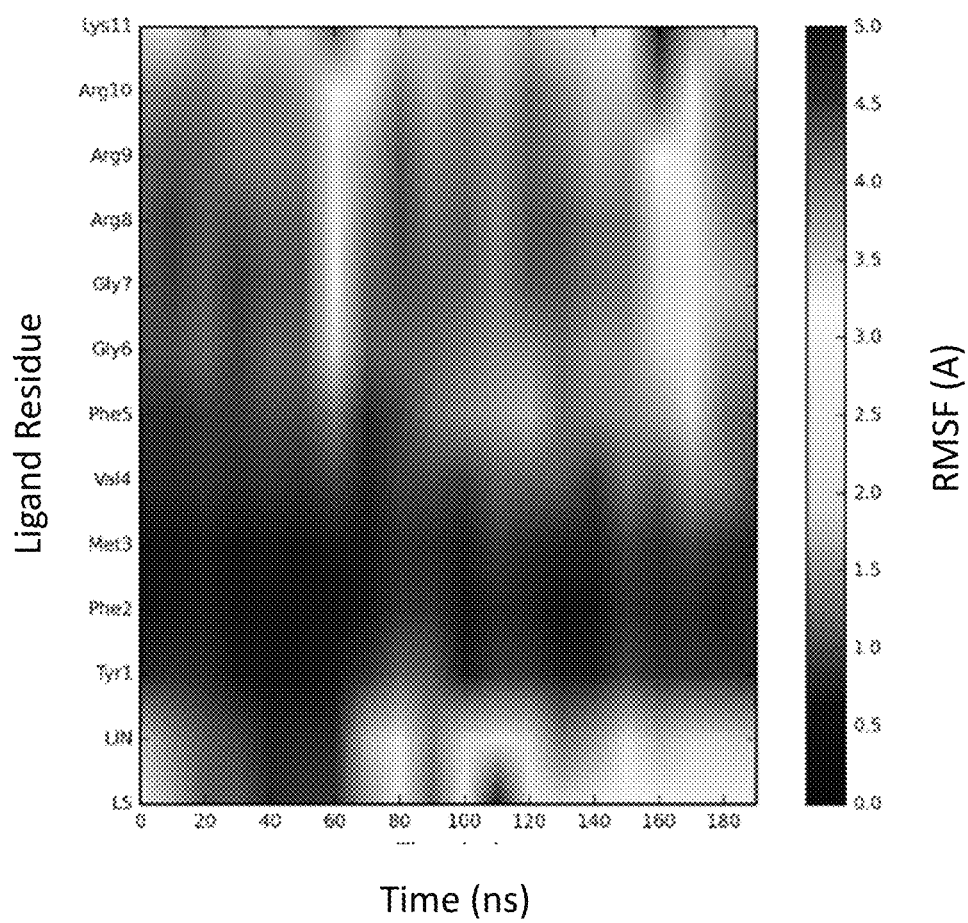
Figure 11C:
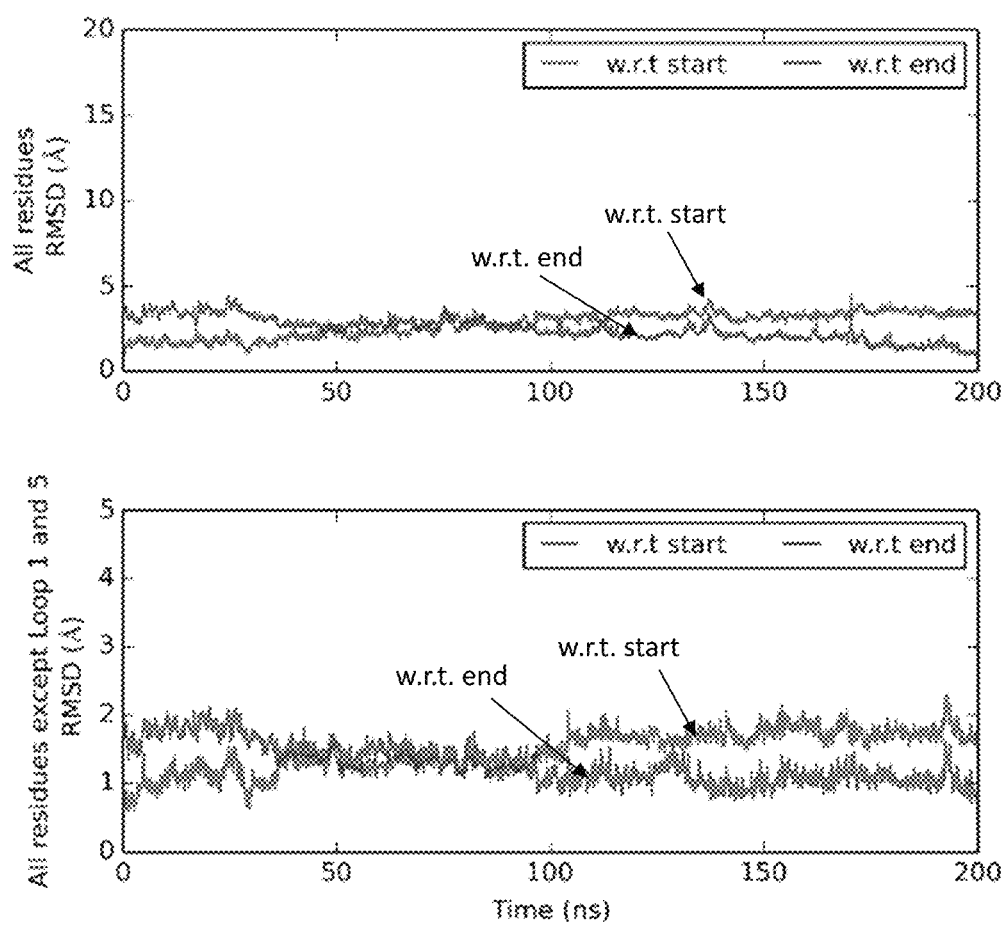
Figure 11D:
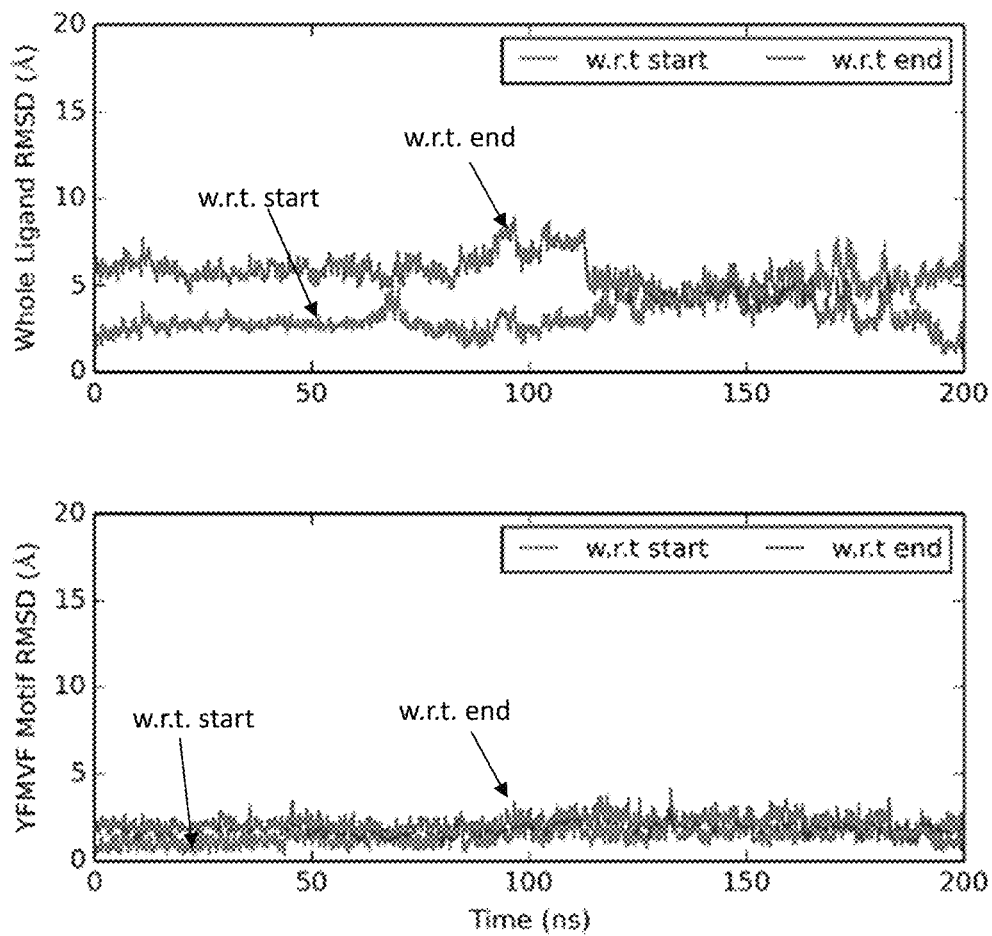
Figure 11E:
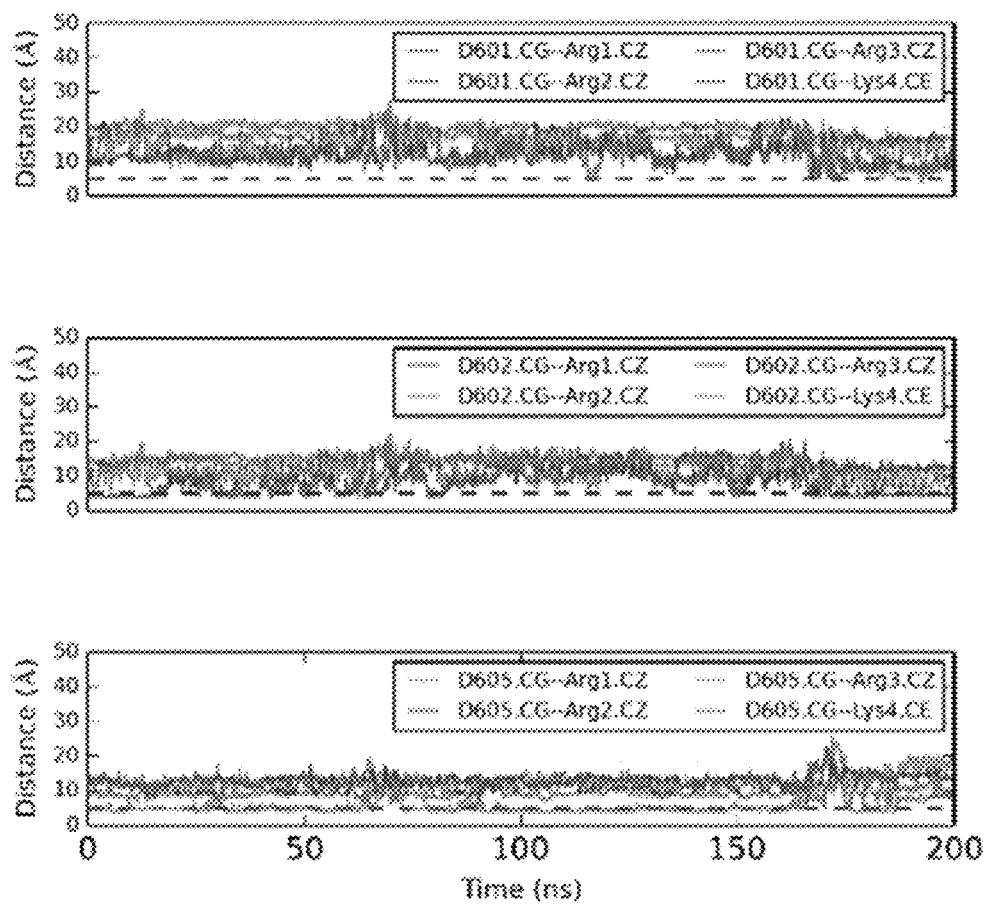
Figure 11F:
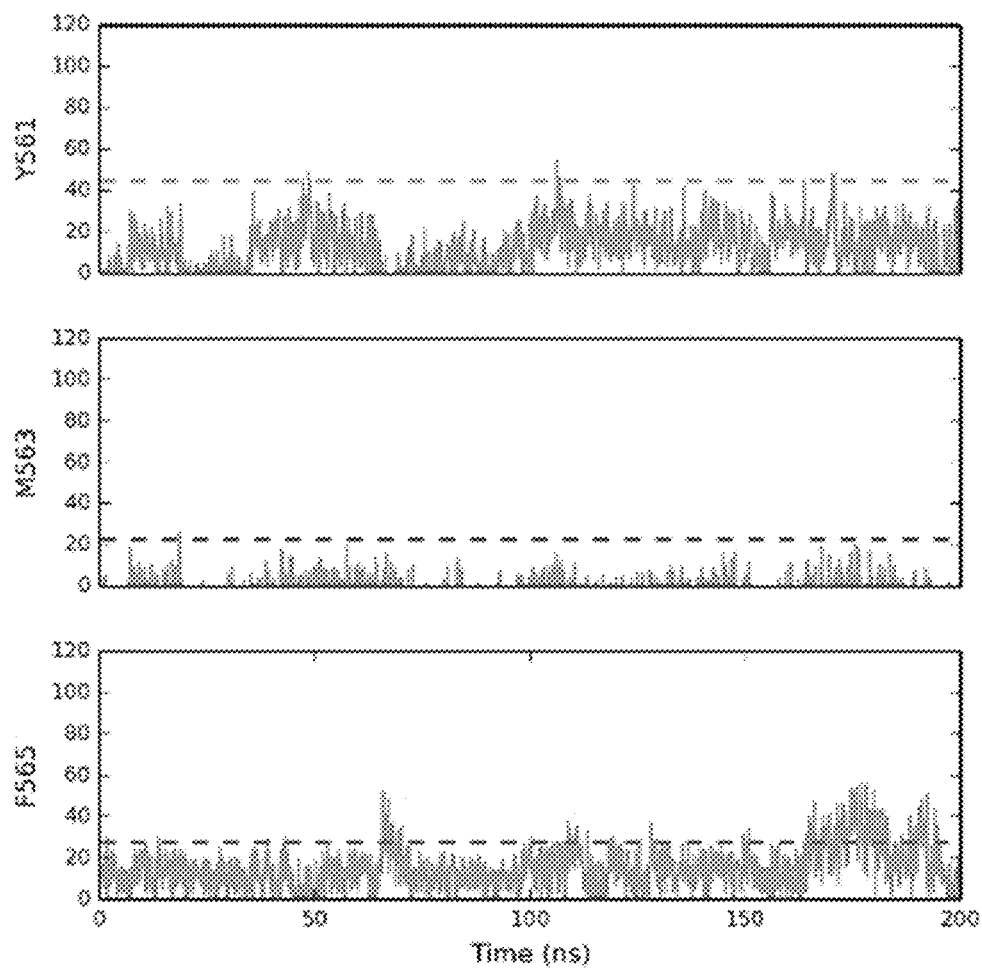
Figure 12A:
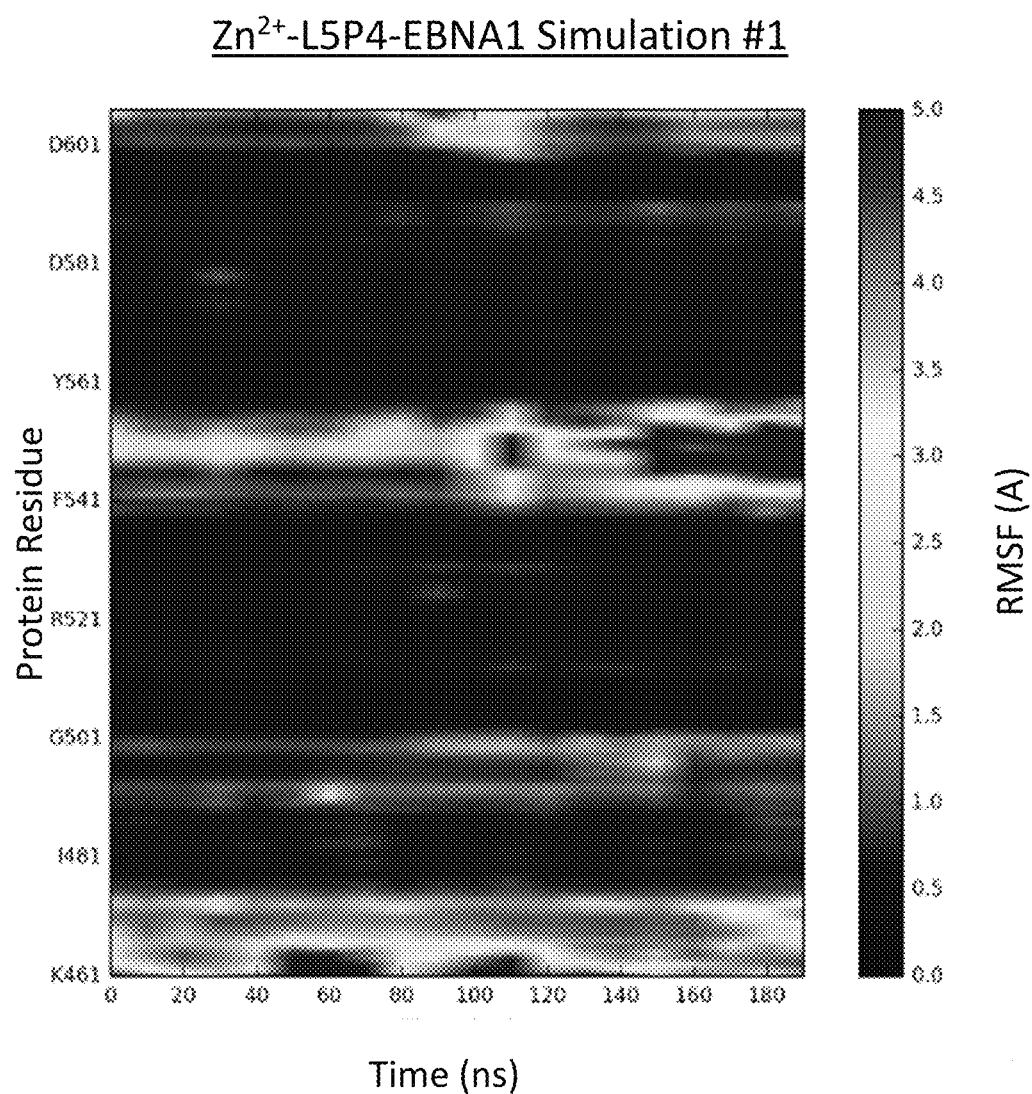
FIG. 12(A-F) shows 200 ns NPT simulation of $Zn^{2+}$-$ZRL_5P_4$-EBNA1 complex model (#1). (A) RMSF of the putative EBNA1 DBD monomer. (B) RMSF of $Zn^{2+}$-$ZRL_5P_4$. (C) RMSD of main-chain atoms from EBNA1 protein with regard to (w.r.t) the initial and end structure. (D)
Figure 12B:
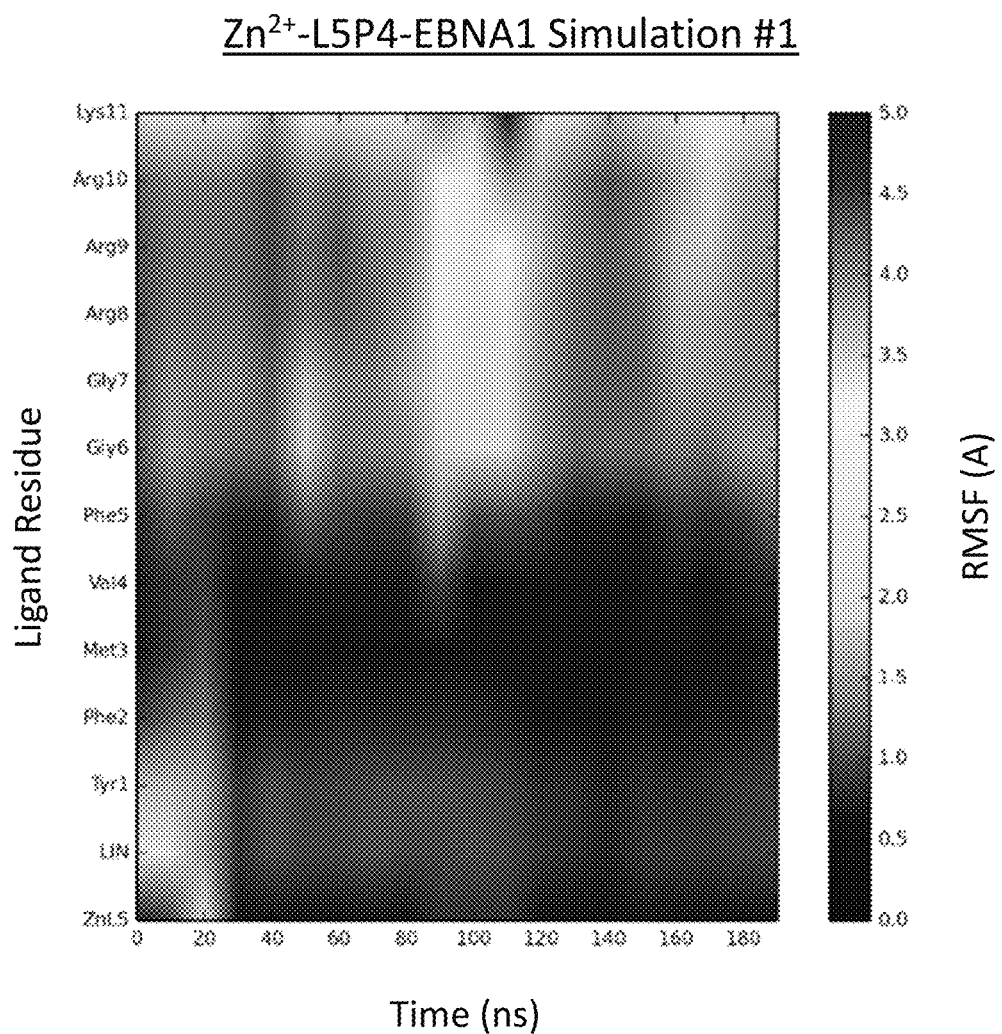
Figure 12C:
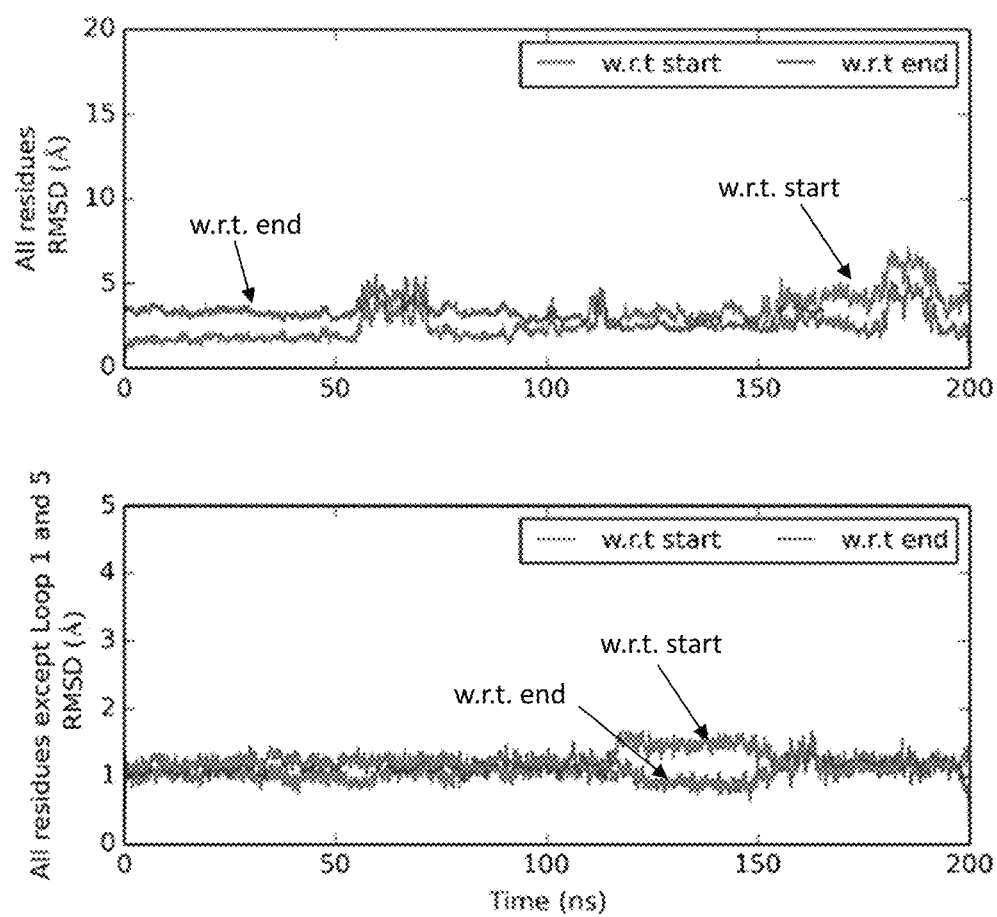
Figure 12D:
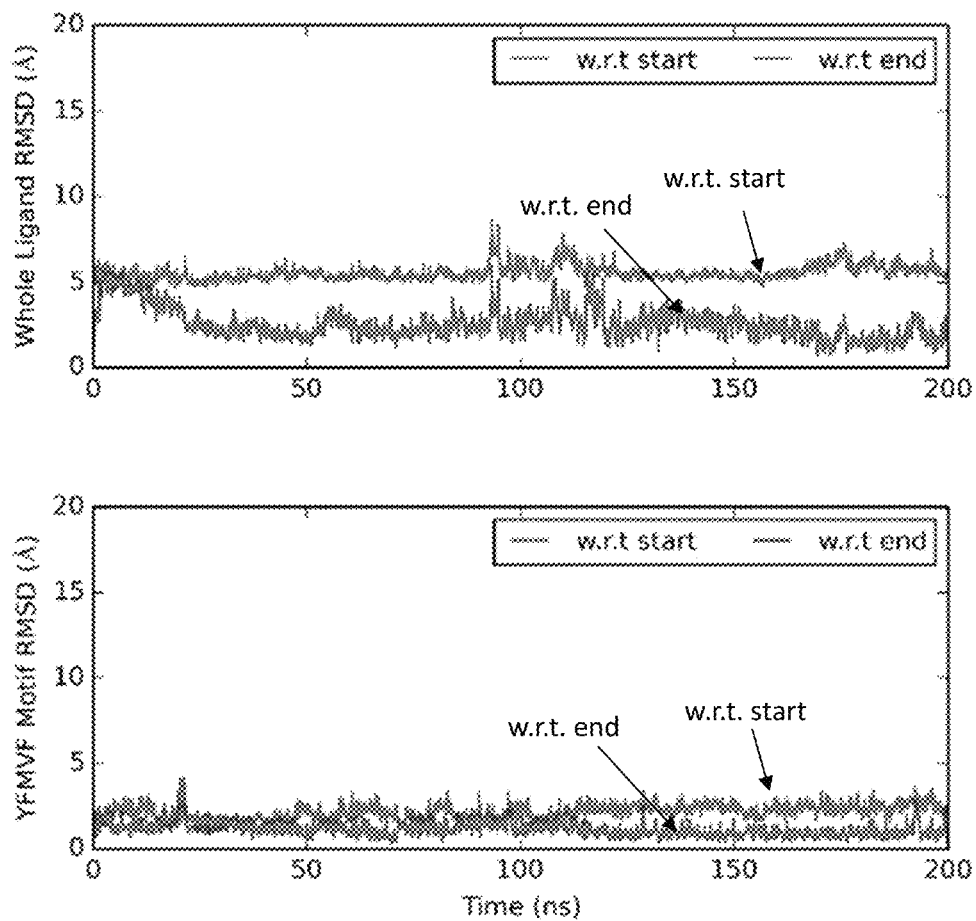
Figure 12E:
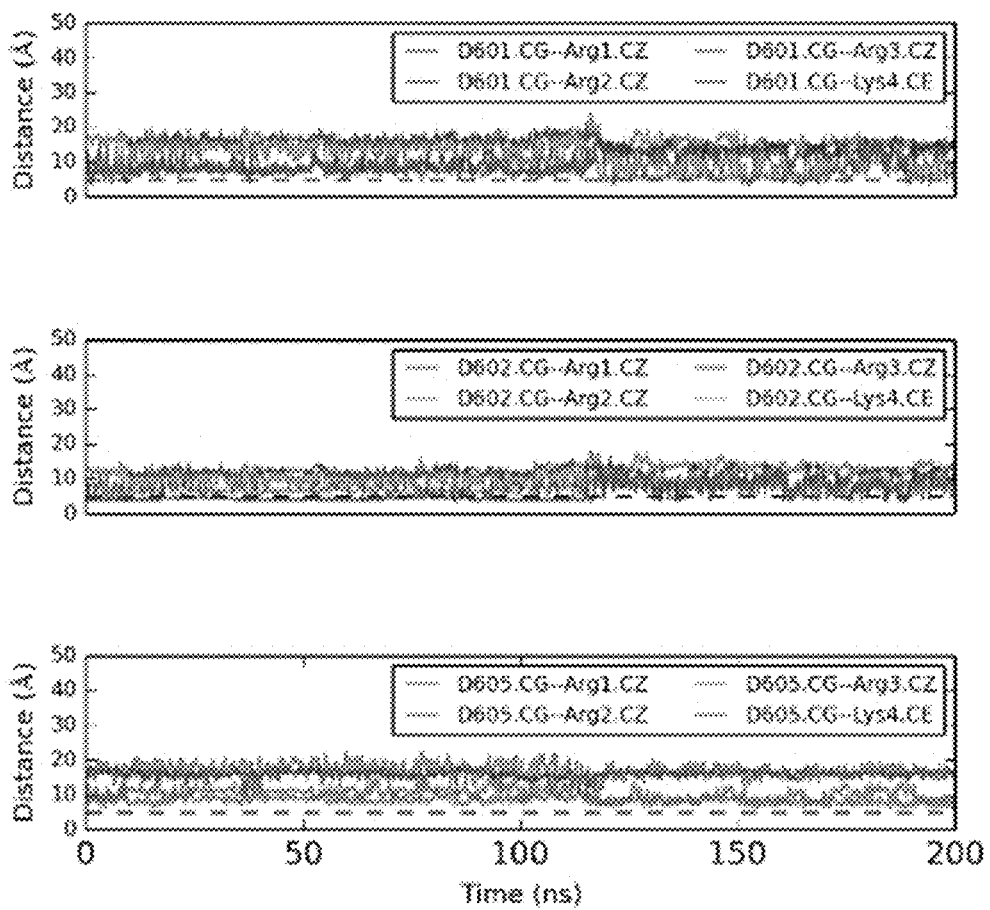
Figure 12F:
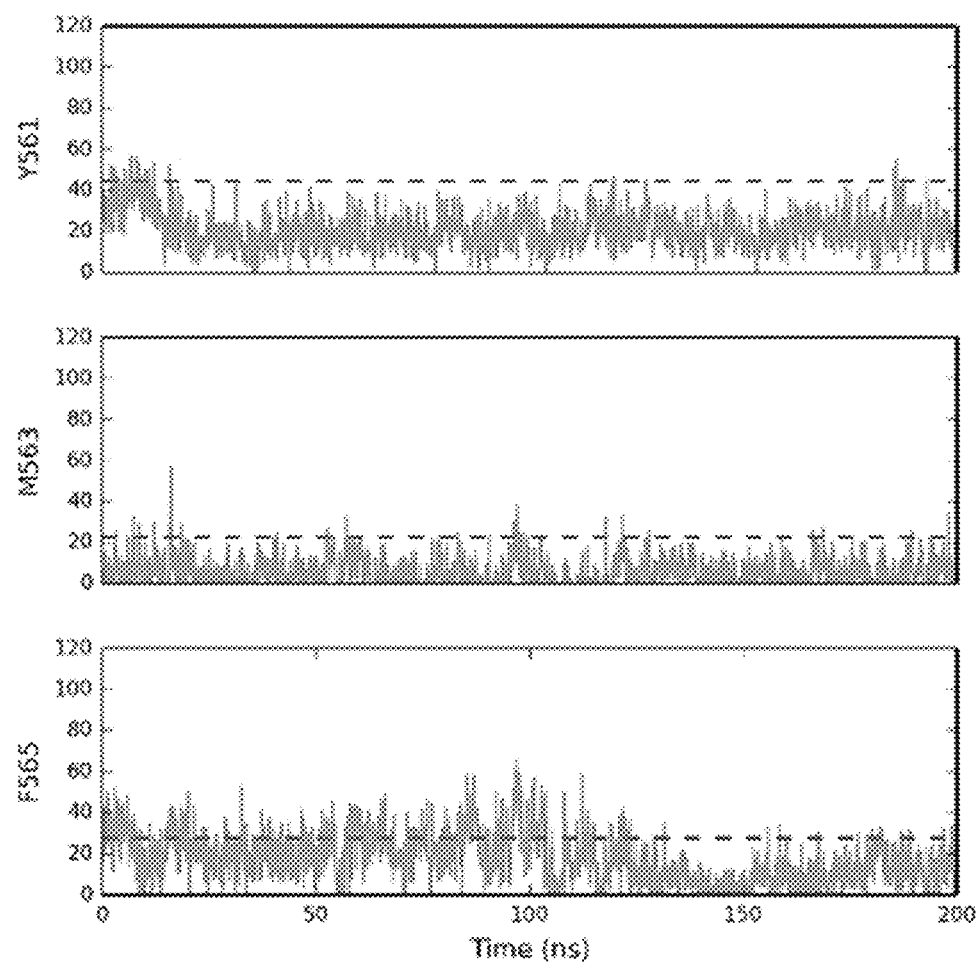
Figure 13A:
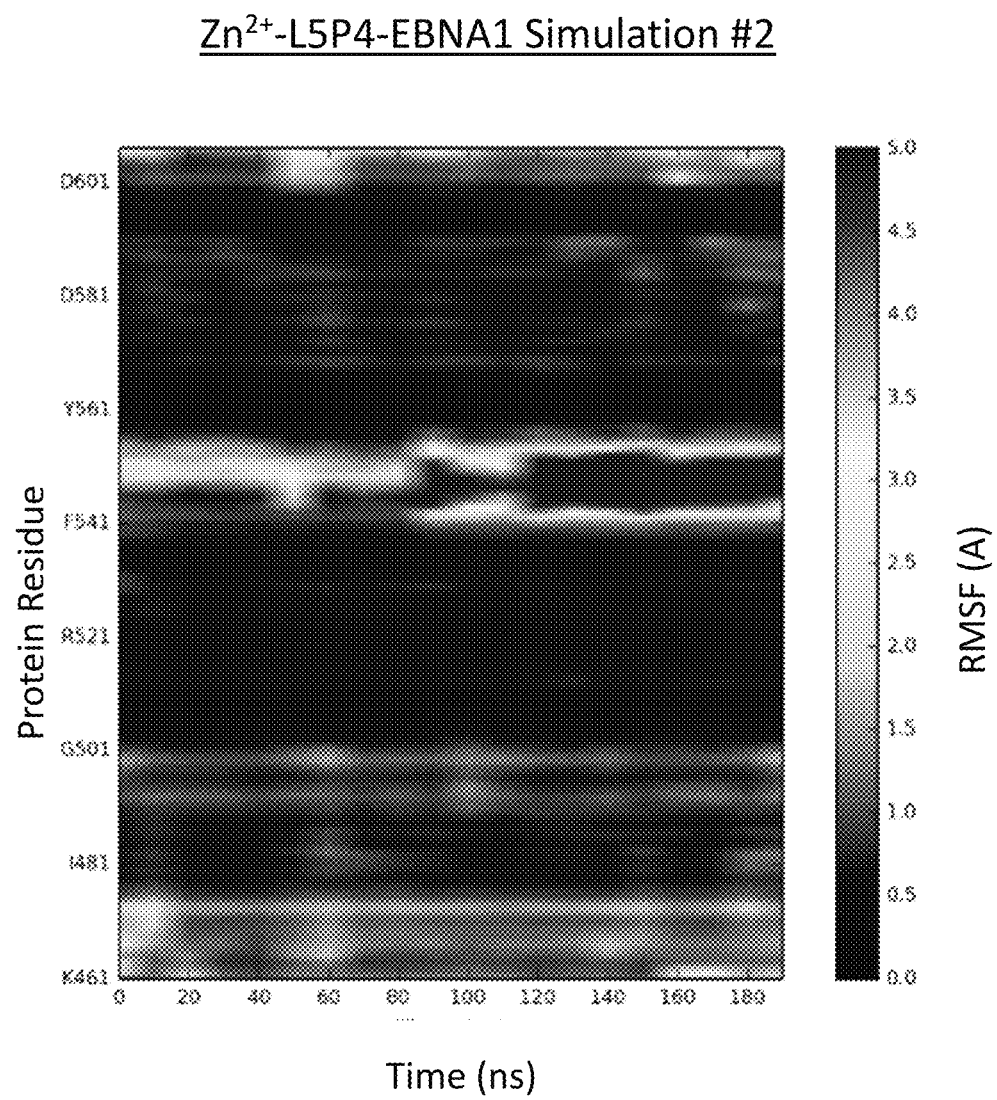
Figure 13B:
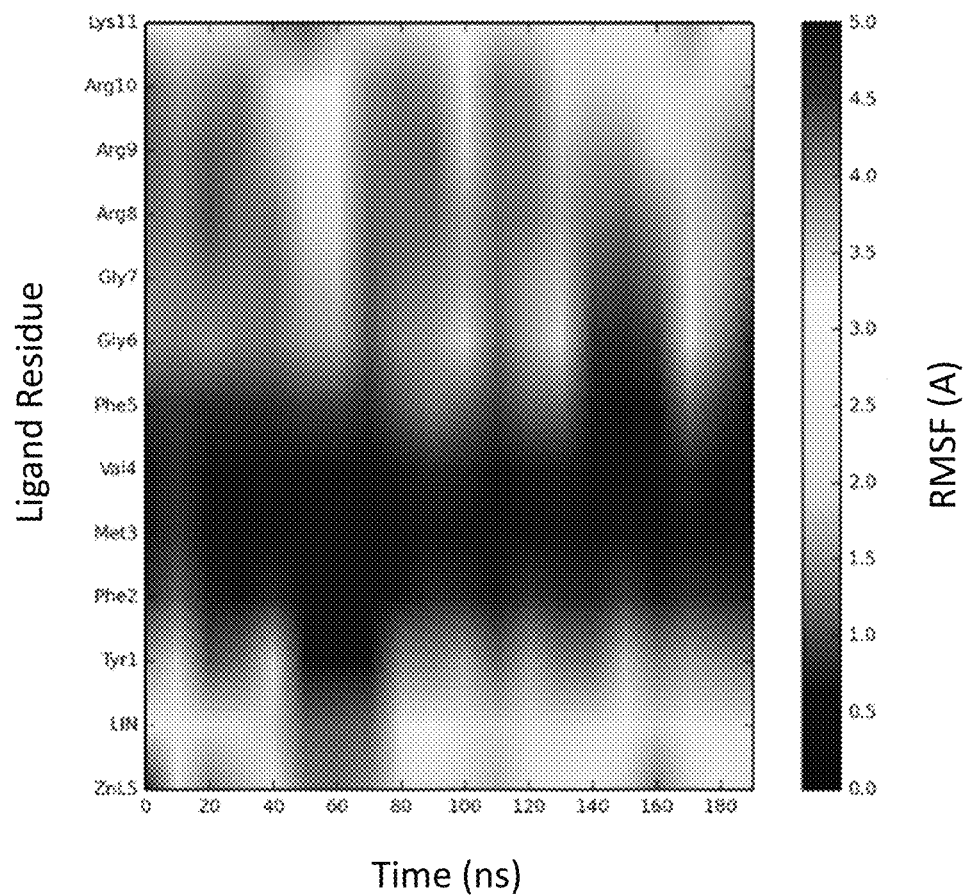
Figure 13C:
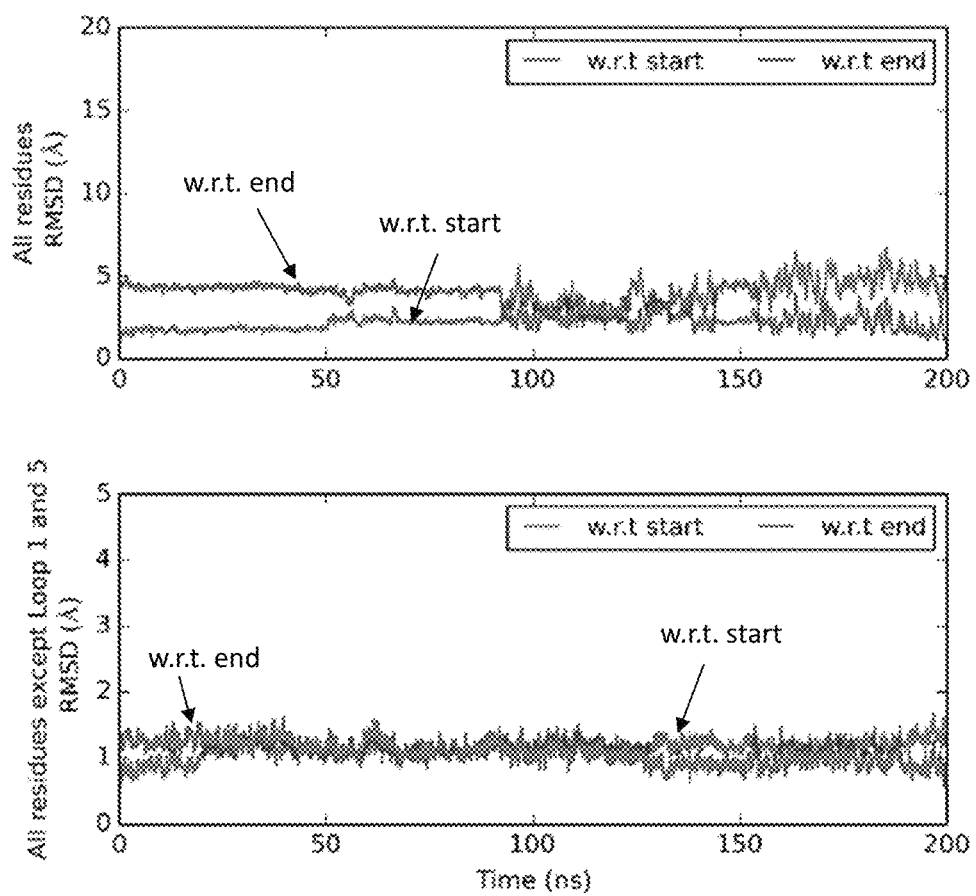
Figure 13D:
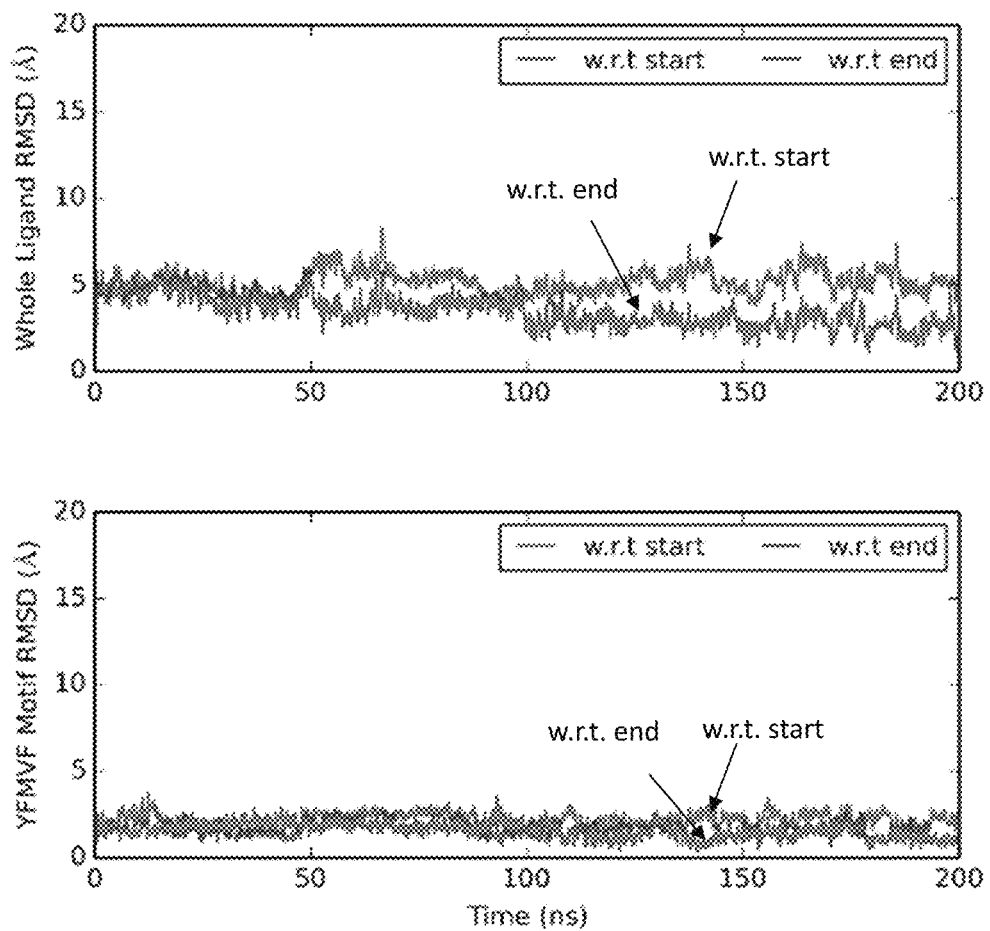
Figure 13E:
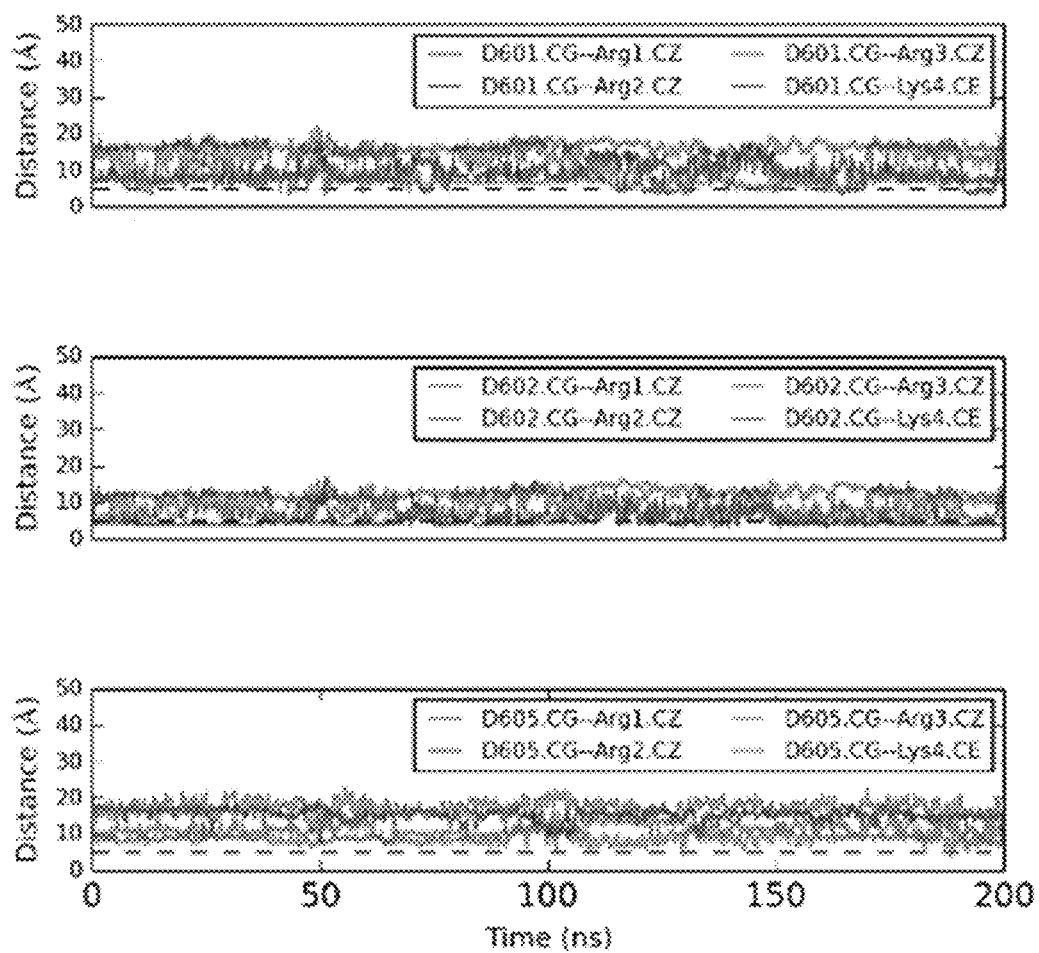
Figure 13F:
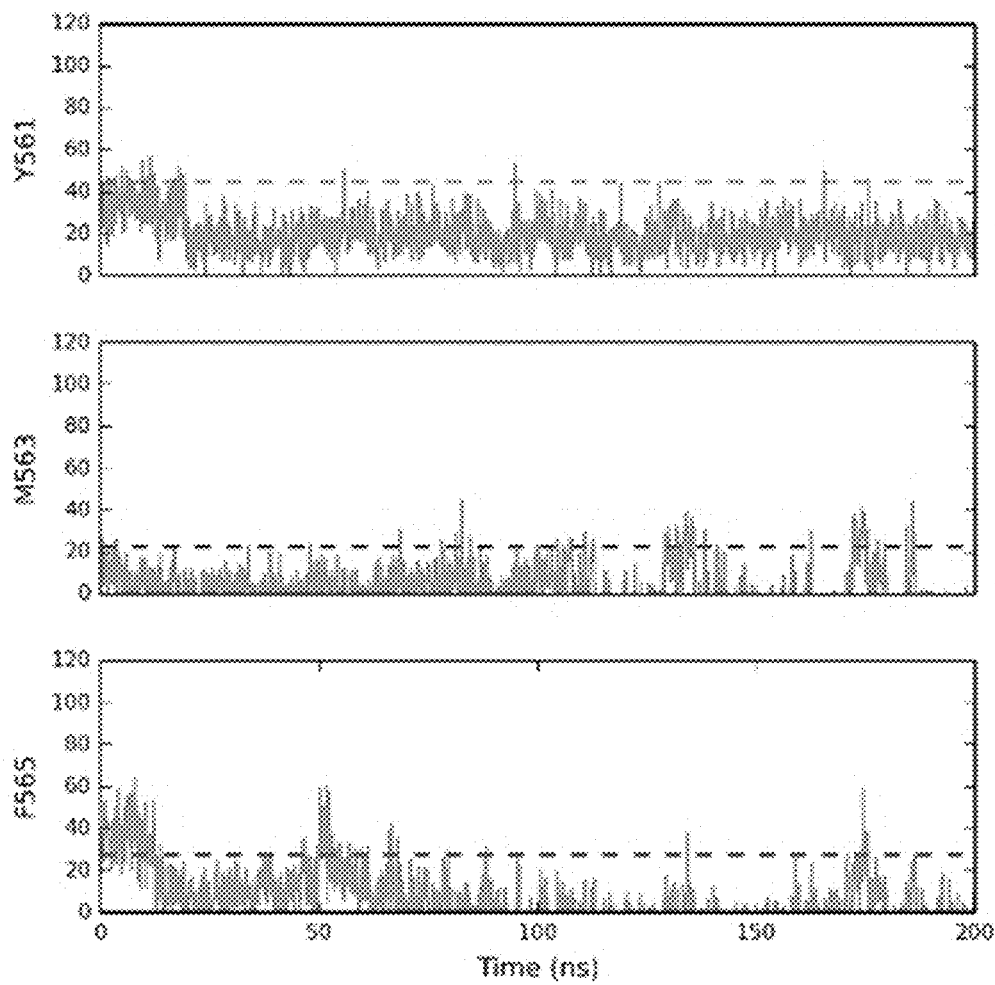

The 3D models of the zinc-chelator and responsive fluorophore $ZRL_5$ in both $Zn^{2+}$-free and $Zn^{2+}$-coordinated scenarios were built and optimized with molecular mechanics and a conformational searching tool LowModeMD. The $Zn^{2+}$-coordinated DPA chelator fragment from the final optimized $Zn^{2+}$—$ZRL_5$ superposed very well with the crystal structure of a highly similar compound $Zn^{2+}$—$ZTF^{11}$ (FIG. 8), suggesting that the two configurations converged at the global energy minimum. Considering the five-coordinate complex formed in the $Zn^{2+}$—ZTF crystal structure (one coordination site is occupied by the solvent molecule) and the high structural similarity between $ZRL_5$ and ZTF, models of DMSO—$Zn^{2+}$—$ZRL_5$ and $H_2O$—$Zn^{2+}$—$ZRL_5$ were constructed, with the solvent O atom acting as an electron donor (FIG. 9).

Figure 6B:
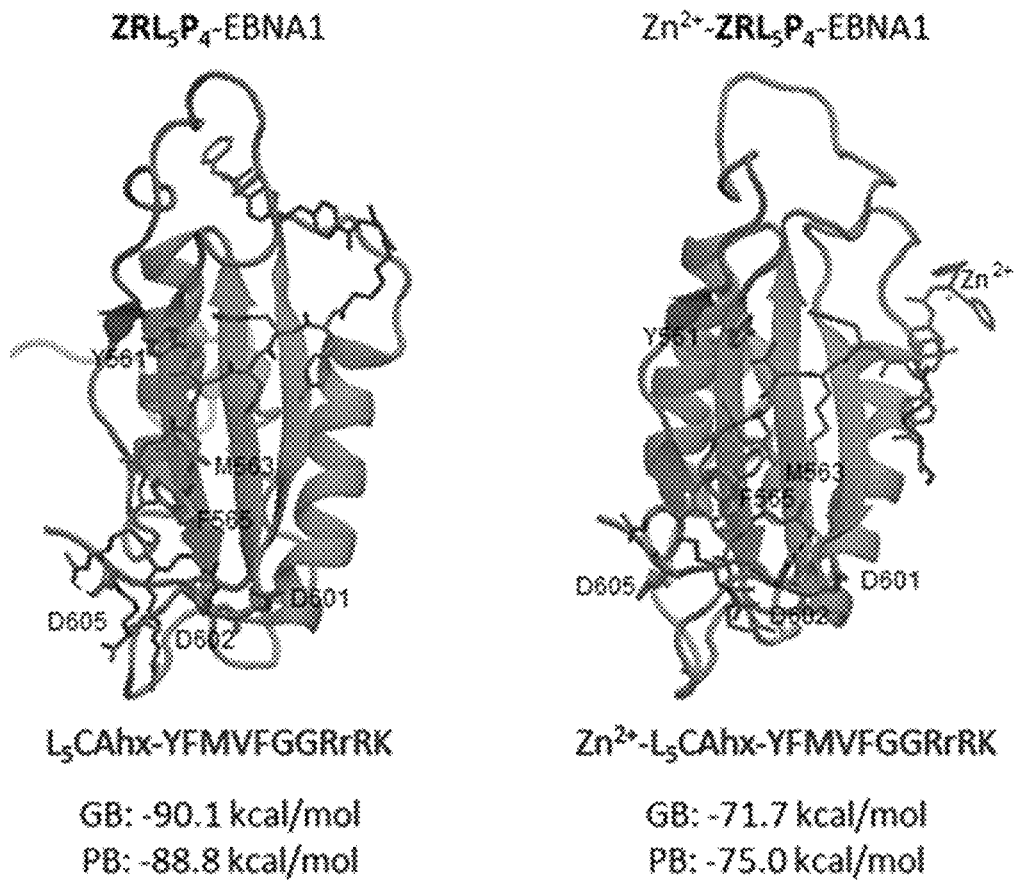
FIG. 6B shows the binding energy of $ZRL_5P_4$ and $Zn^{2+}$-$ZRL_5P_4$ to the putative EBNA1 DBD monomer calculated via MMPBSA.
Figure 7A:
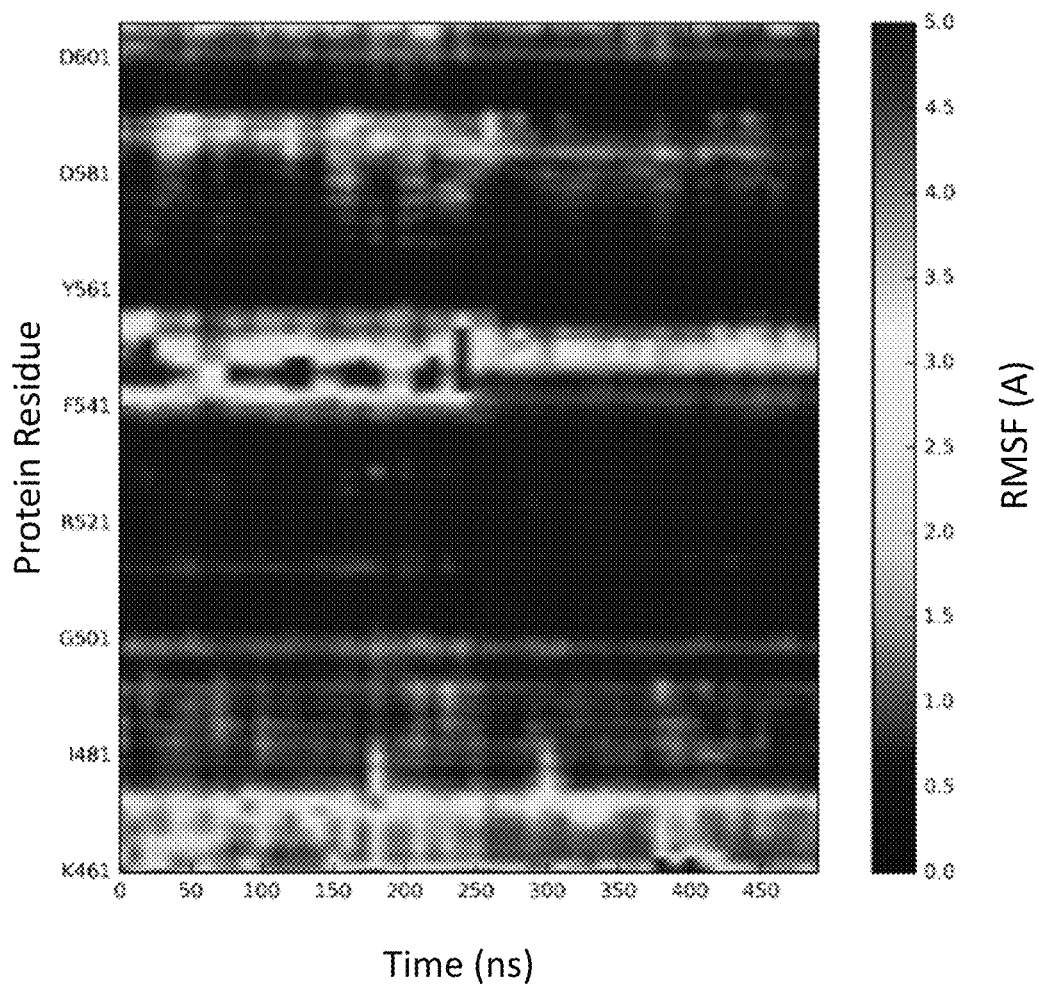
FIG. 7(A-F) shows 500 ns NPT simulation of P4-EBNA1 complex model (#9), the complex model is chosen from flexible peptide docking. (A) Root-mean-square fluctuation (RMSF) of the putative EBNA1 DBD monomer. (B) RMSF of $P_4$. (C) RMSD of main-chain atoms from EBNA1 DBD with regard to (w.r.t) the initial and end structure. (D) RMSD of main-chain atoms from $P_4$ (YFMVF, SEQ ID NO: 2) with regard to the initial and end structure. (E) The salt-bridging between RrRK motif and the acid residues in the C-terminus EBNA1 DBD. (F) The hydrophobic packing between YFMVF (SEQ ID NO:2) motif and the dimeric interface of EBNA1 DBD.
Figure 7B:
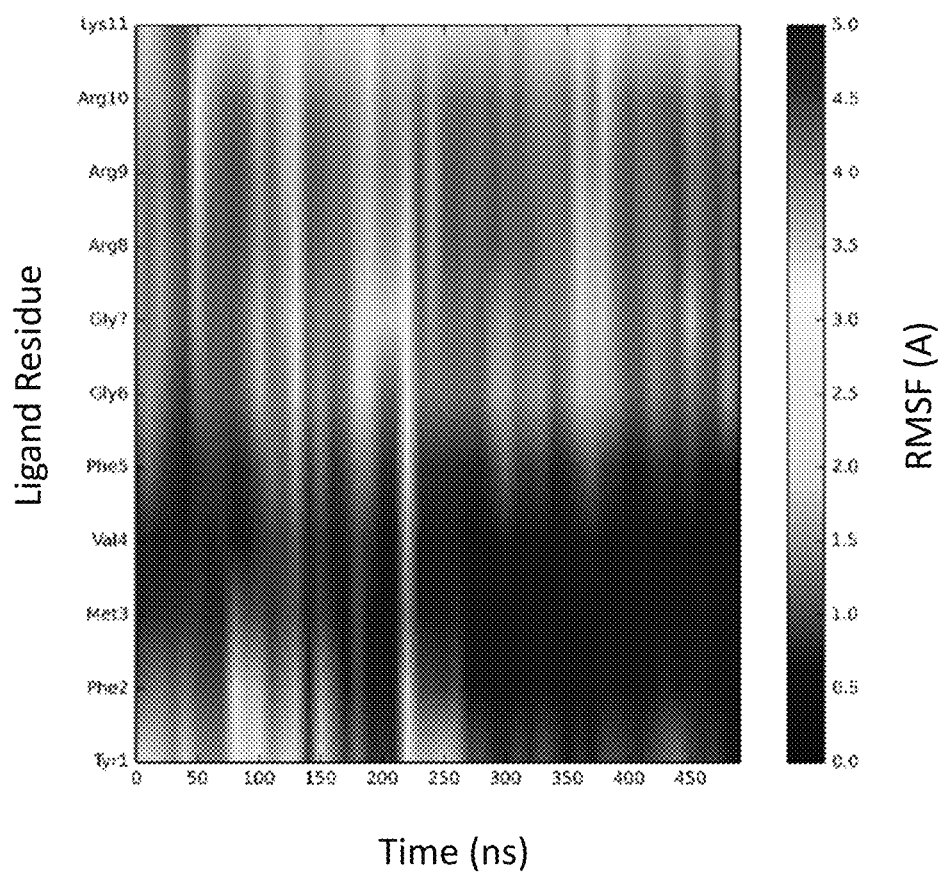
Figure 7C:
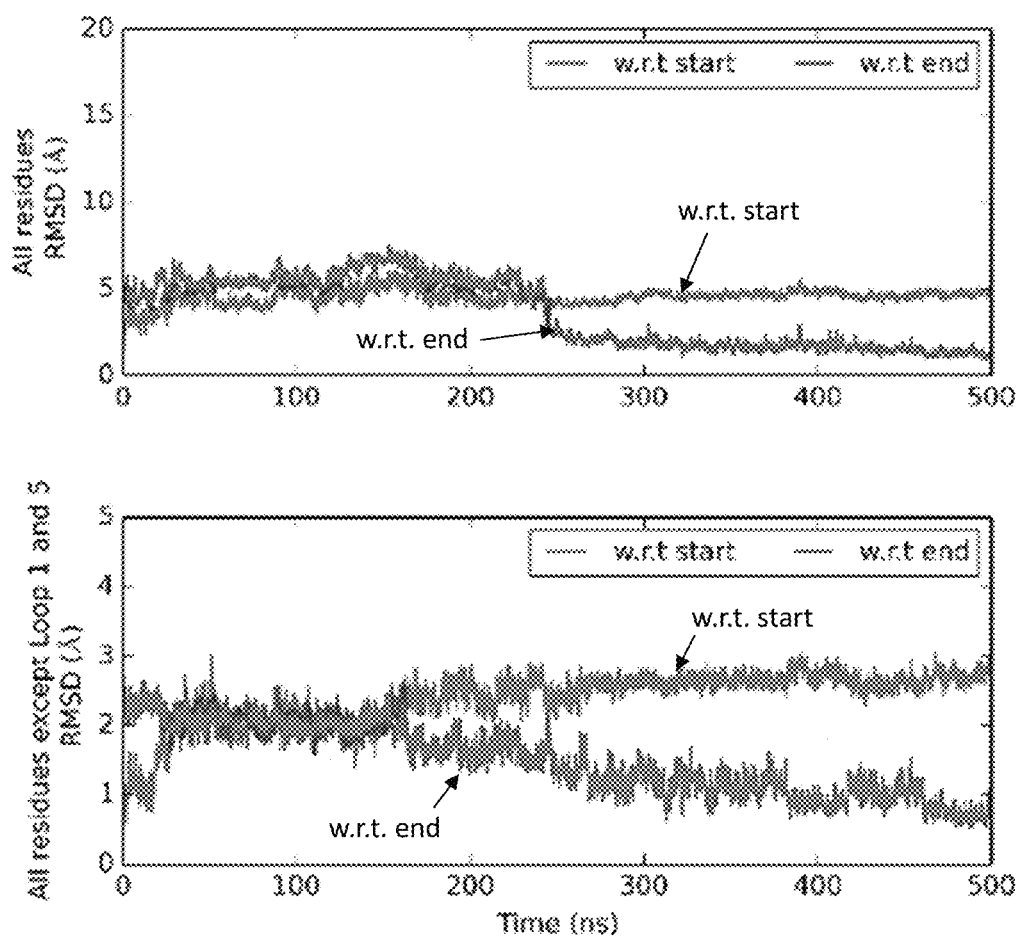
Figure 7D:
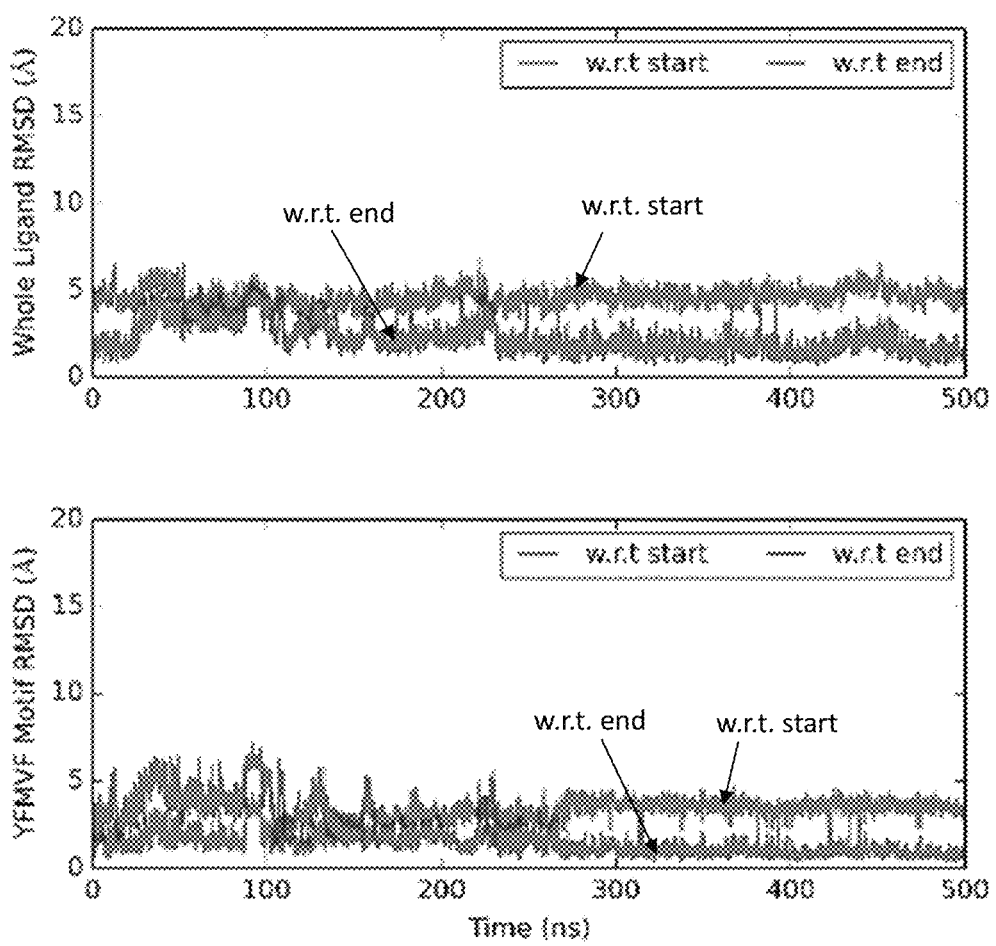
Figure 7E:
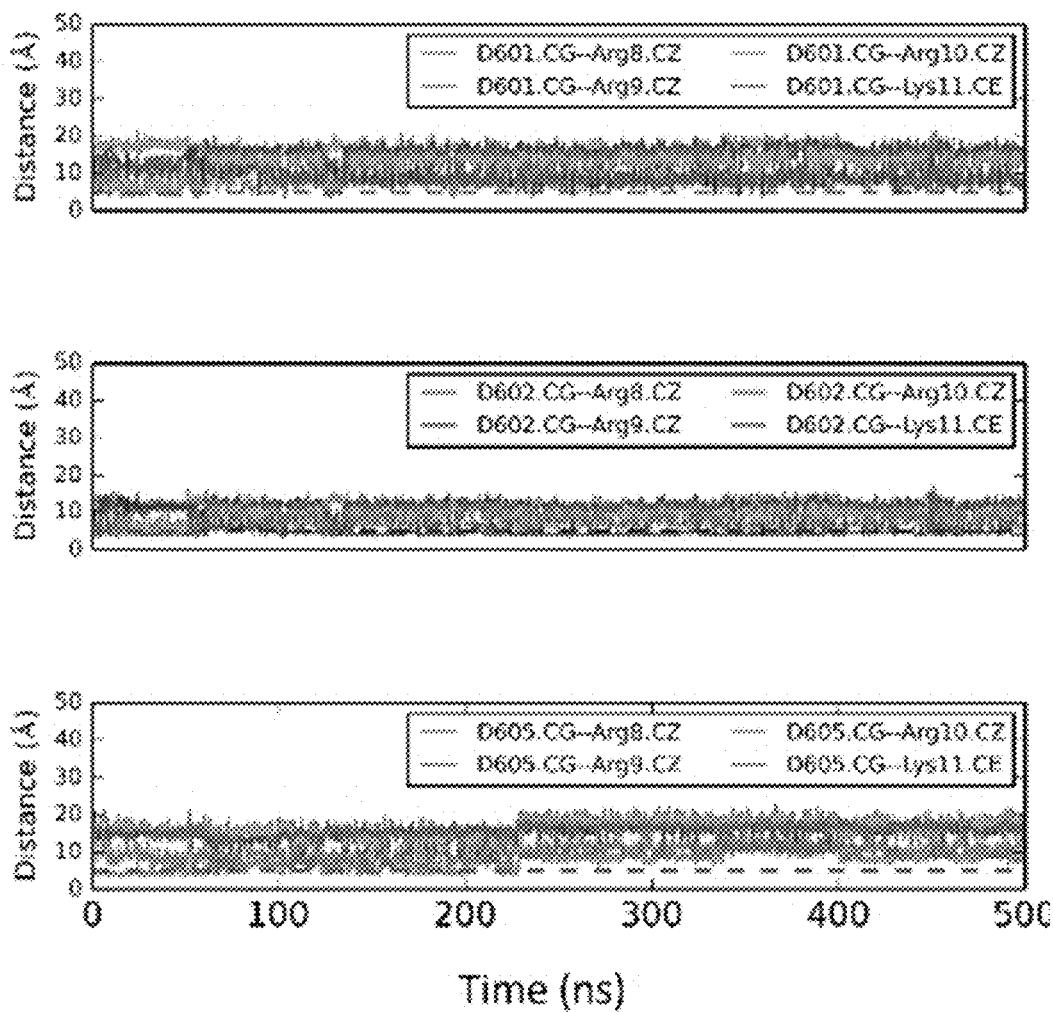
Figure 7F:
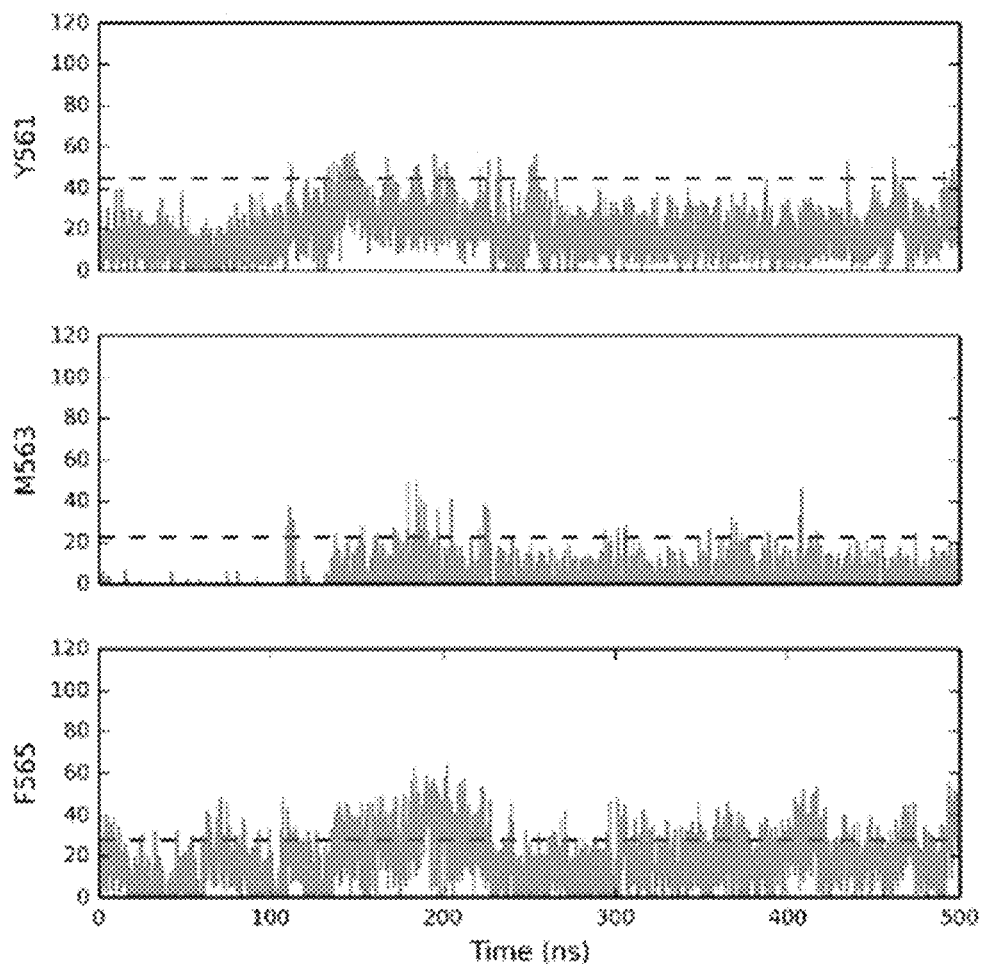
Figure 8A:
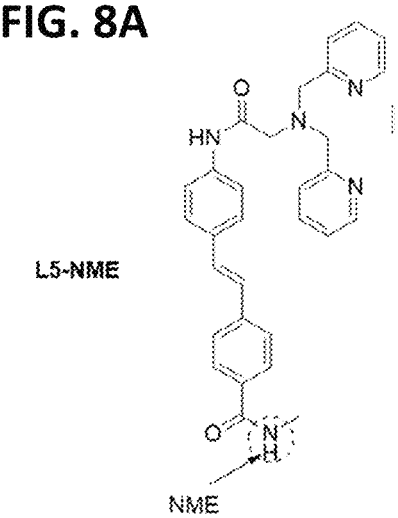
FIG. 8(A-E) shows the putative 3D structures of $ZRL_5$-NME and $Zn^{2+}$-$ZRL_5$-NME resulted from molecular mechanics calculation. (A) 2D structure of $ZRL_5$-NME. (B) The calculated 3D structure of $ZRL_5$-NME. (C) 2D structure of $Zn^{2+}$-$ZRL_5$-NME. (D) The calculated 3D structure of $Zn^{2+}$-$ZRL_5$-NME. (E) The superposition of the calculated $Zn^{2+}$-$ZRL_5$-NME 3D structure onto the crystal structure of ZTF-$Zn^{2+}$, a highly similar compound reported previously.
Figure 8B:
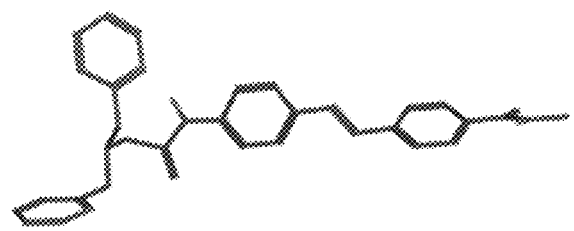
Figure 8C:
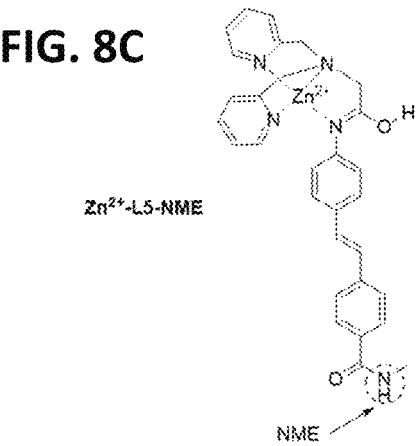
Figure 8D:
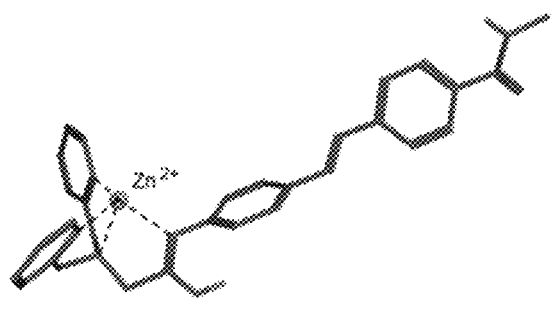
Figure 8E:
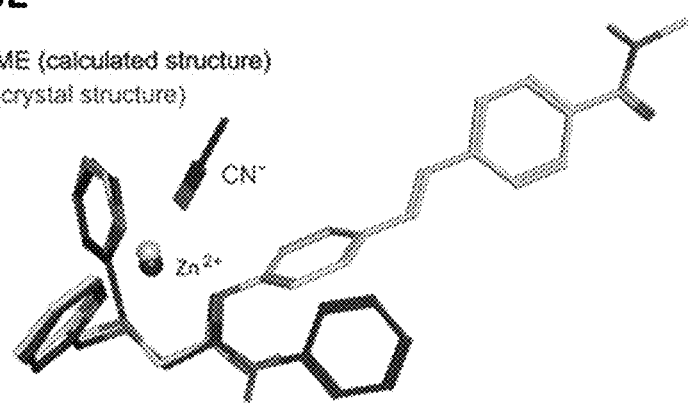

The tertiary interaction models of the $Zn^{2+}$-bound and -unbound $ZRL_5P_4$ with EBNA1 ($ZRL_5P_4$—EBNA1 and $Zn^{2+}$—$ZRL_5P_4$-EBNA1 complexes) were constructed based on the aforementioned $P_4$—EBNA1 DBD and $ZRL_5$/$Zn^{2+}$—$ZRL_5$ models. The two interaction models were then subjected to 200 ns MD simulations for structure optimization and binding energy calculations (FIG. 10-13). Both interaction models have demonstrated stable probe-protein interactions, and the final optimized models are shown in FIG. 7B 6B (simulation #1, both complexes were simulated twice, and the second simulation is shown in FIGS. 11, 13 and 14). The featured interaction model of the $P_4$-EBNA1 complex with the hydrophobic interaction mediated by YFMVF (SEQ ID NO:2) and the salt bridge formed by RrRK, are well-conserved. The results indicate that the presence of $Zn^{2+}$ did not affect $ZRL_5P_4$ to interact with the EBNA1 DBD, this observation is further supported by the calculated binding energies using MMPBSA (FIG. 6B, FIG. 14 and Table 1).

TABLE 1

The calculated binding affinity between $ZRL_5P_4$/$Zn^{2+}$—$ZRL_5P_4$ and EBNA1 DBD.

| System | Simulation | GB (kcal/mol) | PB (kcal/mol) |
|---|---|---|---|
| $ZRL_5P_4$—EBNA1 DBD | #1 | −90.1365 ± 8.5697 | −88.8280 ± 8.7654 |
|  | #2 | −79.9369 ± 11.5724 | −78.9043 ± 13.2484 |
| $Zn^{2+}$—$ZRL_5P_4$—EBNA1 DBD | #1 | −71.6652 ± 9.1082 | −74.9505 ± 10.8770 |
|  | #2 | −69.1021 ± 12.3023 | −74.3209 ± 13.8954 |

Dual-Responsive Emission by the Three New EBNA1 Probes when Binding to $Zn^{2+}$ and EBNA1.

Figure 2A:
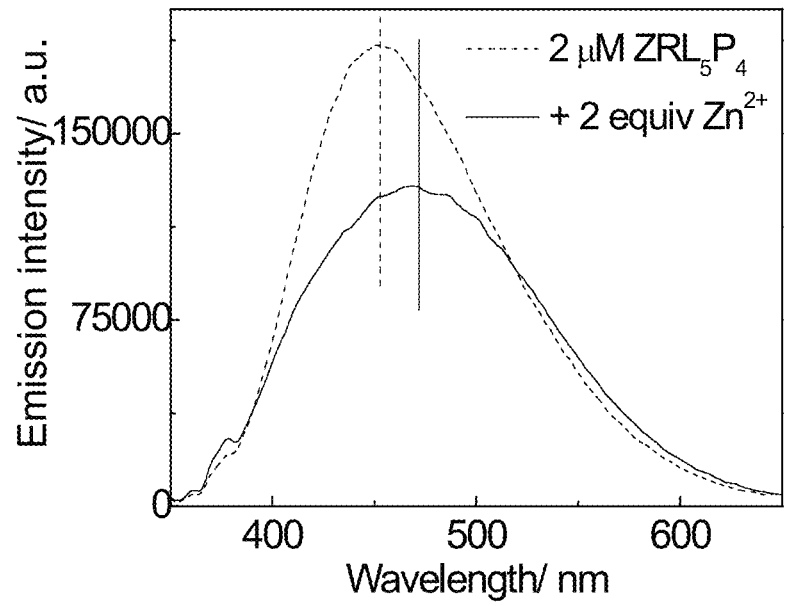
FIG. 2A shows fluorescence spectral changes of $ZRL_5P_4$ (2 μM; excitation at 337 nm) in the presence of $Zn^{2+}$ in aqueous solution ($CH_3CN$/0.05 M HEPES, pH 7.4=50:50).
Figure 2B:
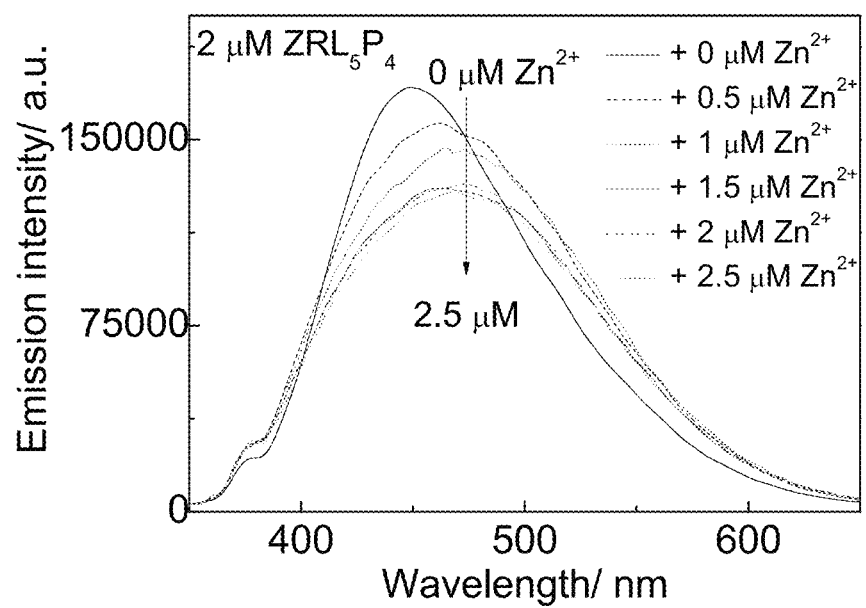
FIG. 2B shows fluorescence spectral changes of $ZRL_5P_4$ (2 μM; excitation at 337 nm) upon addition of $Zn^{2+}$ in aqueous solution ($CH_3CN$/0.05 M HEPES, pH 7.4=50:50).
Figure 3A:
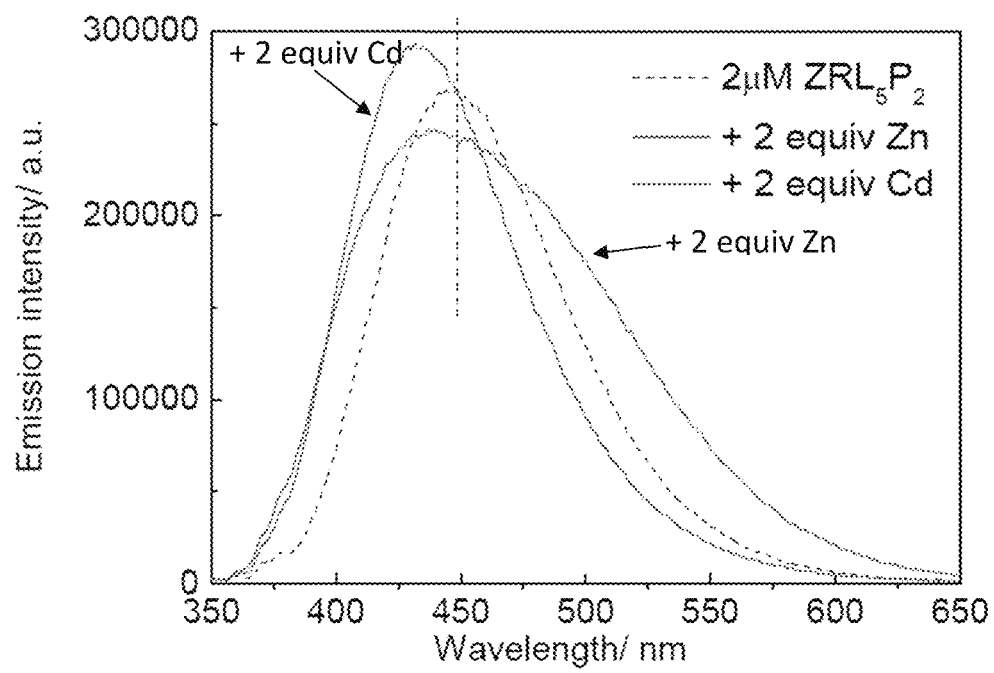
FIG. 3A shows fluorescence spectral changes of $ZRL_5P_2$ (2 μM; excitation at 337 nm) in the presence of $Zn^{2+}$ and $Cd^{2+}$ in aqueous solution ($CH_3CN$/0.05 M HEPES, pH 7.4=50:50).
Figure 3B:
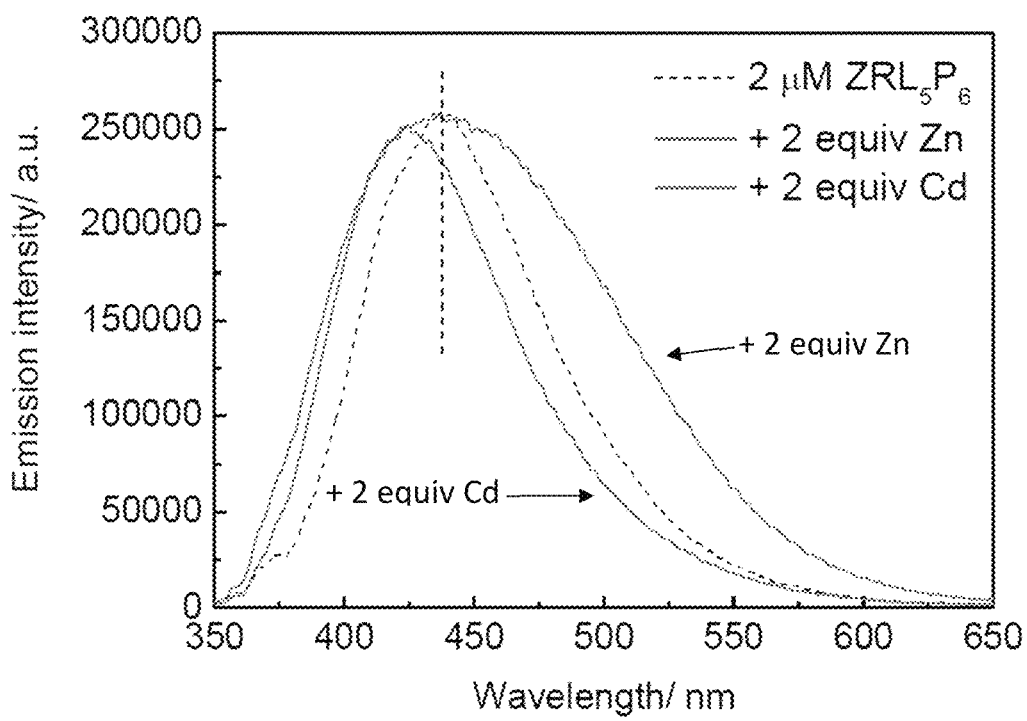
FIG. 3B shows fluorescence spectral changes of $ZRL_5P_6$ (2 μM; excitation at 337 nm) in the presence of $Zn^{2+}$ and $Cd^{2+}$ in aqueous solution ($CH_3CN$/0.05 M HEPES, pH 7.4=50:50).
Figure 4A:
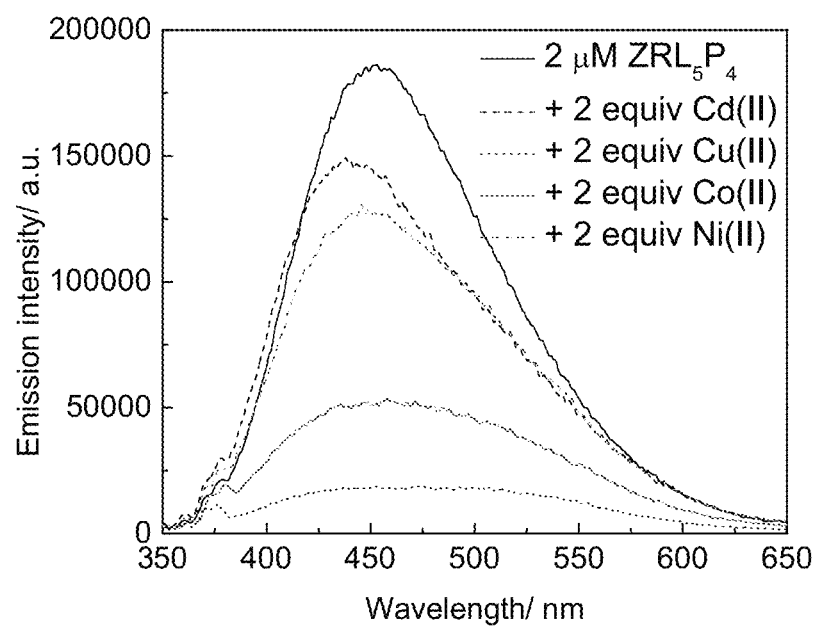
FIG. 4A shows fluorescence spectral changes of $ZRL_5P_4$ (2 μM; excitation at 337 nm) in the presence of $Cd^{2+}$, $Cu^{2+}$, $Co^{2+}$, $Ni^{2+}$ in aqueous solution ($CH_3CN$/0.05 M HEPES, pH 7.4=50:50).
Figure 4B:
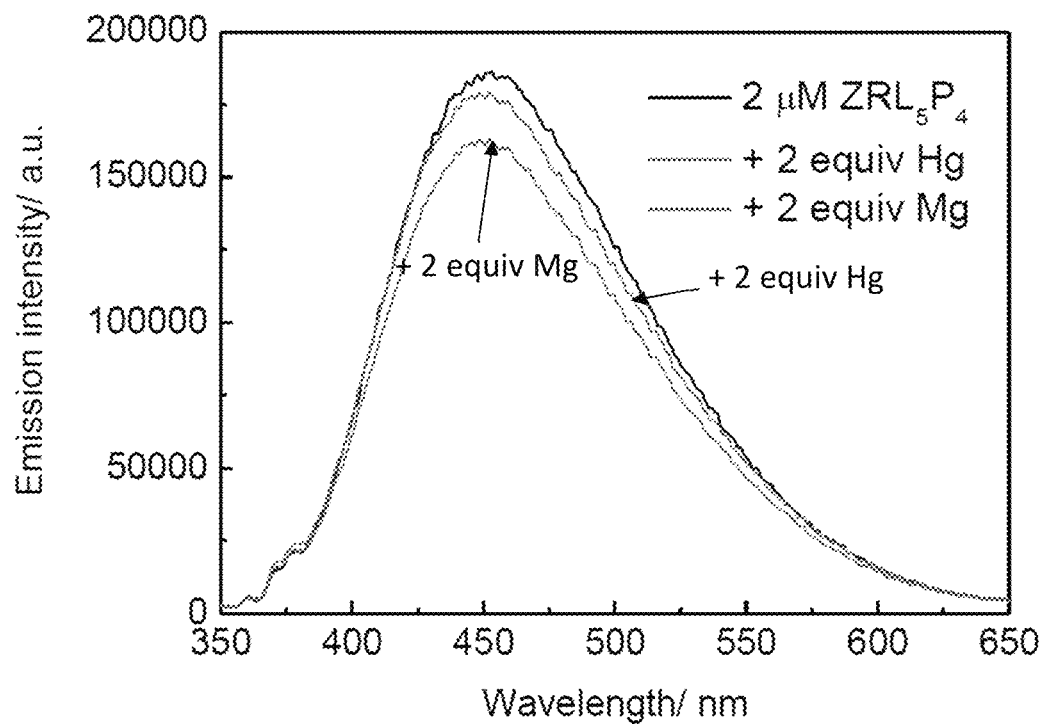
FIG. 4B shows fluorescence spectral changes of $ZRL_5P_4$ (2 μM; excitation at 337 nm) in the presence of $Hg^{2+}$ and $Mg^{2+}$ in aqueous solution ($CH_3CN$/0.05 M HEPES, pH 7.4=50:50).

The fluorescence spectral changes of the three new EBNA1 probes ($ZRL_5P_2$, $ZRL_5P_4$, $ZRL_5P_6$) in the presence of 2 equiv. of $Zn^{2+}$ in aqueous solution [$CH_3CN$/0.05 M HEPES (pH 7.4), 50:50] were firstly measured (FIG. 2A and FIG. 3A-B; all of the metal salts used in this work were perchlorates, which should be used with caution). Only $ZRL_5P_4$ demonstrated a 21 nm redshifted emission (451 to 472 nm) upon addition of $Zn^{2+}$, while the other two probes either showed a slightly blue shifted emission ($ZRL_5P_2$, 448 to 445 nm) or their maximum emission wavelength was unchanged ($ZRL_5P_6$, 438 nm). So, the detailed kinetics of the redshifted emission by $ZRL_5P_4$ was focused on. The luminescence of $ZRL_5P_4$ upon titration with various concentrations of $Zn^{2+}$ to check the binding stoichiometry was investigated. A gradually redshifted emission with a concomitant decrease in the emission intensity was observed, and this trend ceased if 1 equiv. of $Zn^{2+}$ was added, indicating that the $ZRL_5P_4$—$Zn^{2+}$ complex had 1:1 stoichiometry (FIG. 2B). Additionally, the selectivity of $ZRL_5P_4$ towards $Zn^{2+}$ over various heavy and transition metal ions was also measured (FIG. 4A-B). The results show that $Cd^{2+}$, $Cu^{2+}$, $Co^{2+}$, and $Ni^{2+}$ (FIG. 4A) differentially decreased the emission intensity with $Cd^{2+}$ displayed a 10 nm blue shifted emission, and $Hg^{2+}$ and $Mg^{2+}$ (FIG. 4B) barely affected the $ZRL_5P_4$ emission; none of these results indicate that competitive responsive emission was induced by $Zn^{2+}$.

Figure 2C:
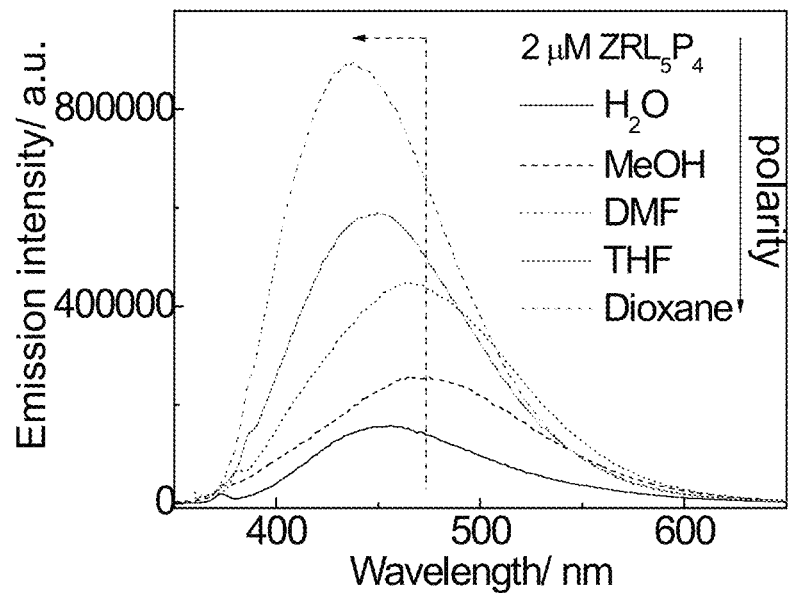
FIG. 2C shows solvation study of $ZRL_5P_4$ (2 μM; excitation at 337 nm) to check whether the ICT-state emission was presented by the probe.
Figure 2D:
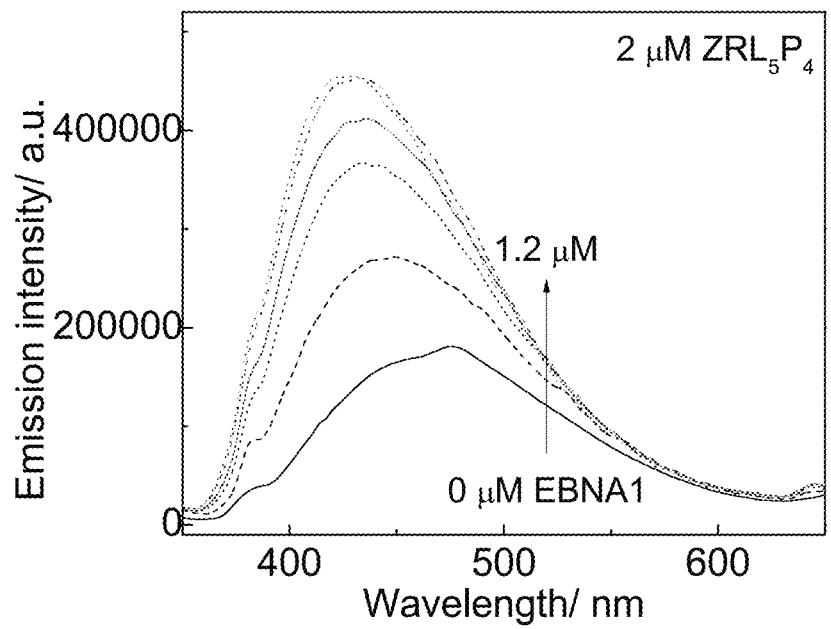
FIG. 2D shows fluorescence spectral changes of $ZRL_5P_4$ (2 μM; excitation at 337 nm) upon addition of EBNA1.
Figure 2E:
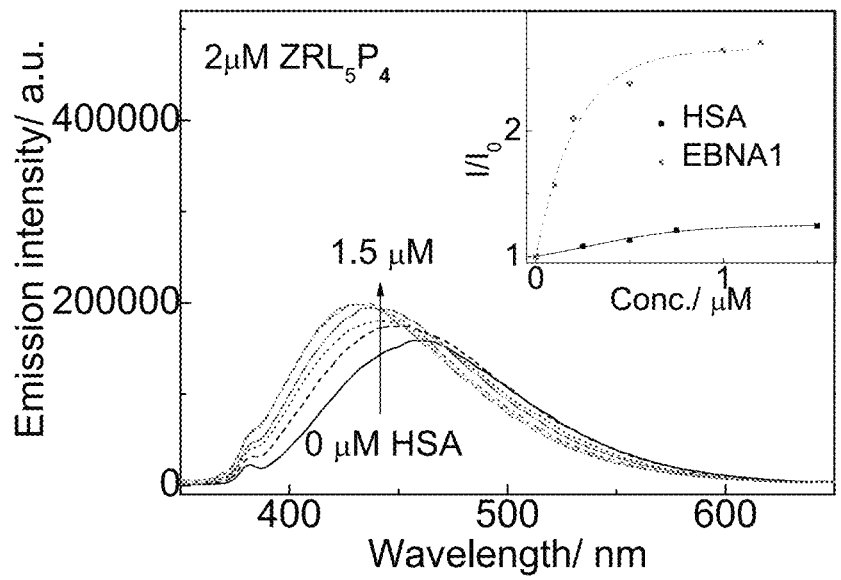
FIG. 2E shows fluorescence spectral changes of $ZRL_5P_4$ (2 μM; excitation at 337 nm) upon addition of human serum albumin (HSA). The selectivity of $ZRL_5P_4$ to EBNA1 over HSA as shown by the fluorescence intensity ratio before and after the addition of the protein.
Figure 2F:
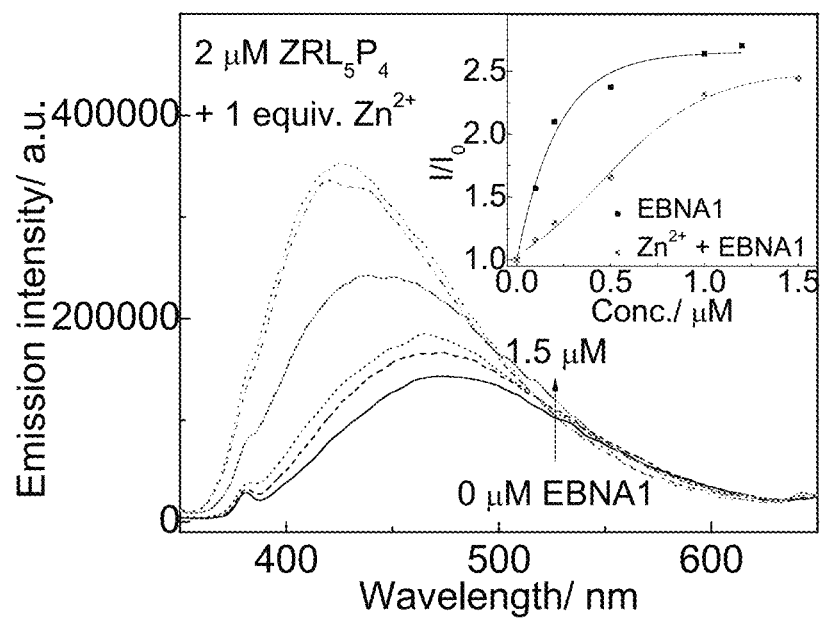
FIG. 2F shows fluorescence spectral changes of $ZRL_5P_4$ upon addition of EBNA1 in the presence of 1 equiv. $Zn^{2+}$. Inset figure shows fluorescence intensity performance in the presence and absence of $Zn^{2+}$ upon the addition of EBNA1.
Figure 5A:
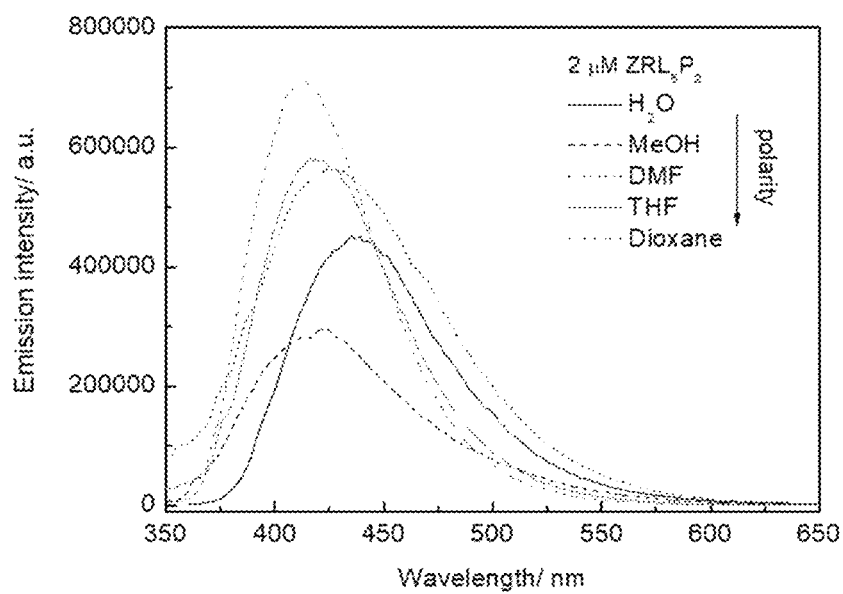
FIG. 5A shows solvation study of $ZRL_5P_2$ with a decrease of solvent polarity.
Figure 5B:
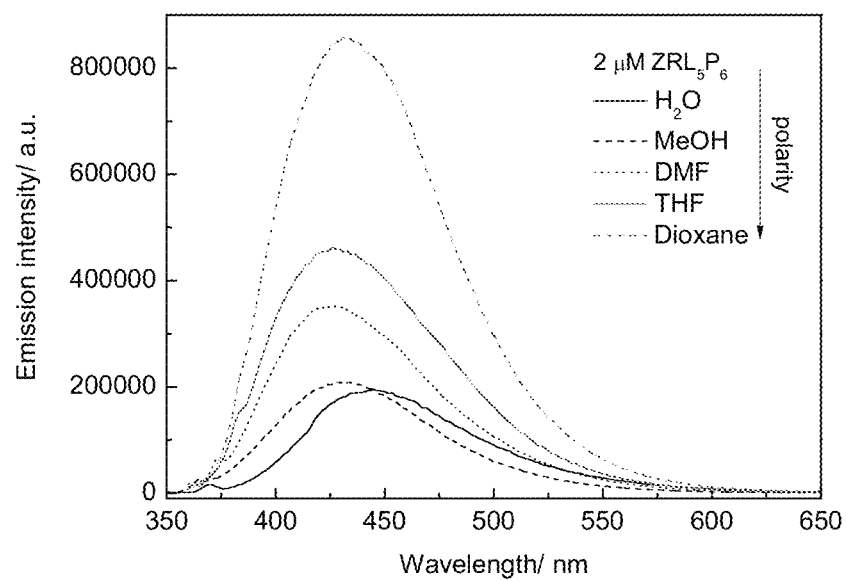
FIG. 5B shows solvation study of $ZRL_5P_6$ with a decrease of solvent polarity.

The EBNA1-binding activity of $ZRL_5P_2$, $ZRL_5P_4$, and $ZRL_5P_6$ were next investigated. Before performing the assay, a solvation study was performed to determine the intramolecular charge transfer (ICT) characteristics of each probe. The responsive signal emitted by the fluorophore of the EBNA1 probes when binding to EBNA1 was based on the principle of the ICT mechanism. It has been well-documented that ICT-mediated emission is strongly solvent-dependent; that is, emission is enhanced and blue shifted with the decrease of solvent polarity (FIG. 2C). As shown in FIG. 2A and FIG. 5A-B, $ZRL_5P_4$ demonstrated the best ICT characteristics, whereas $ZRL_5P_6$ also showed enhancement of emission intensity but no blue shifted emission. Thus, $ZRL_5P_4$ represented the best candidate probe and was assayed for its activity towards the EBNA1 DBD protein. It was found that the addition of 1.2 μM EBNA1 to $ZRL_5P_4$ caused a 2.7-fold emission enhancement, which was blue shifted by 39 nm (466 to 427 nm) (FIG. 2D). The irrelevant human serum albumin (HSA) was used as a negative control target protein, and the addition of HSA to $ZRL_5P_4$ showed only a 1.2-fold increase of its emission intensity (FIG. 2E). FIG. 2E (inset) clearly shows that the binding of $ZRL_5P_4$ was highly selective for EBNA1 over HSA. In addition, the fluorescence response of $ZRL_5P_4$ to EBNA1 was also measured in the presence of $Zn^{2+}$ (FIG. 2F). A 2.4-fold emission enhancement with a 51 nm blueshift (477 nm to 426 nm) was observed, demonstrating that the presence of $Zn^{2+}$ did not affect the $ZRL_5P_4$-EBNA1 DBD binding, as reflected by the same order of enhanced emission without $Zn^{2+}$ (FIG. 2D). This observation was supported by the MD simulation results (FIG. 6B). Moreover, this observation also indicates that the spectral response in the presence of $Zn^{2+}$ will result in a larger blueshift with a slight emission enhancement of $ZRL_5P_4$.

Confirmation of the Interaction of $ZRL_5P_4$ with Zinc(II) by Nuclear Magnetic Resonance (NMR) Study.

Figure 15A:
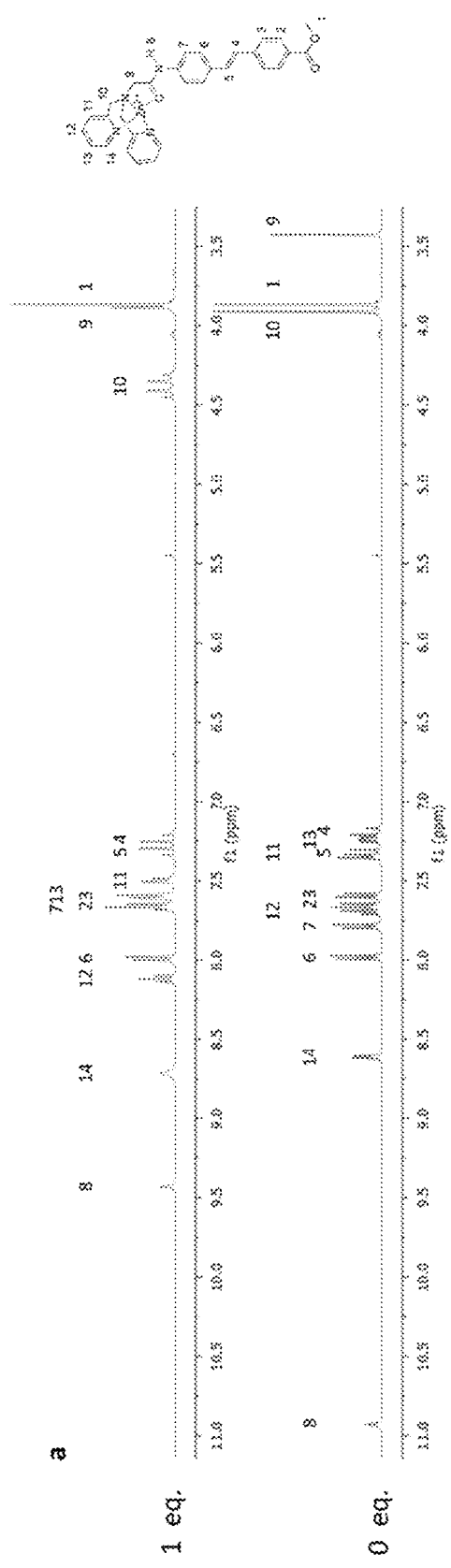
Figure 15B:
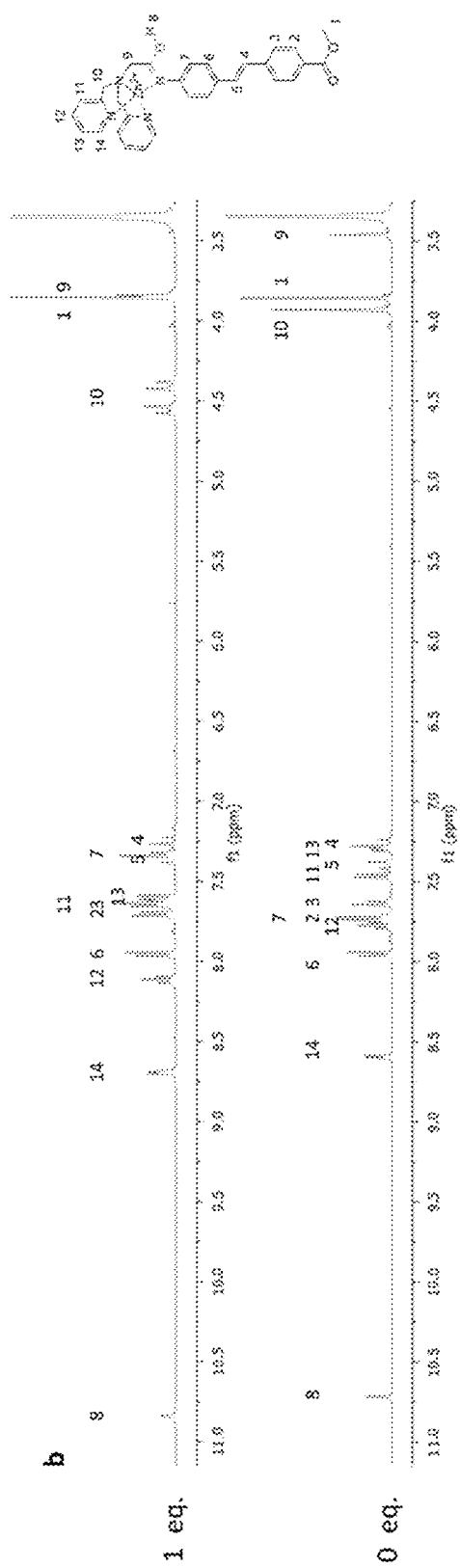

To characterize the mechanism of how $ZRL_5P_4$ interacts with zinc(II), $^1H$ NMR titration experiments of $ZRL_5P_4$ with and without 1 equiv. zinc(II) were conducted. As reported by a previous study, an amide-imidic acid tautomer binding mode was adopted by this zinc chelator in different solvents; in detail, the zinc(II) chelate complex is an amide tautomer in $CH_3CN$ whereas it is an imidic tautomer in DMSO. To determine whether $ZRL_5P_4$ can interact with zinc(II) in a similar way, the $^1H$ NMR spectroscopy of compound 5 (the precursor of $ZRL_5$) with/without zinc(II) in $CD_3CN$ and DMSO-$d_6$ was conducted. Compound 5 was used as a substitute of $ZRL_5P_4$ in this study because the presence of the peptide moiety will make it hard to assign peaks in the region of interest. Consistent with the previous work, proton 8 showed a large upfield shift from 10.93 to 9.43 ppm in $CD_3CN$, but was shifted downfield from 10.72 to 10.84 ppm in DMSO-$d_6$ (FIG. 15A-B). This finding confirmed the two binding modes of $ZRL_5P_4$ in MeCN and DMSO, thereby it can be inferred that the zinc(II)-triggered amide-tautomerization, which has been described in the previous study, will also occur in $ZRL_5P_4$. $ZRL_5P_4$ diminishes EBNA1 homodimerization and transcription activated by EBNA1. The ability of $ZRL_5P_4$ to prevent EBNA1 dimerization in the absence and presence of $Zn^{2+}$ was assayed and compared with $L_2P_4$. Since $Zn^{2+}$ mediates zinc finger formation at EBNA1 UR1 (a.a. 64-89) and $ZRL_5P_4$ strongly binds $Zn^{2+}$, the full-length EBNA1, rather than EBNA1 DBD, was employed in this assay. Without probe treatments, the presence of $Zn^{2+}$ slightly increased EBNA1 dimerization (buffer, – or $+Zn^{2+}$), confirming the role of $Zn^{2+}$ in EBNA1 dimerization. $ZRL_5P_4$ decreased EBNA1 dimer to a similar level as shown by $L_2P_4$ since in the absence of $Zn^{2+}$ dimerization inhibition comes only from the peptide moiety (left part in FIG. 18A-B). However, the two probes behaved distinctly in the presence of $Zn^{2+}$, $ZRL_5P_4$ demonstrated a much stronger dimerization inhibition than $L_2P_4$. This observation indicates that the exhausting of $Zn^{2+}$ by $ZRL_5P_4$ resulted in a greater inhibition, and encouraged further exploration of the in vitro cytotoxicity of $ZRL_5P_4$ in EBV-positive cells.

Figure 18A:
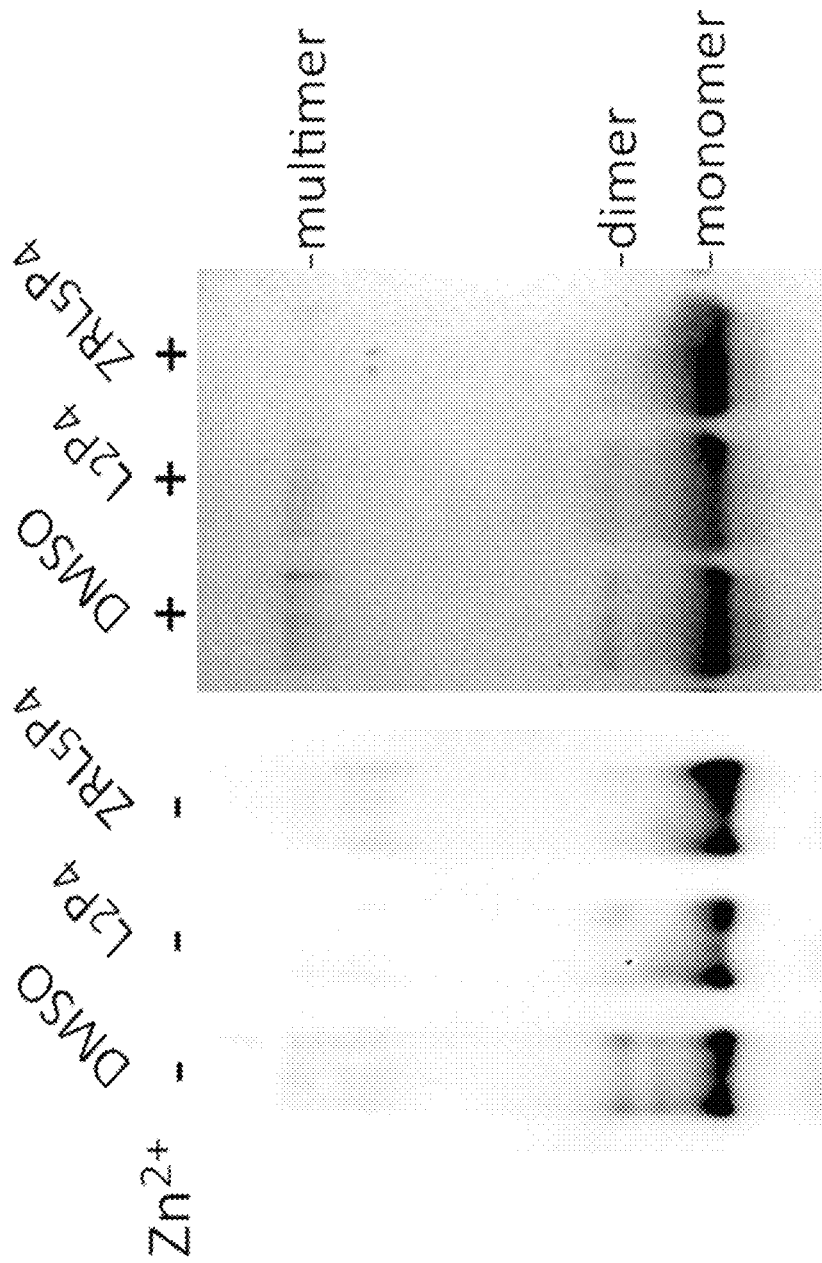
Figure 18B:
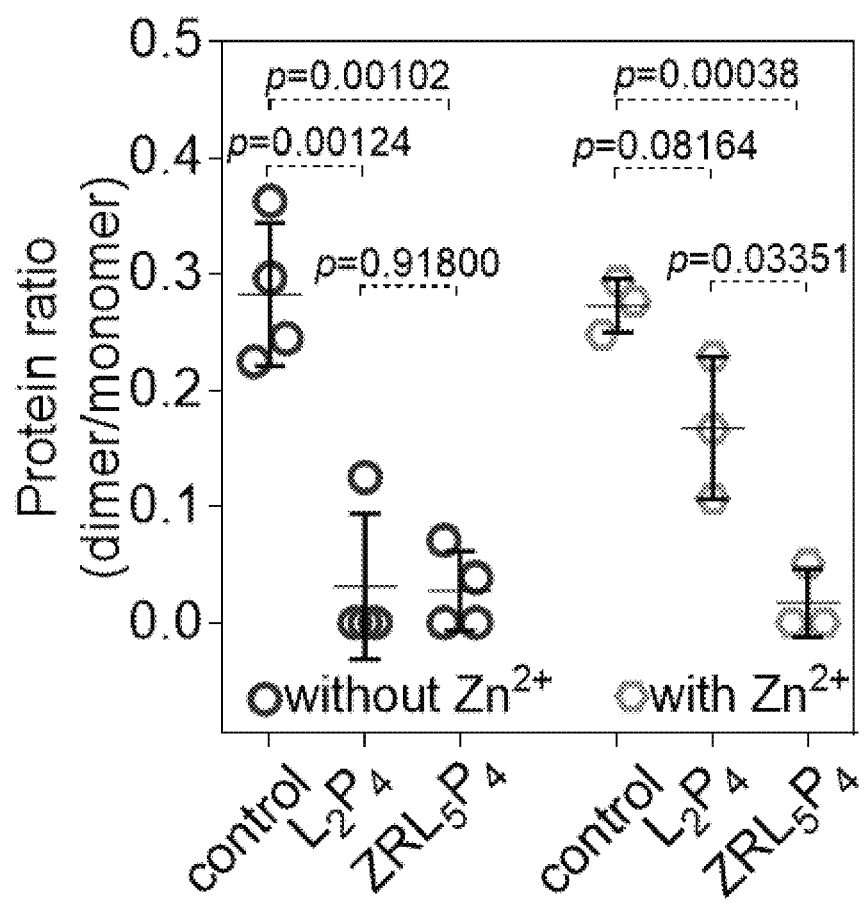
Figure 18C:
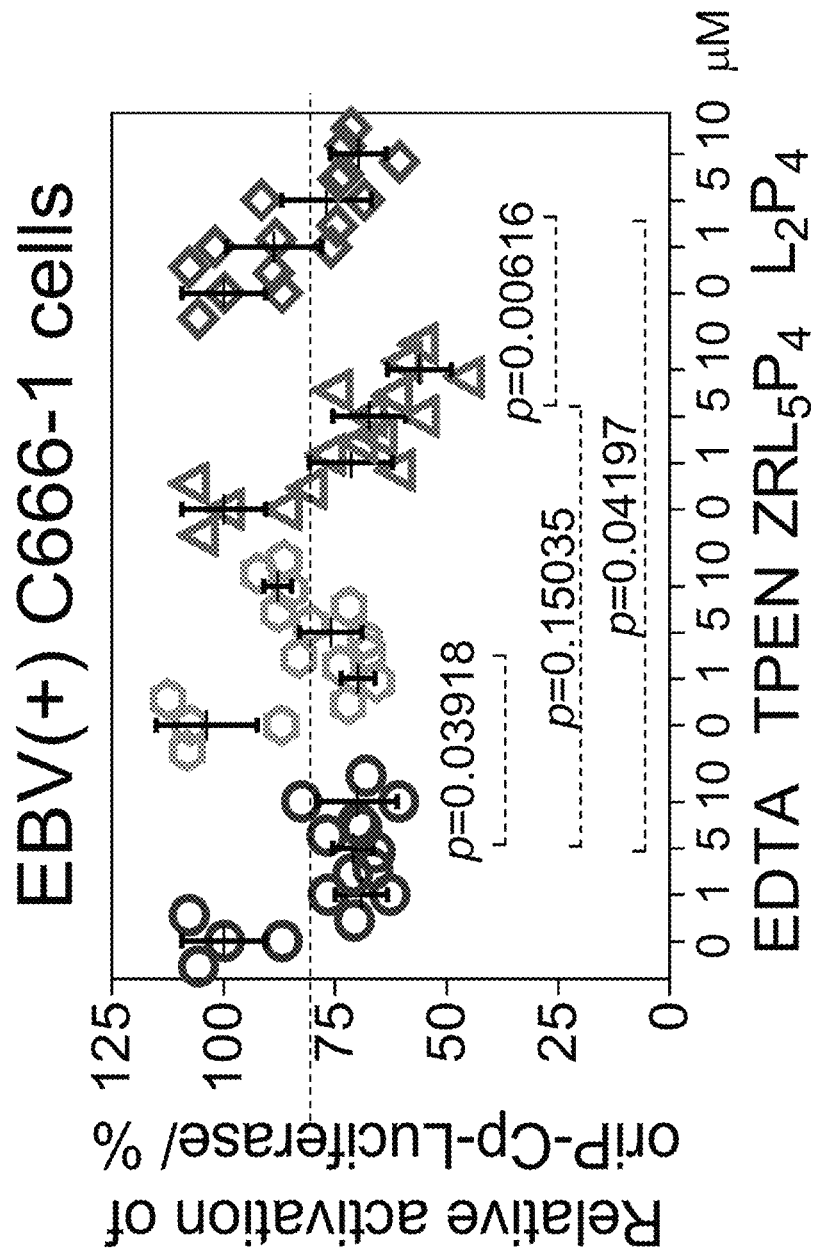
Figure 18D:
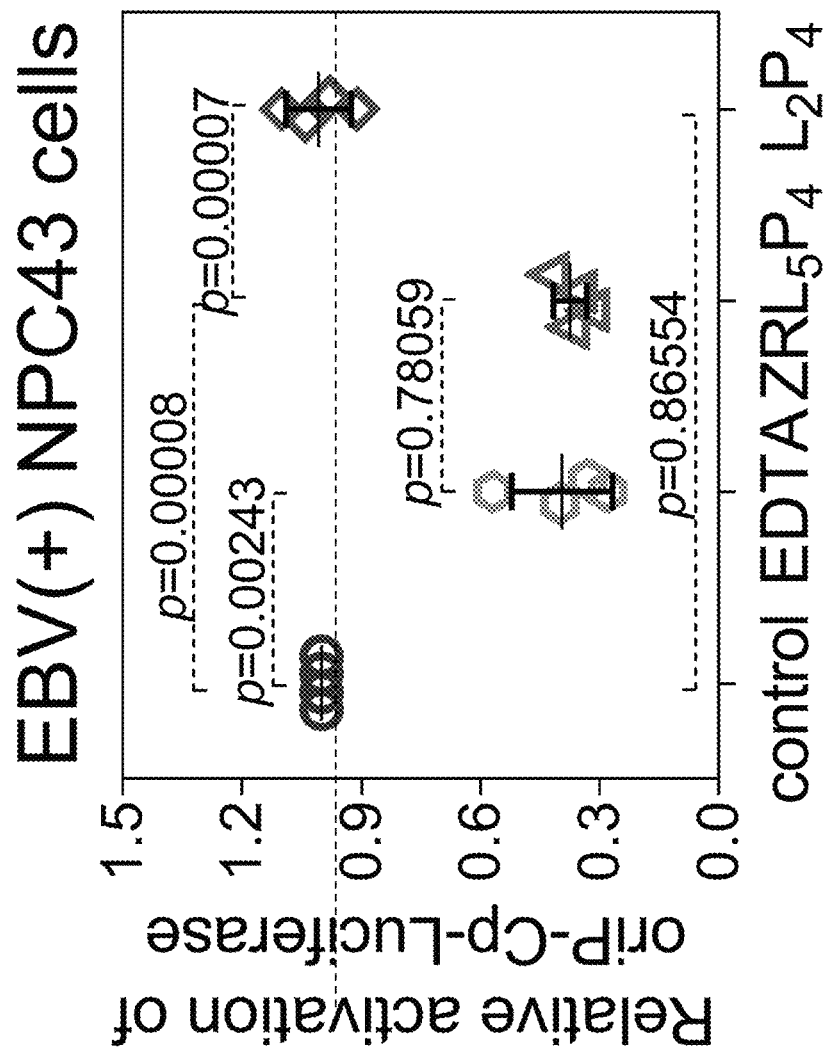
Figure 18E:
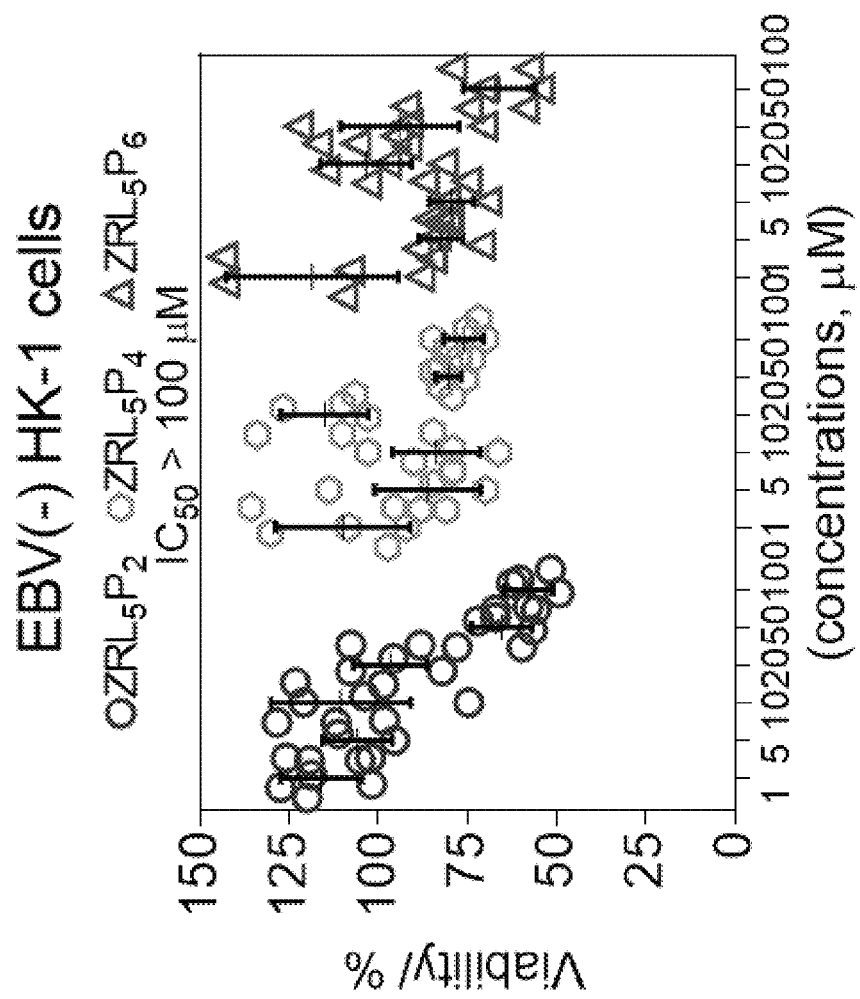
Figure 18F:
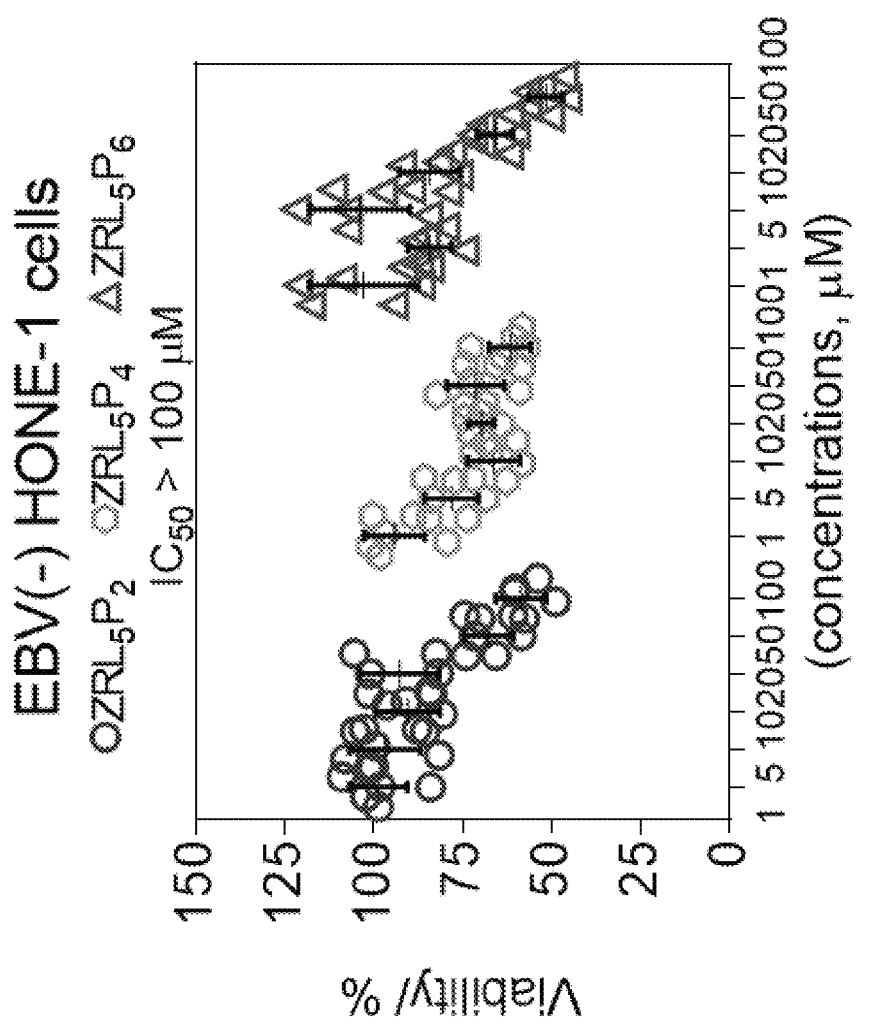

Before assaying the cytotoxicity of $ZRL_5P_4$, its ability to bind cellular zinc and affect EBNA1 transactivation was measured as shown in FIG. 18C-D. EBV-positive C666-1 and NPC43 cells were exposed to $ZRL_5P_4$, two chelators known to have high specificity for zinc—ethylenediaminetetraacetic acid (EDTA) and N,N,N',N'-tetrakis(2-pyridylmethyl)ethylenediamine (TPEN), as well as $L_2P_4$. Both $ZRL_5P_4$ and $L_2P_4$ diminished transactivation by EBNA1 in dose-dependent manner, and the effects of $ZRL_5P_4$ was more potent than $L_2P_4$ in both C666-1 (p value=0.00616) and NPC43 cell lines (p value=0.00007).

$ZRL_5P_4$ Reduces the Viability of EBV-Positive Cells and Localizes to their Nuclei.

Figure 18G:
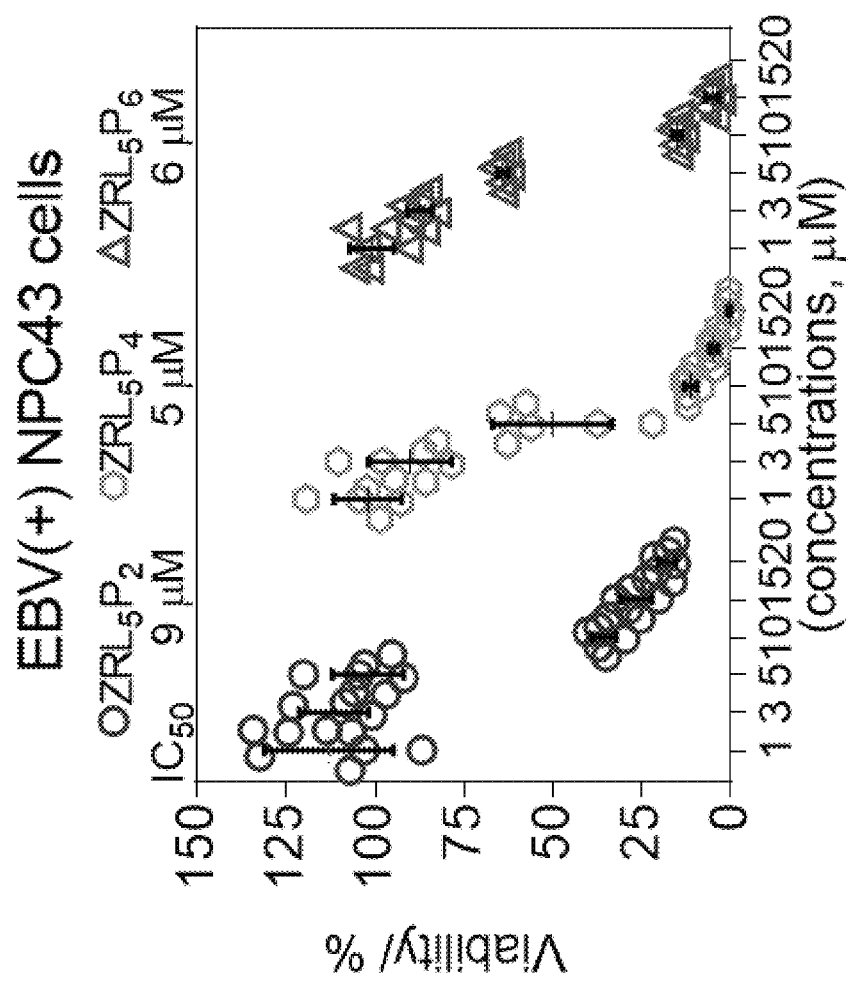
Figure 18H:
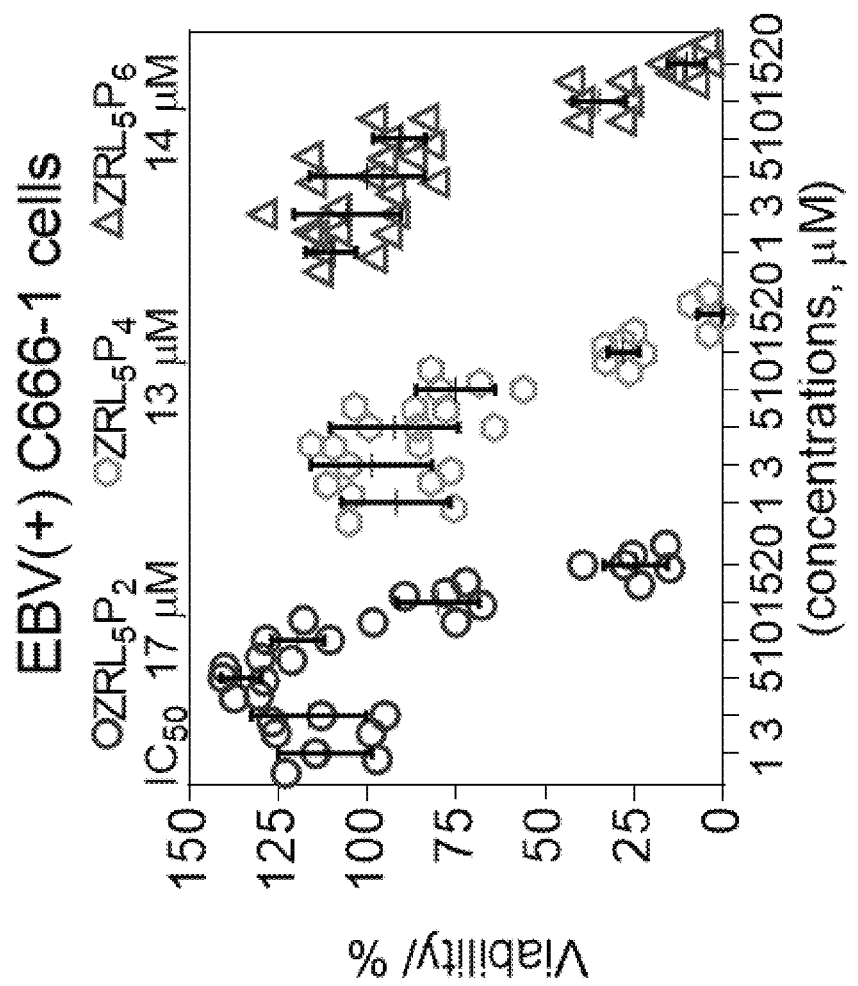
Figure 18I:
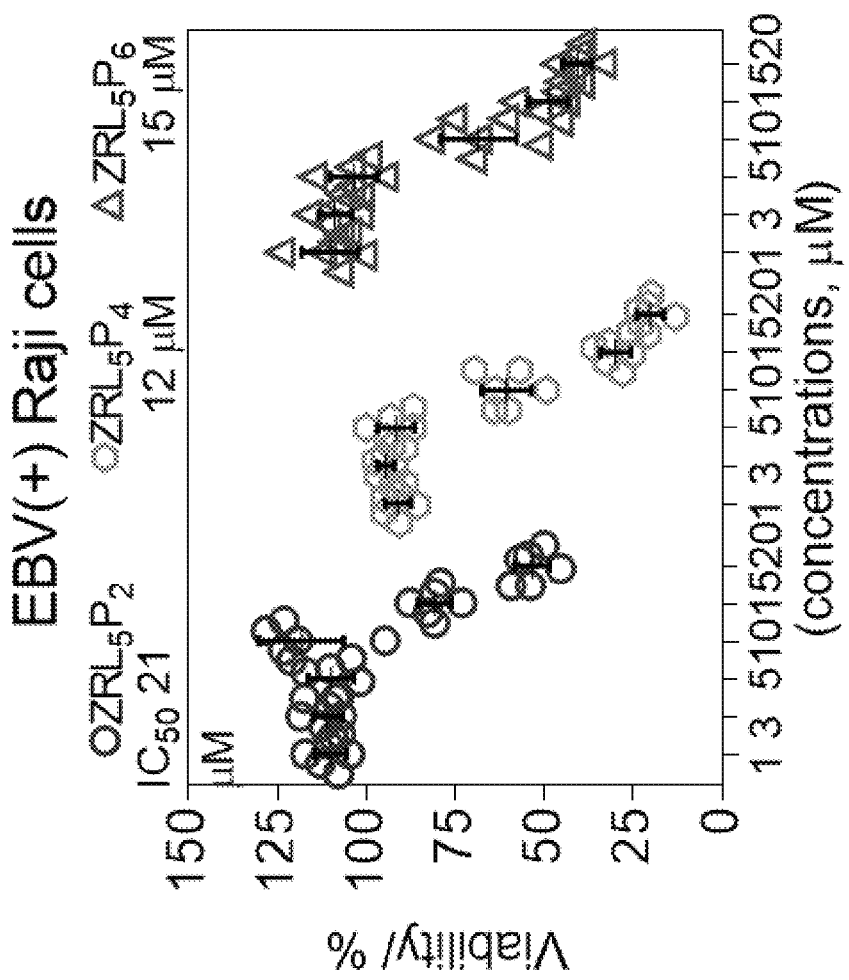

The cell viability of a panel of EBV-negative (HK-1 and HONE-1 NPC cells) and EBV-positive (NPC43, C666-1, Raji lymphoma cells) cells treated with $ZRL_5P_2$, $ZRL_5P_4$, and $ZRL_5P_6$(FIG. 18E-I) was next measured. $ZRL_5P_2$ was included to show that the nucleus permeability is critical for the cytotoxicity initiated by the zinc-chelator and the EBNA1 binding peptide, while $ZRL_5P_6$ was included to examine if the variation of the EBNA1 binding sequence is essential for the tumor cell growth. Cytotoxicity was measured by using the MTT assay. Treatment in the EBV-negative cells showed negligible inhibition over the range of 1-100 μM for all three probes (FIG. 18E-F), whereas obvious cytotoxicity was observed in the EBV-positive cells (both EBV-positive nasopharyngeal carcinoma cells and EBV-positive Burkitt's lymphoma cells), even when treated with low dosages of 1-20 μM probes (FIG. 18G-I). $ZRL_5P_4$ and $ZRL_5P_6$ displayed very similar growth-inhibitory effects, with $ZRL_5P_2$ being the least efficient. When compared to the cytotoxicity study of $L_2P_4$($IC_{50}$; 23 μM in NPC43, 27 μM in C666-1 and 27 μM in Raji cells), $ZRL_5P_4$ is likely to be more potent ($IC_{50}$; 5 μM in NPC43, 13 μM in C666-1 and 12 μM in Raji cells), indicating that the exploitation of the zinc chelator will enhance the cytotoxic activity of the EBNA1 probes in EBV latently infected cells, regardless of epithelial or lymphoid origin. On the other hand, the results of $ZRL_5P_6$ suggest that the variation in the amino acid sequence in the EBNA1 binding penta-peptide is not essential in inhibiting the in vitro biological activities.

Figure 19A:
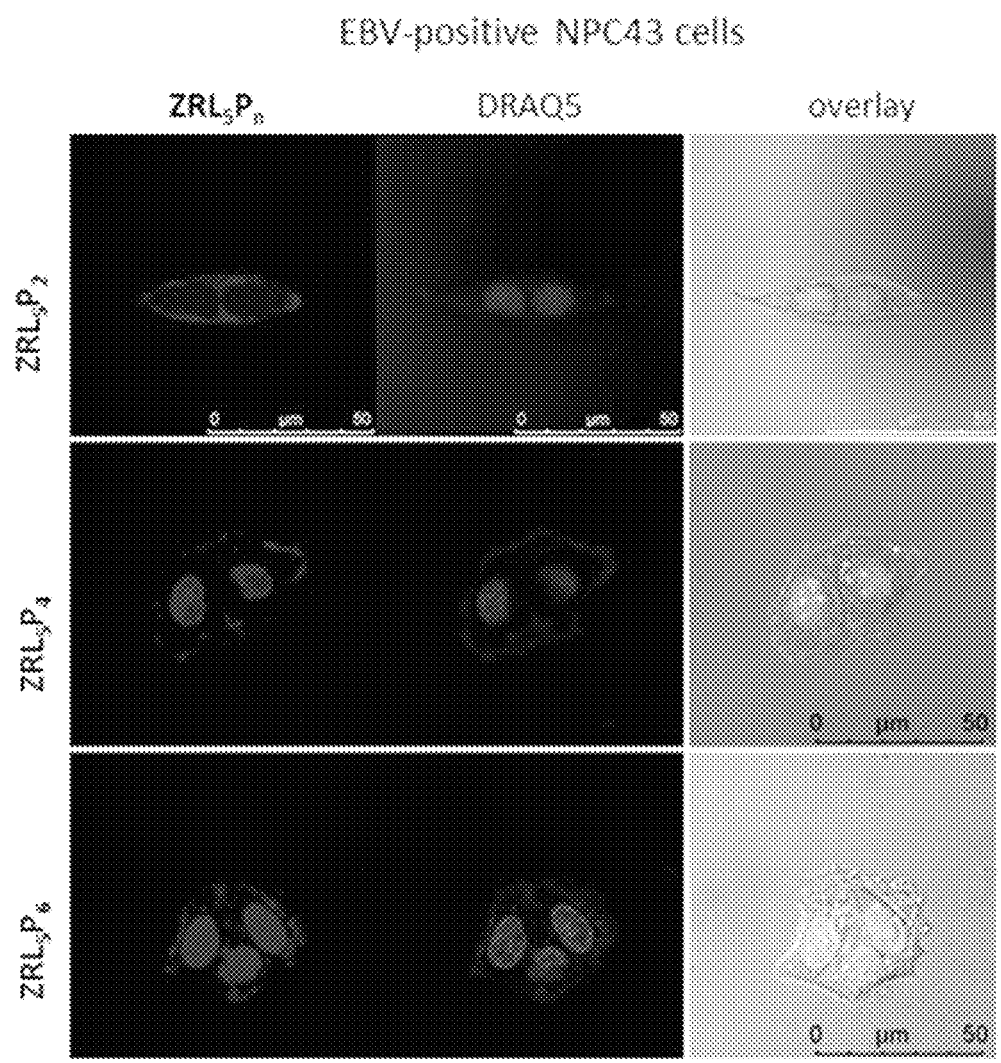
Figure 19B:
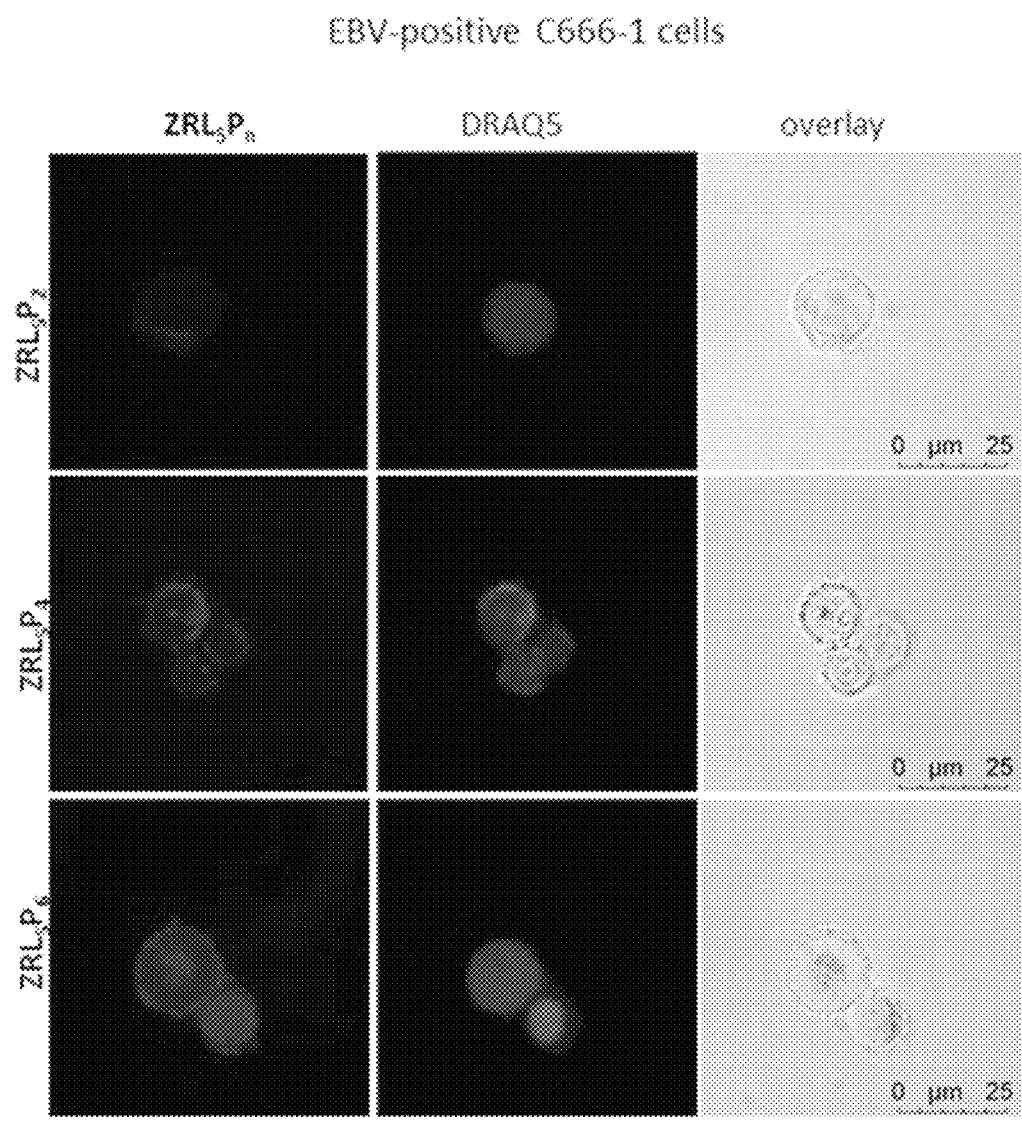
Figure 19C:
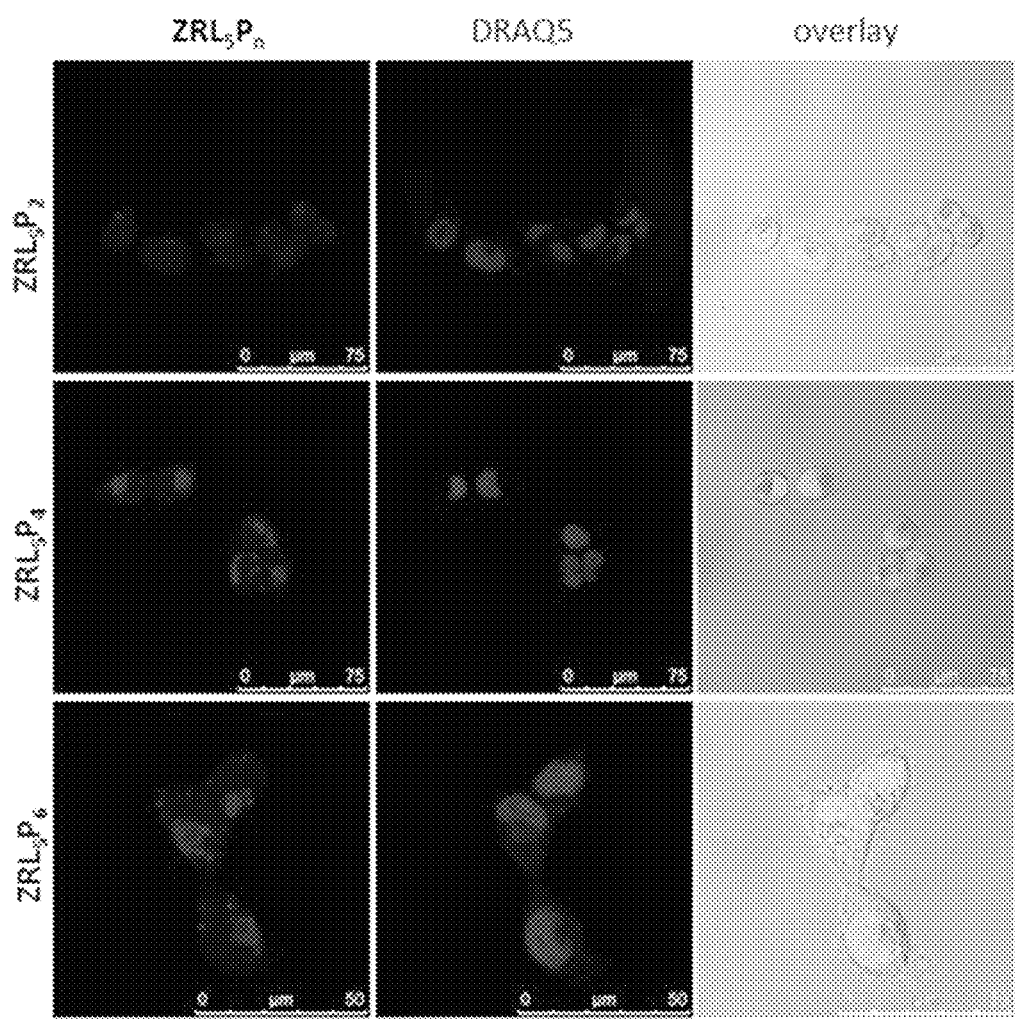
Figure 20A:
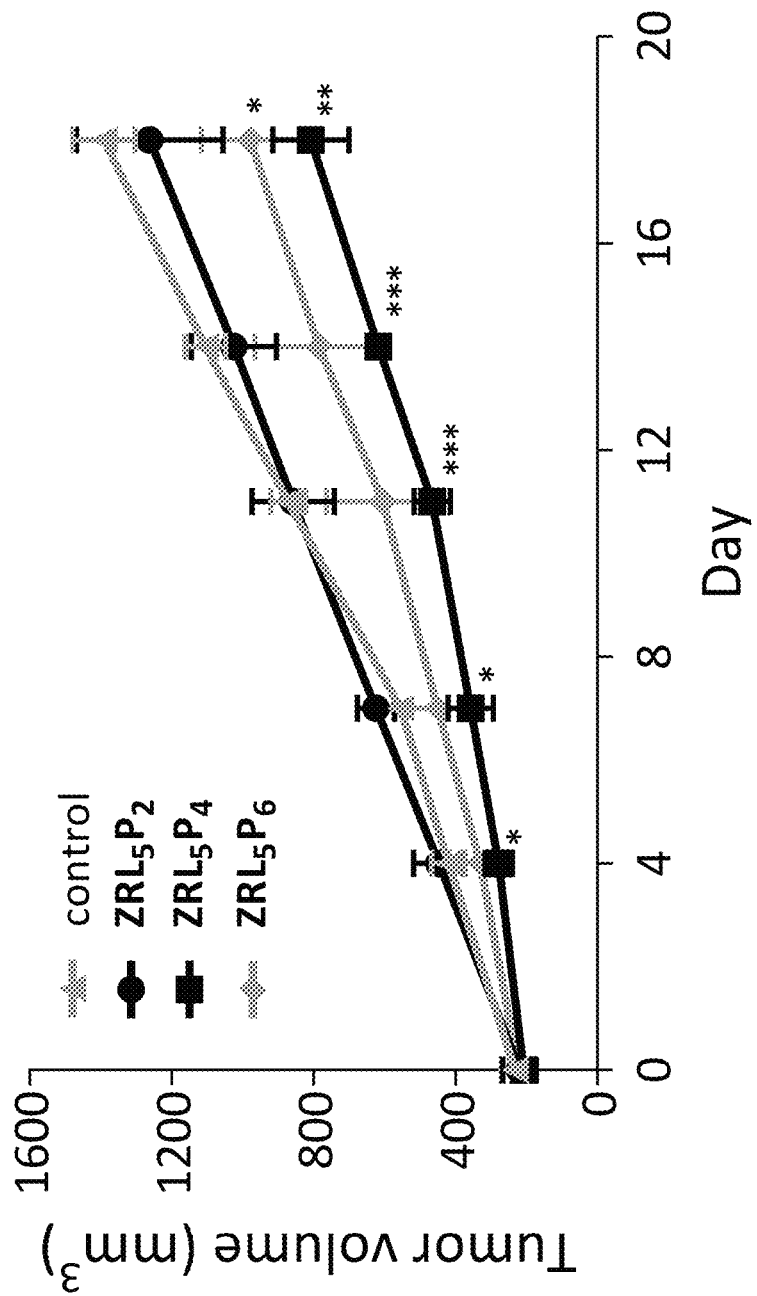
Figure 20B:
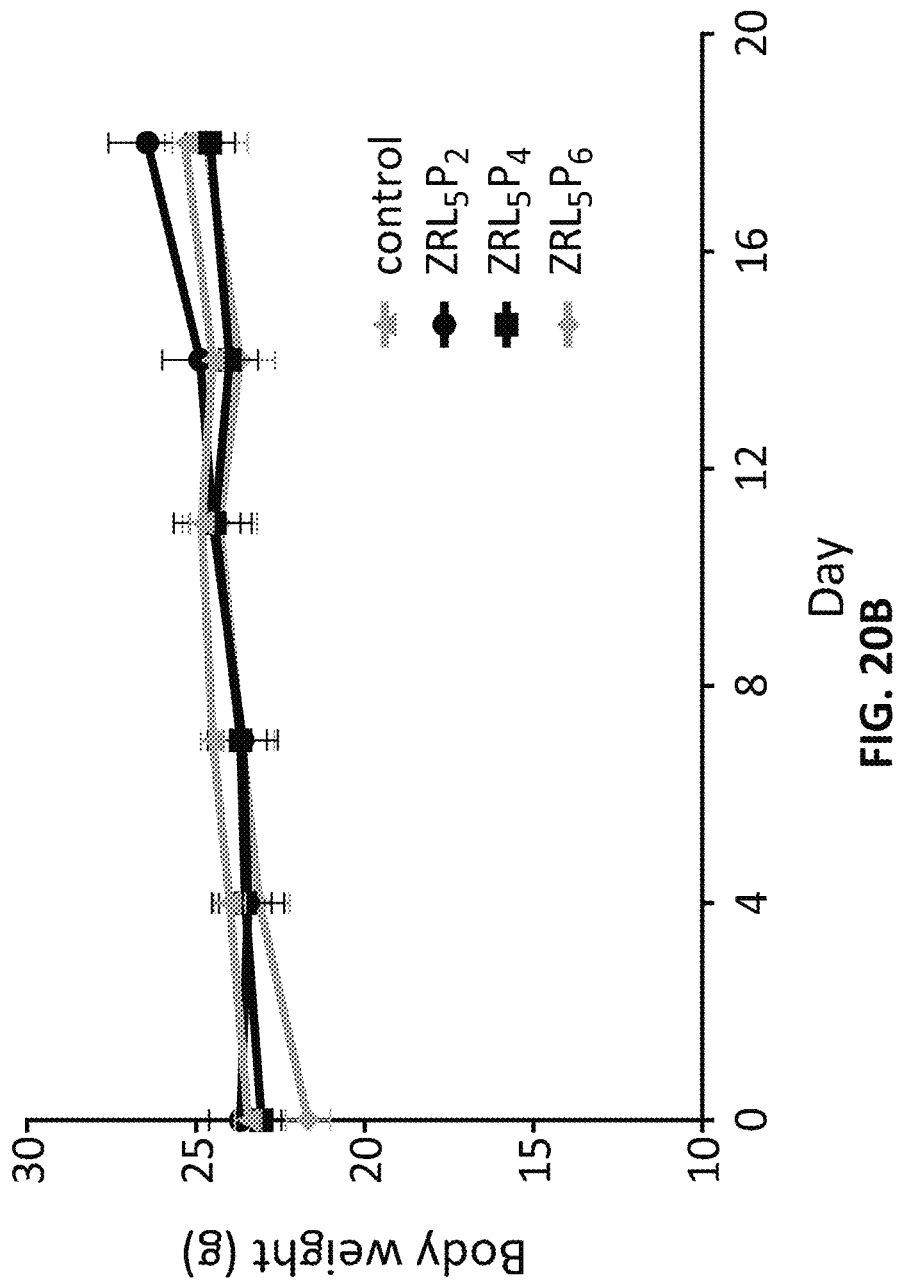
Figure 20C:
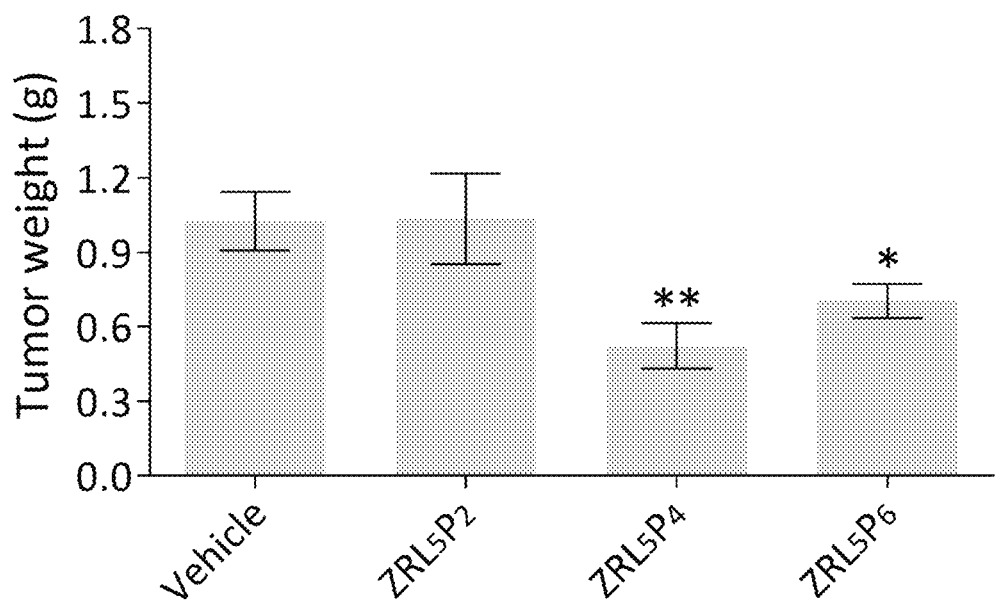
Figure 20D:
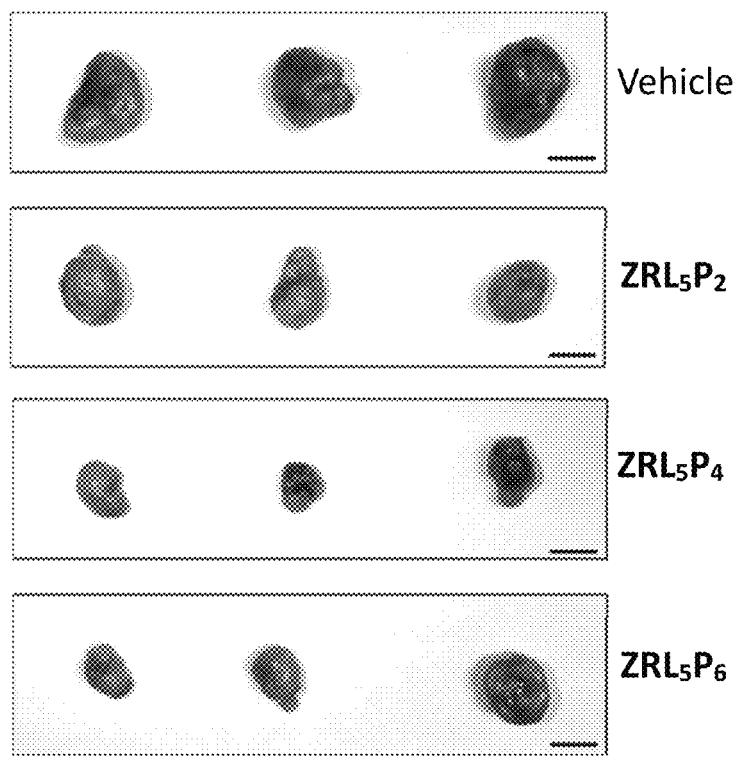
Figure 20E:
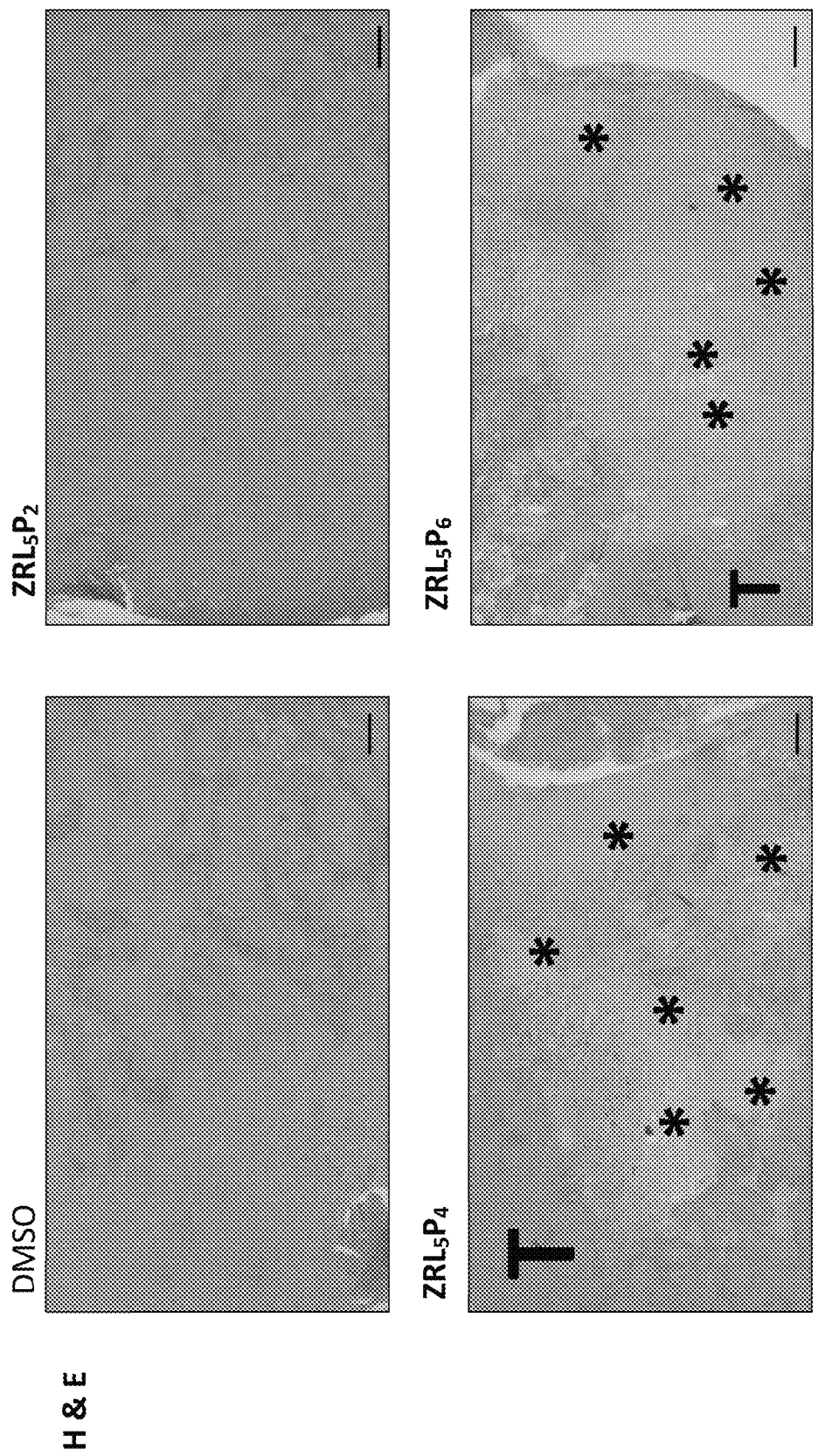
Figure 20F:
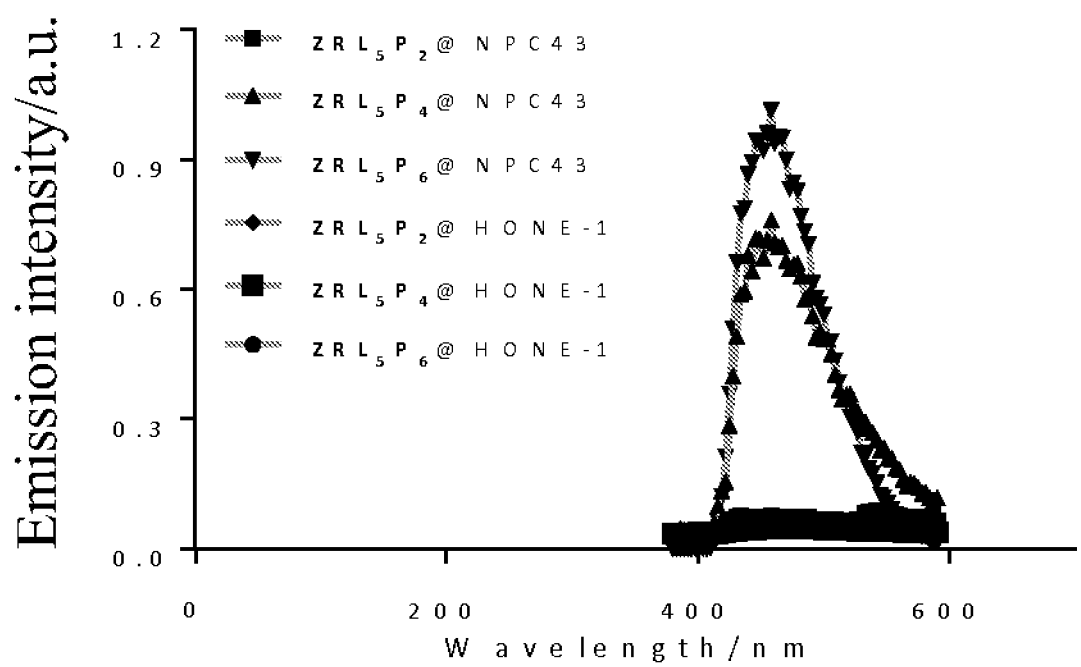

Given that nuclear localization is a prerequisite for EBNA1 to maintain and replicate the EBV viral genome, a probe with nuclear permeability is preferred. The above MTT assay results also show that the entry into the nuclei is essential for the EBNA1 probes to inhibit the tumor cell viability. Therefore, the sub-cellular localization of $ZRL_5P_2$, $ZRL_5P_4$, and $ZRL_5P_6$ was assessed in both EBV-positive (C666-1 and NPC43) and EBV-negative cell lines (HONE-1) under two-photon excitation microscopy ($\lambda_{ex}$: 700 nm). Two-photon excitation microscopy is superior for deeper tissue penetration and reduced photobleaching. After incubation for 3 h, the fluorescence signals of $ZRL_5P_2$, $ZRL_5P_4$, and $ZRL_5P_6$ were collected in the blue channel. As shown in FIG. 19A-C, $ZRL_5P_4$ and $ZRL_5P_6$ demonstrated clear nuclear localization in the EBV-positive cells with the assistance of the incorporated NLS(RrRK) and hence achieved better growth inhibition (FIG. 18E-18I), whereas $ZRL_5P_2$ was only found in the cytoplasm (FIG. 19A-B, 20F). Moreover, all three probes showed no nuclear permeability in EBV-negative cells (FIG. 19C, 20F). Furthermore, majority of $ZRL_5P_4$ and $ZRL_5P_6$ was found in the nuclei of the EBV-infected cells, and this is in contrast to the imaging results of $L_2P_4$ we previously reported, which show that majority of $L_2P_4$ was localized to the cytoplasm, only a small portion was found in the nuclei.

$ZRL_5P_4$ Inhibits the Growth of EBV-Positive Tumors in BALB/c Mice.

After the investigation of the in vitro cytotoxicity, the in vivo effects of the three new EBNA1 probes ($ZRL_5P_2$, $ZRL_5P_4$, $ZRL_5P_6$) were then examined. BALB/c nude mice transplanted with the EBV-positive C666-1 xenografts were treated with these probes (4 µg/injection), or with a vehicle control. Intra-tumoral injection was performed to deliver the agents to the animal, and injection was carried out biweekly. Body weight and tumor volumes were measured twice weekly. After an 18-day treatment period, mice were sacrificed and the tumors and organs were excised and weighed.

Tumor growth was significantly inhibited by treatment with $ZRL_5P_4$ and $ZRL_5P_6$. At the end of the treatment period (day 18), the average tumor volume of mice treated with $ZRL_5P_4$ was decreased by 41.9% (p<0.01), compared to the control. Treatment with $ZRL_5P_6$ led to a 29.6% decrease in tumor volume compared to the control (p<0.05) (FIGS. 20A and 20D). There was no significant difference in both tumor volume and tumor weight when comparing the effects of $ZRL_5P_4$ and $ZRL_5P_6$. $ZRL_5P_2$ without NLS, however, did not significantly affect tumor growth at either dose. Tumors were also weighed at the experimental endpoint. Compared to the control, the average tumor weight was decreased by 49.2% (p<0.05) and 31.4% (p<0.05) after treatment with $ZRL_5P_4$ and $ZRL_5P_6$, respectively (FIG. 20C). As shown in FIG. 20B and FIG. 23A-E, treatment with $ZRL_5P_2$, $ZRL_5P_4$, or $ZRL_5P_6$ did not cause significant changes in body or organ weights compared to the vehicle control, indicating that neither probe exhibited a toxic effect in vivo. Together, these results indicate that $ZRL_5P_4$ and $ZRL_5P_6$ are potential anti-EBV agents having no appreciable in vivo toxicity. Also, $ZRL_5P_4$ performed better as a reporter probe in binding with EBNA1 and $Zn^{2+}$. When the tumor sections were stained with H & E to examine the tissue morphology, cell necrosis was much more frequently observed in the tumor tissues with the treatment of $ZRL_5P_4$ or $ZRL_5P_6$ than the $ZRL_5P_2$ and the solvent control (FIG. 20E). The cell death could be due to the cytotoxic activities of $ZRL_5P_4$ and $ZRL_5P_6$ observed in the MTT assay for C666-1 cells (FIG. 19B), and that can also explain why the tumors shrank after treatments with the new EBNA1 probes. For the HeLa EBV-negative xenografts (FIG. 24A-D), there was no significant difference in both tumour volume and tumour weight between the control mice and those treated with probes.

Reactivation of EBV Lytic Cycle by $ZRL_5P_4$.

Figure 21A:
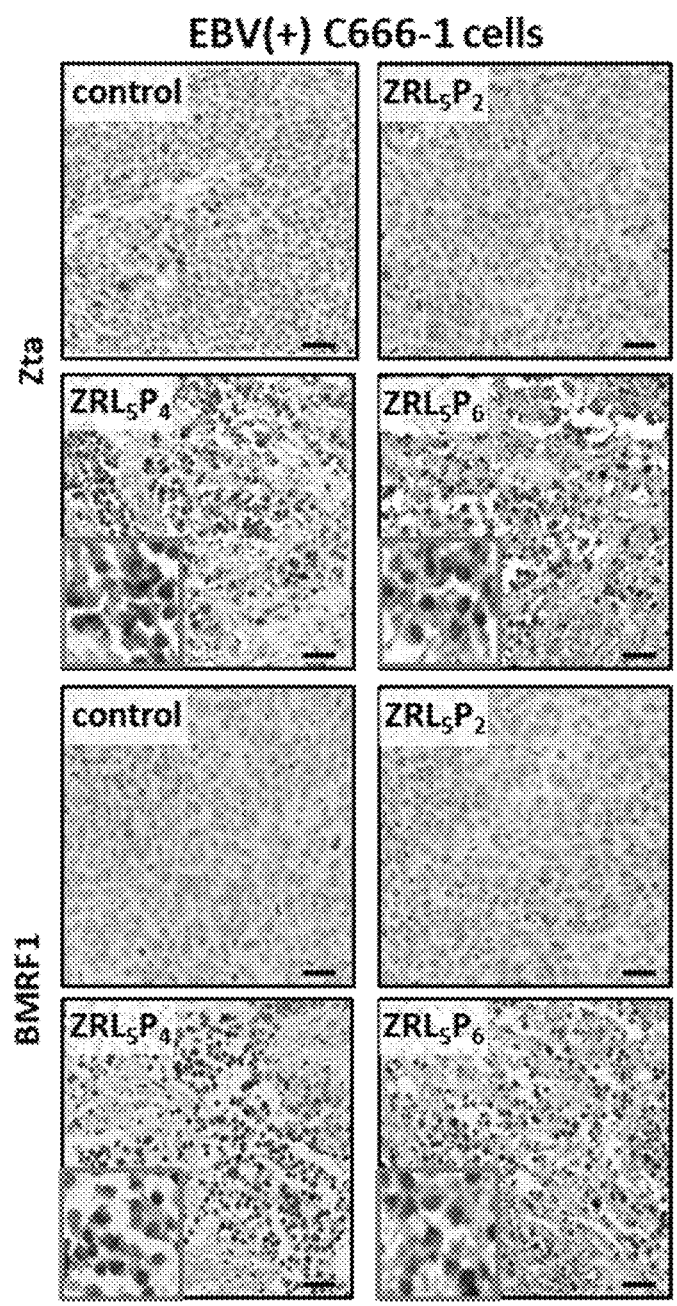

To investigate the mechanism by which $ZRL_5P_4$ and $ZRL_5P_6$ resulted in the necrotic tumors in vivo (FIG. 20E), it was next determined whether this phenomenon could be due to the induction of the EBV lytic gene products, as the full lytic induction will cause tumor cell death and release of EBV particles. The immediate early and early lytic proteins, BZLF1 (Zta) and BMRF1, were examined in the C666-1 derived tumor tissues in the above animal study (FIG. 20A-E). The tumor sections were analyzed with immunohistochemistry (IHC), the EBV lytic proteins, Zta and BMRF1, were mainly detected in the tumors injected with $ZRL_5P_4$ or $ZRL_5P_6$. Nuclear staining of these two lytic proteins was observed in tumor cells adjacent to the necrotic tumor tissues (FIG. 21A). After treatment with $ZRL_5P_4$, about 12.5 and 18.8% tumor areas were positive for Zta and BMRF1, respectively. On the other hand, only negative staining was detected in the solvent control for the two proteins, and 1.15% was observed in $ZRL_5P_2$ for BMRF1. The IHC results of Zta and BMRF1 in response to $ZRL_5P_6$ were similar to the $ZRL_5P_4$ (18.8% for Zta and 15.6% for BMRF1). Thus, these IHC results indicate that the necrotic tumor tissues could be the consequence of the induced lytic cycle by $ZRL_5P_4$ and $ZRL_5P_6$.

Figure 21B:
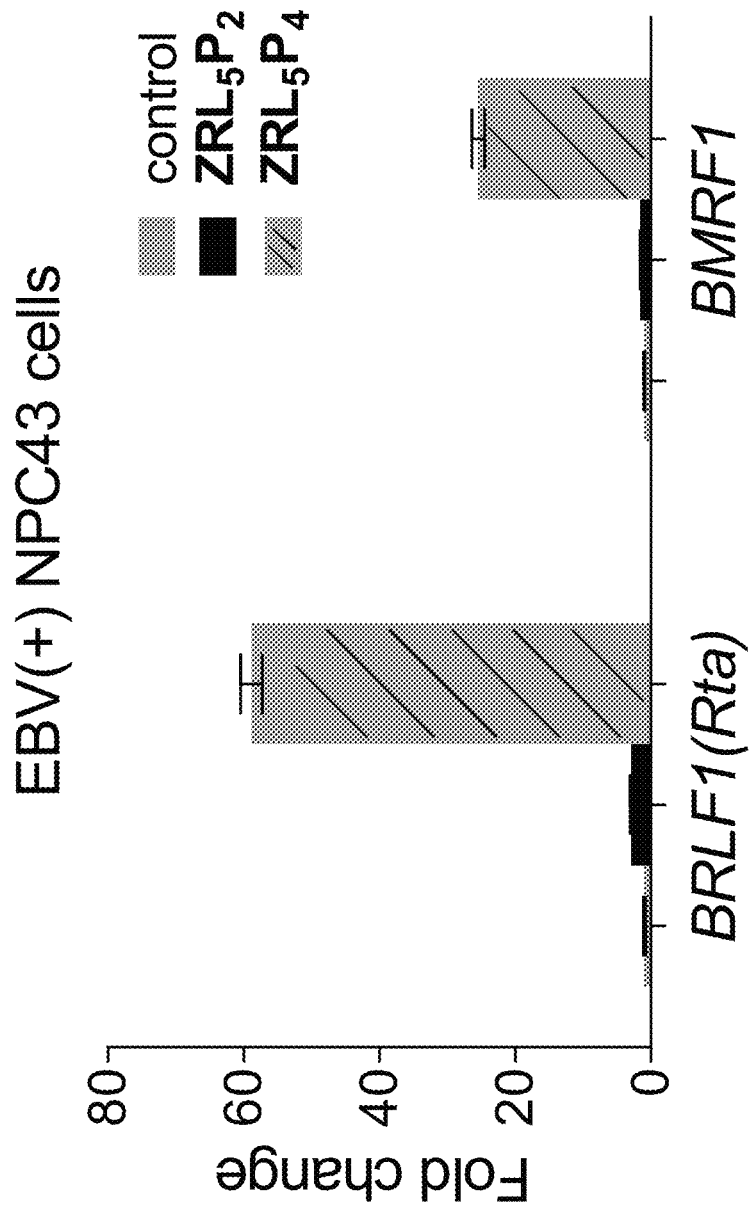
Figure 21C:
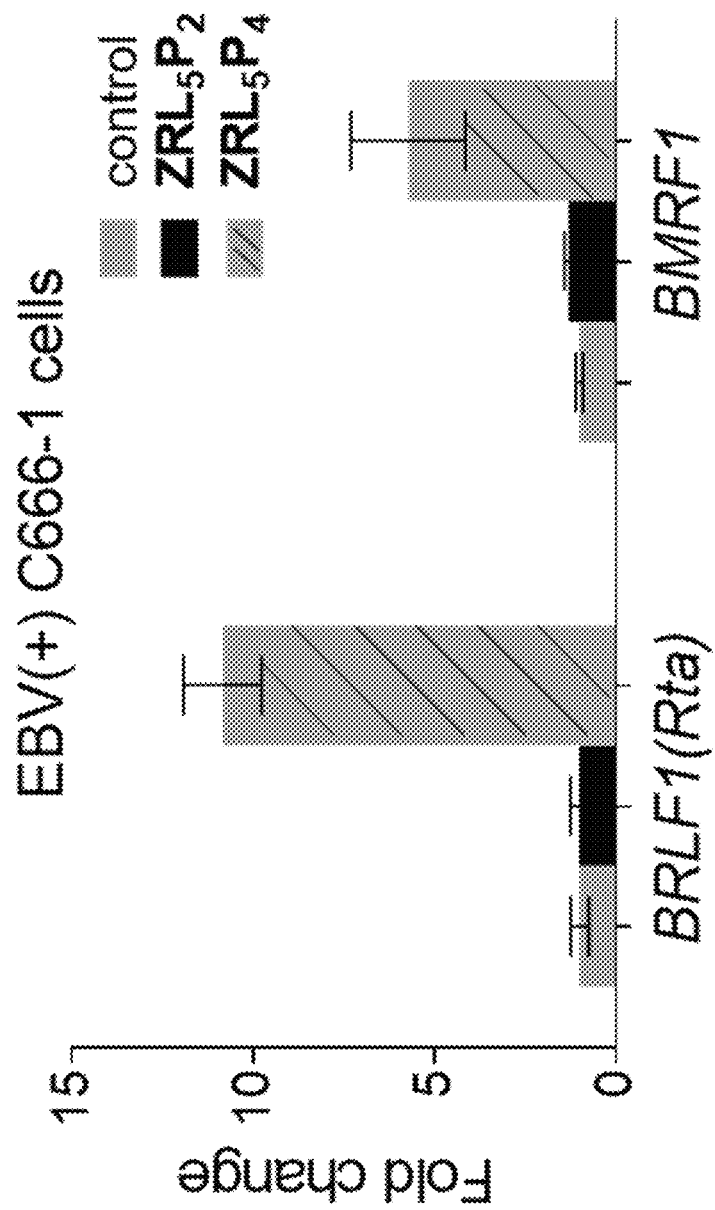
Figure 21D:
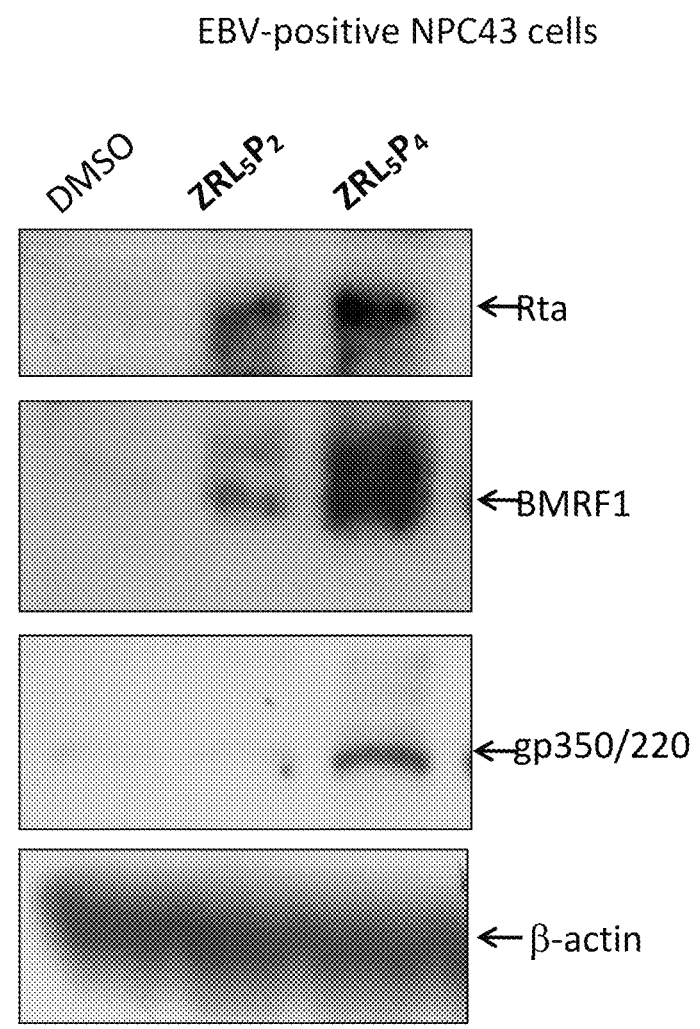

The inventor also included the other EBV-infected cell line NPC43 for the lytic phase analysis, the gene expression of the immediate early and early lytic genes, BRLF1 (Rta) and BMLF1, was studied in both NPC43 and C666-1 cell lines in response to 10 µM $ZRL_5P_4$. The gene expression was detected by qRT-PCR. The gene expression of both Rta and BMRF1 was strikingly induced by $ZRL_5P_4$, whereas their expression in response to $ZRL_5P_2$ was similar to that of the solvent control (FIG. 21B-C). The change was ~26- to ~59-fold in response to $ZRL_5P_4$ in NPC43 cells, and ~6 to ~11-fold induction for C666-1 cells. The gene expression results of Rta and BMRF1 were supported by the Western blot analysis which shows that the protein levels were specifically induced by $ZRL_5P_4$ in the two NPC cell lines (FIG. 21D). Besides these two early lytic proteins, the late protein gp350/220 for virion assembly was also induced by $ZRL_5P_4$. Although the expression of Rta and BMRF1 was also induced by $ZRL_5P_2$, the increased levels of expression were much weaker than that of $ZRL_5P_4$ and the gp350/220 levels were similar to the solvent control. It is likely that the entry of $ZRL_5P_4$ to the nuclei is critical for the induction of late lytic protein expression.

Figure 22A:
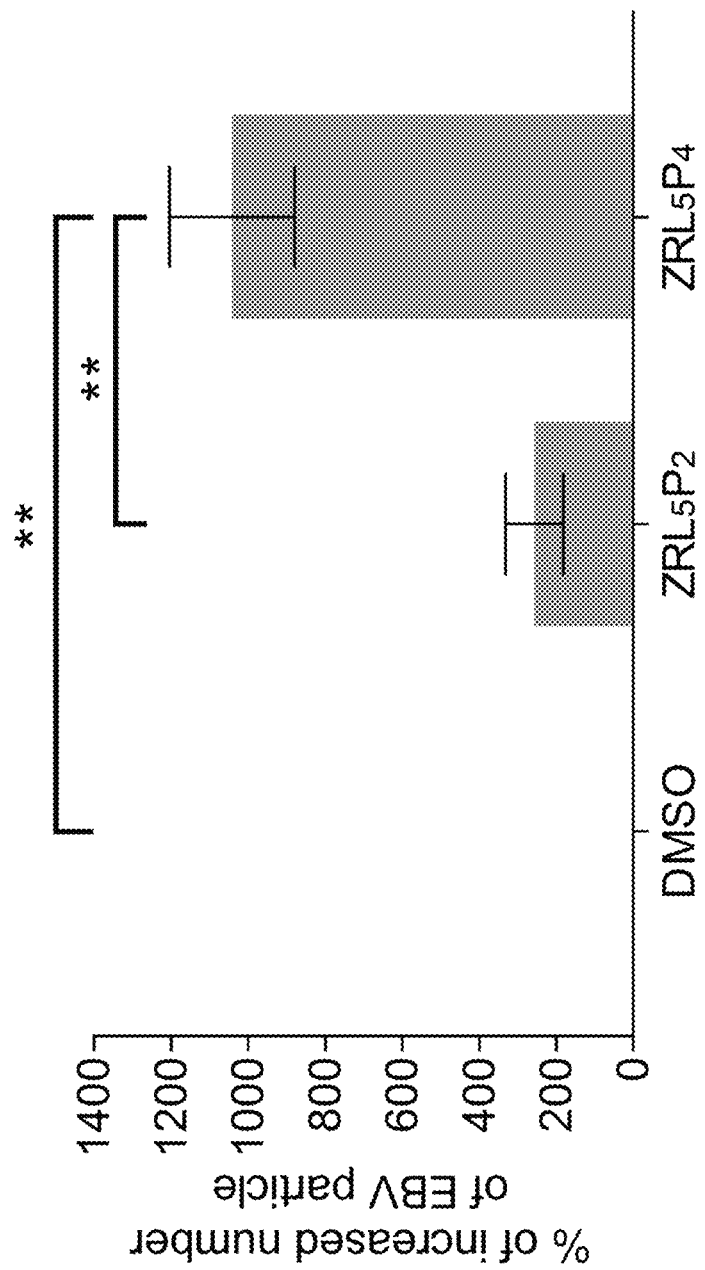
Figure 22B:
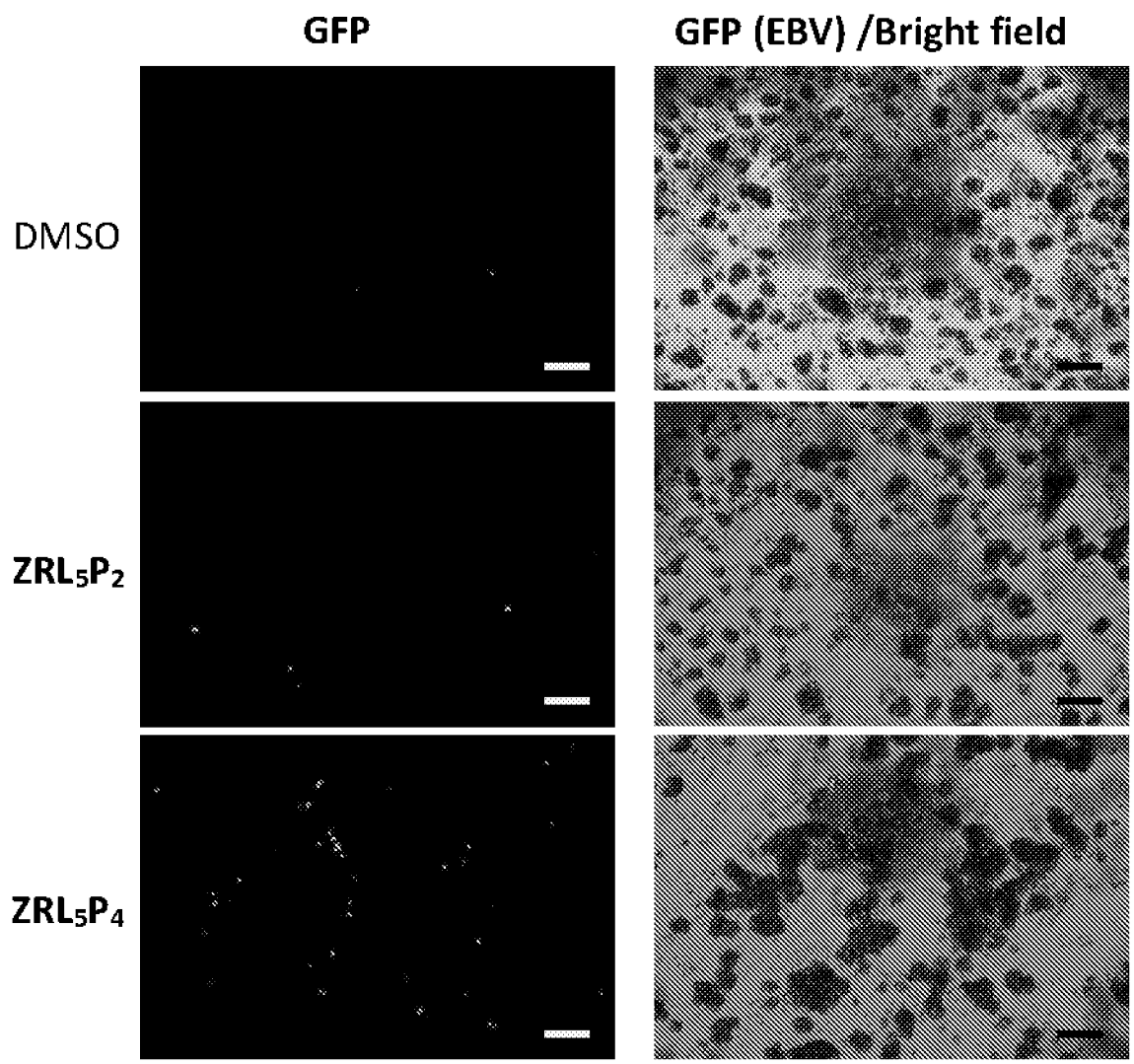
Figure 23A:
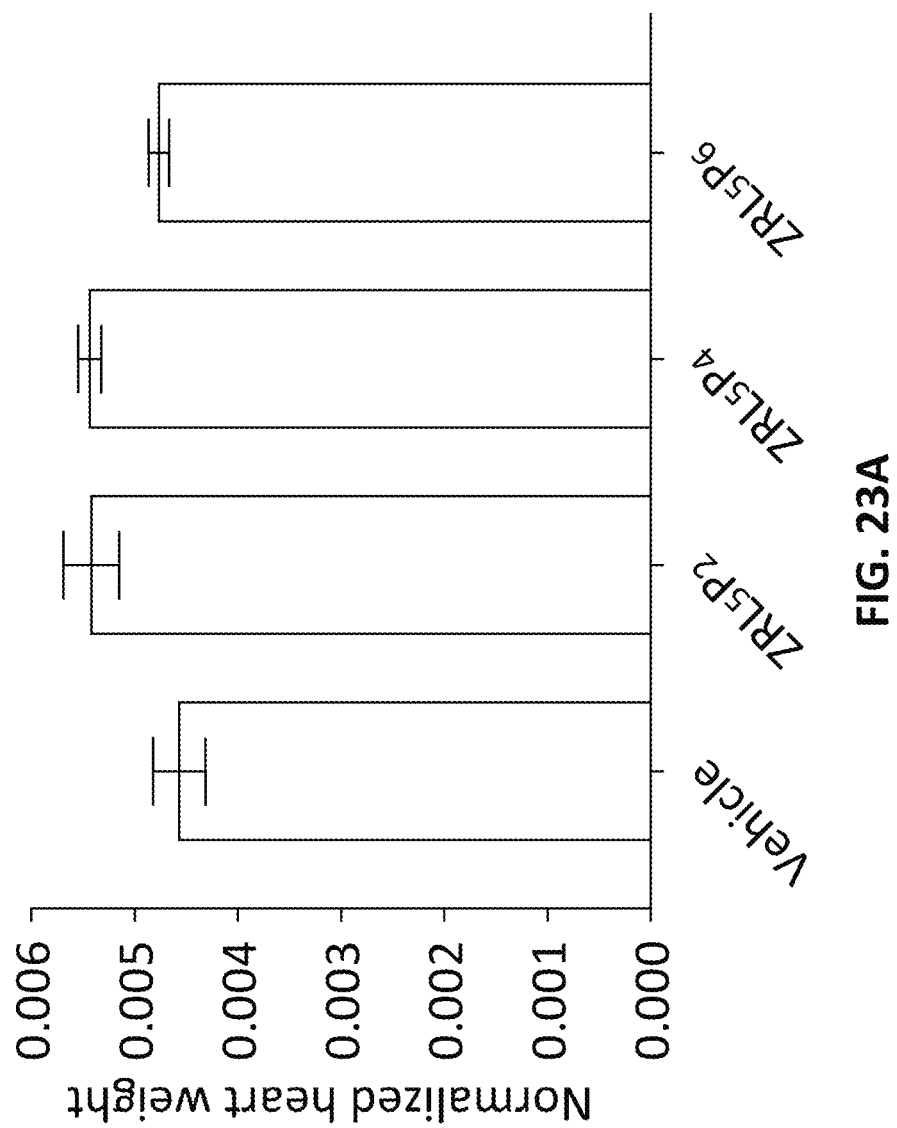
Figure 23B:
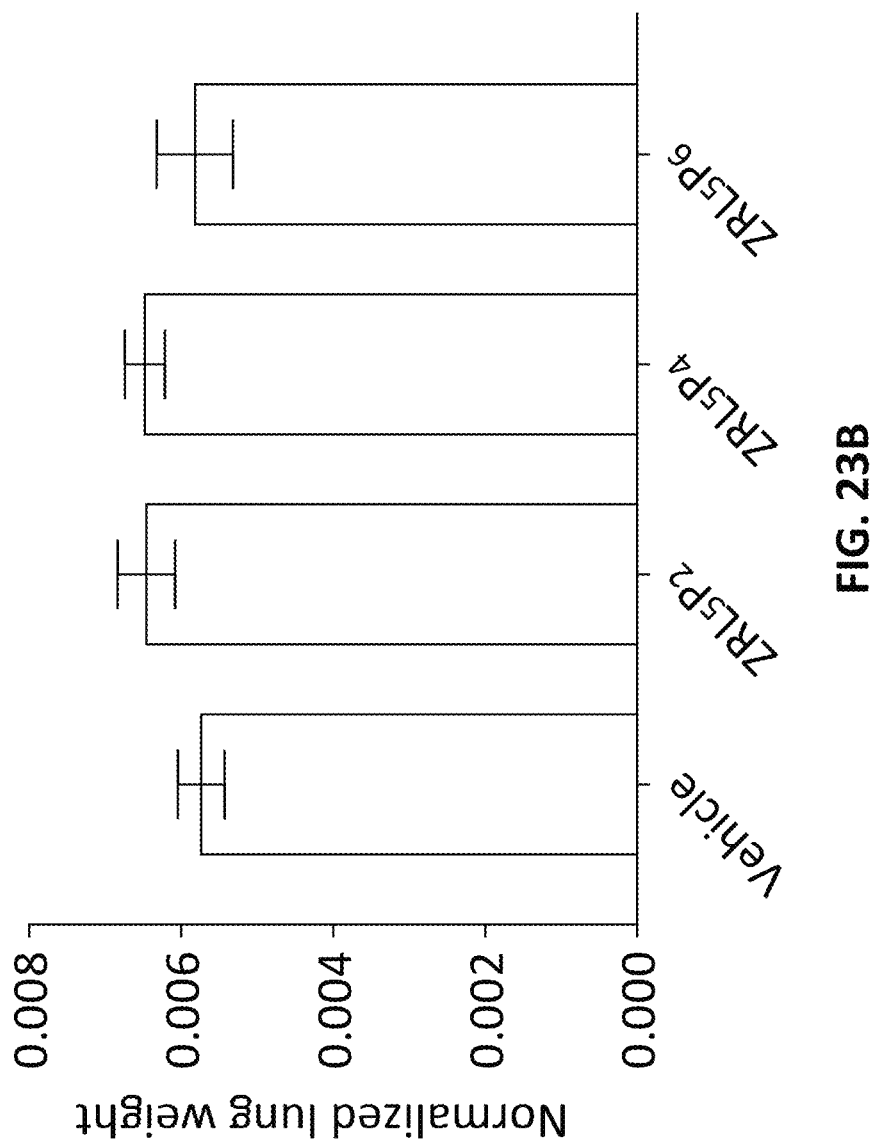
Figure 23C:
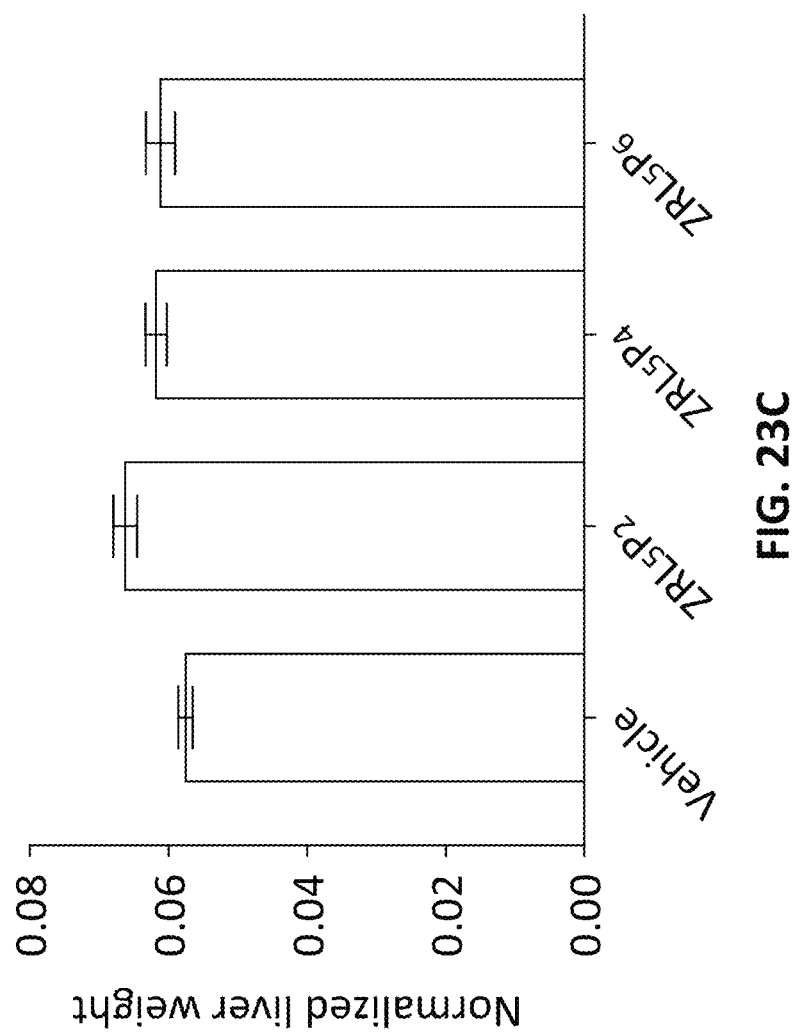
Figure 23D:
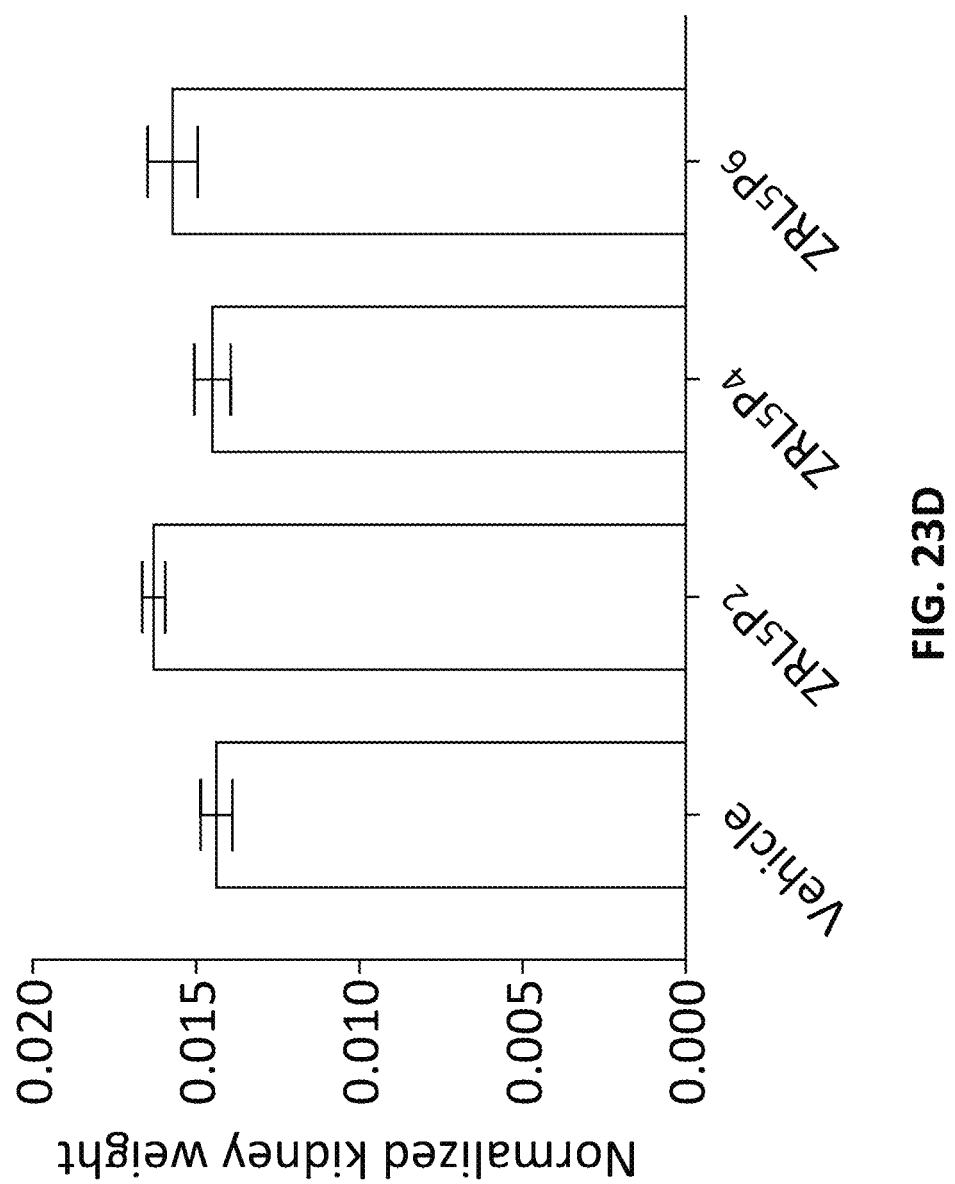
Figure 23E:
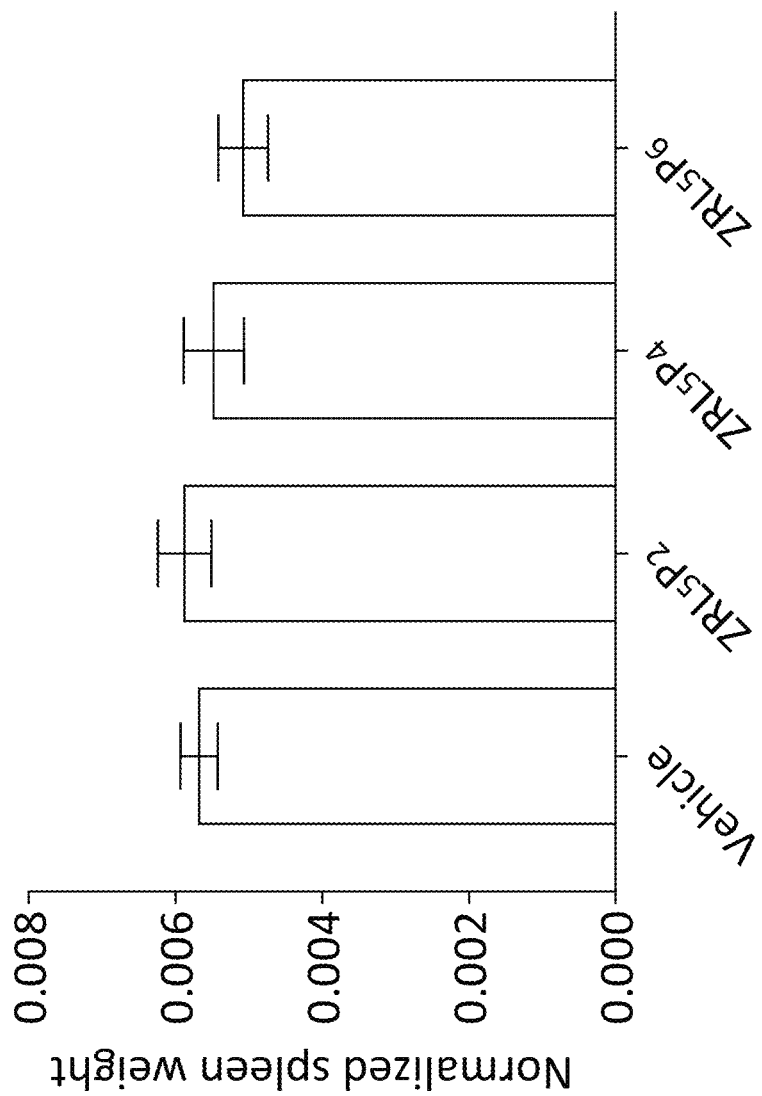
Figure 24A:
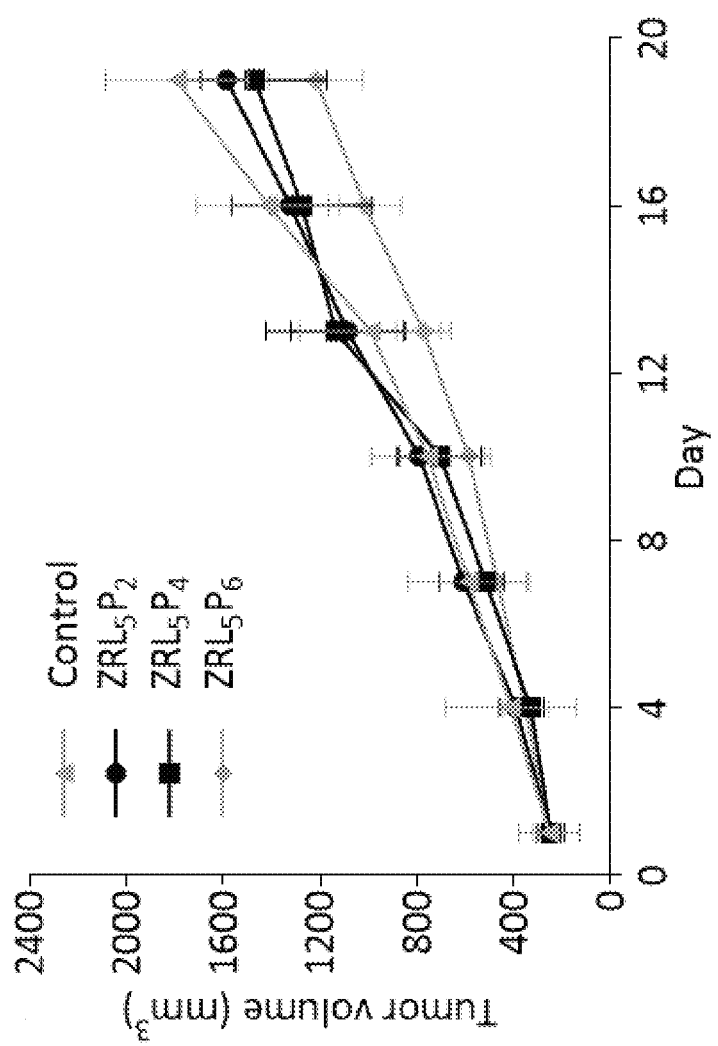
Figure 24B:
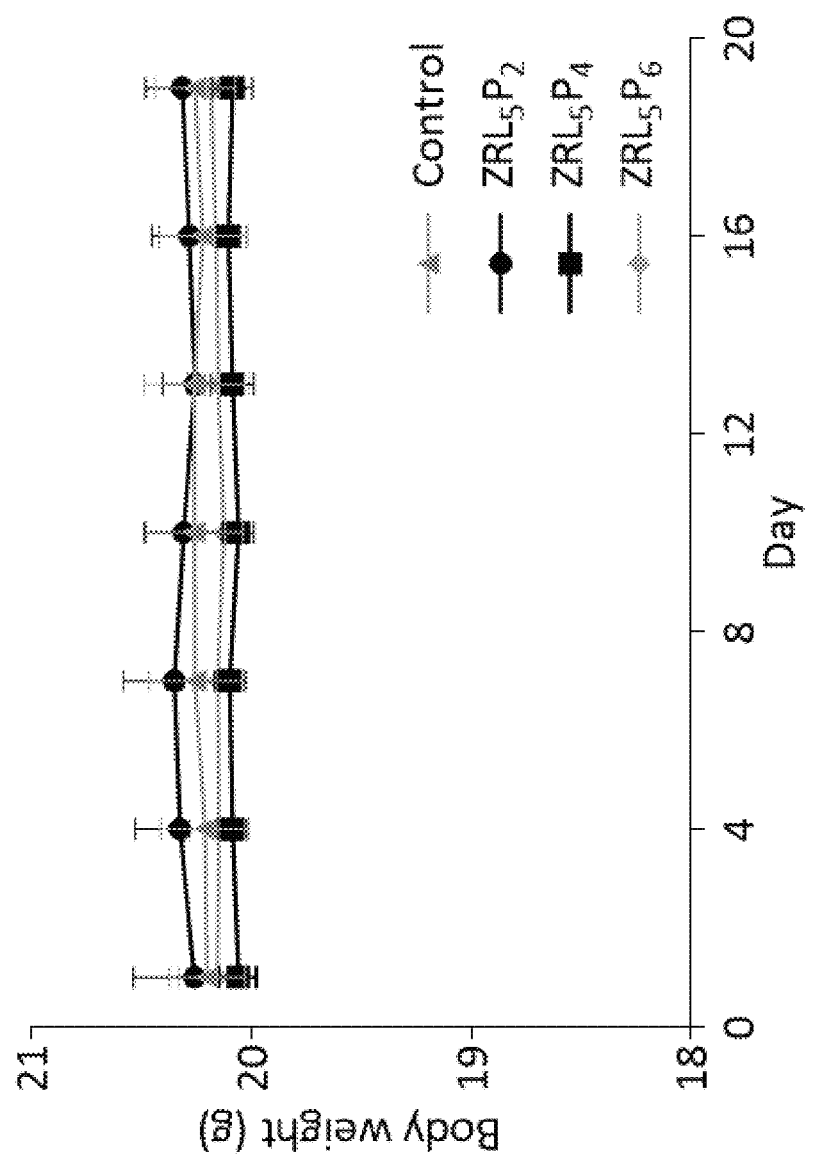
Figure 24C:
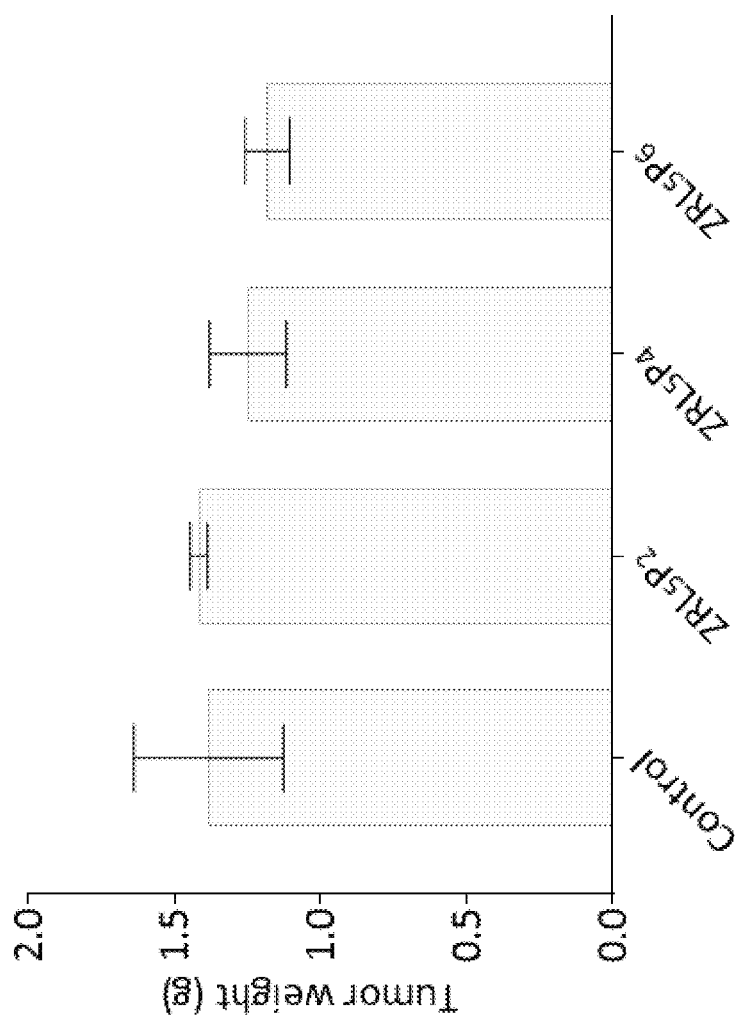
Figure 24D:
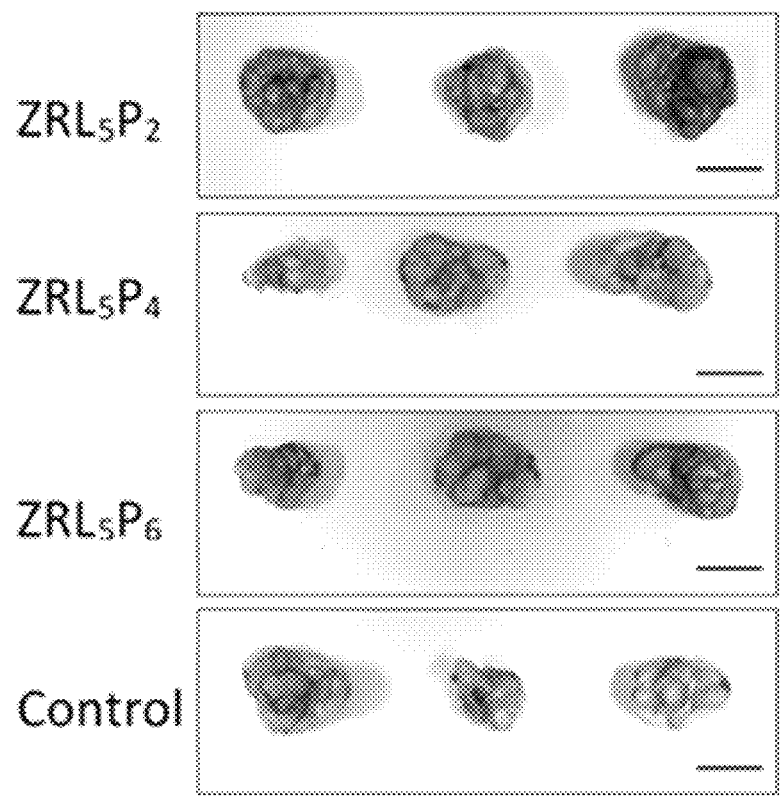

In order to verify if the EBV particles could be actually generated by $ZRL_5P_4$, the recombinant EBV-containing HONE-1 (HONE-1-EBV) cell line was used. The presence of the virions was detected by infecting Raji cells (an established B-cell line), because the recombinant EBV genome encodes a green fluorescence protein (GFP), the GFP-expressing Raji cells reflect the production of virions by the HONE-1-EBV cells. As can be seen, 10 µM $ZRL_5P_4$ could lead to the production of virions and which is 10.4-fold more than the DMSO control (p=0.009), and is ~4-fold more than the NLS-null version $ZRL_5P_2$ (p=0.006) (FIG. 22A-B). Although the viral titer of $ZRL_5P_4$ was 2.6-fold higher than the solvent control but the difference is not significant (p=0.06). Taken together, the entry of $ZRL_5P_4$ into EBV-infected cells can induce the reactivation of EBV and release of the virions, and which can mediate shrinkage of the transplanted C666-1 tumors (FIG. 20A-E) by causing the cell death of these tumor cells when exposed to $ZRL_5P_4$.

Discussion

Despite the effort spent on identifying and testing various well-known and novel EBV lytic inducing agents over recent decades, no specific agent against EBV genes or proteins has been established. The $ZRL_5P_4$ probe might represent the first of its type to specifically disrupt the EBNA1 protein and to potently reactivate EBV from latency, leading to tumor cell lysis and/or induction of viral proteins that can be targeted by immune cells and anti-viral agents to eliminate EBV-infected tumor cells. The strategy of targeted reactivation of the latent viral genome and induction of cytotoxic effects in virus-driven tumors is known as cytolyticvirus activation (CLVA) therapy, and some EBV lytic inducers have recently entered phase I/II clinical trials. In addition, the in vivo administration of $ZRL_5P_4$ was demonstrated to shrink the subcutaneous tumors, and the IHC staining results indicated that the necrotic tumor tissues might be due to an induction of EBV lytic cycle. The EBV early and late lytic gene/protein expression analyses and the in vitro RAJI cell infection assay have shown that $ZRL_5P_4$ could specifically induce the viral reactivation, which might result in tumor cell viability (as reflected by the MTT assay) and shrinkage of the EBV-associated tumors (derived from C666-1 cells) by disruption of the functional EBNA1 dimer. In concordance to this finding, it was reported that the depletion of EBNA1 gene expression by small interfering RNA (siRNA) in the EBV-infected epithelial cell lines could activate spontaneous lytic cycle induction, indicating that EBNA1 has a functional role in suppressing reactivation of EBV. The association of PML proteins and EBNA1 might provide an explanation of how $ZRL_5P_4$ can induce the EBV lytic cycle. As can be seen from the current and other studies, it has become clear that EBNA1 is not limited to maintain the stable persistence of EBV episomes and it is also involved in other cellular functions including regulation of the viral reactivation which contribute to the cell proliferation and survival. The present report represents one of the few studies to demonstrate the functional role of EBNA1 and EBV in the in vivo tumor formation and lytic induction.

As mentioned earlier, previous studies show that $Zn^{2+}$ is essential for EBNA1 to cooperatively activate the oriP-associated transcription and dimerize through the amino-terminal domain. The current results of EBNA1 dimerization and oriP reporter assays are in concordance with their results, as the zinc chelator in $ZRL_5P_4$ could further disrupt both the self-association of the EBNA1 monomers and the closely related transactivation activity, as well as the cell viability and the EBV lytic gene induction. For the EBNA1 self-association analysis, in the absence of $Zn^{2+}$ there was no significant difference in the inhibition between the $ZRL_5P_4$ and $L_2P_4$ (lack of zinc chelator) treatments; but when $Zn^{2+}$ was present, $ZRL_5P_4$ was more efficient to inhibit the dimer formation (FIGS. 18A and 18B). As aforementioned, the UR1 region in EBNA1 coordinates $Zn^{2+}$ through a pair of essential cysteine and this coordination of $Zn^{2+}$ is essential for UR1 to form a second EBNA1 dimerization site in addition to the first dimerization site at the DBD. The presence of $Zn^{2+}$ likely contributes to the increased affinity of the full length of two adjacent EBNA1 monomers. Thus, $ZRL_5P_4$ may interrupt both dimerization interfaces at UR1 and the DBD, whereas $L_2P_4$ can only interfere with the dimerization site at the DBD. As shown in the current results of MD simulations and fluorescence titration, the presence of $Zn^{2+}$ did not affect $ZRL_5P_4$ to bind with the EBNA1 DBD. The DBD region is supposed to have no binding residues of $Zn^{2+}$, so this binding of $ZRL_5P_4$ with the DBD is solely due to the $P_4$ peptide present in the probe. It implies that the additional inhibitory effects contributed by the zinc chelator is not directly related with the DBD.

The increased potency of $ZRL_5P_4$ on the various EBNA1 and cellular activities upon $L_2P_4$ is also reflected by the cellular imaging for the EBV-positive cell lines. The imaging results can explain that the stronger inhibition attributes to the nuclear localization of the probe, where EBNA1 is primarily located, and that nuclear EBNA1 was of critical importance for its dependent function. In contrast, a major proportion of $L_2P_4$ is located in the cytoplasm, the remaining probe is located in the nucleus. As can be seen, the new bioprobe $ZRL_5P_4$ can selectively enter the nuclei of EBV-positive cells and can disrupt the function of EBNA1 more effectively than $L_2P_4$. Both the NLS RrRK sequence and the zinc chelator in $ZRL_5P_4$ play a critical role in enhancing the more specific binding to the nuclear EBNA1 protein and/or facilitating the entry to the nucleus.

On the other hand, the inventor initially thought that the genetic variation at the EBNA1 dimerization sequence (the amino acid 563) could be an important factor to design the EBNA1 probes. $ZRL_5P_6$ was constructed to target the EBNA1 protein with an "I" residue at the variation position. However, the experimental results of various biological assays show that both $ZRL_5P_4$ and $ZRL_5P_6$ were equally effective in all these assays, indicating that this amino acid residue is not critical for disrupting the self-association of the EBNA1 monomer. These findings suggest that $ZRL_5P_4$ and $ZRL_5P_6$ should be equally potent for suppressing the EBNA1 proteins in various EBV stains.

In conclusion, $Zn^{2+}$ has been made use of as an important co-factor for EBNA1 to function and have constructed a new series of EBNA1 probes with a zinc chelator and an EBNA1 binding peptide. The zinc chelator can further enhance the inhibitory activities of the functional self-associated EBNA1 dimer and the associated oriP-associated transactivation. Interestingly, the new $ZRL_5P_4$ probe could reactivate the EBV lytic induction which is associated with the shrinkage of EBV-positive tumors in the animal model. This is the first study to successfully target a single protein (EBNA1) to induce the EBV lytic cycle. As EBNA1 is a foreign protein to the host, in theory, this strategy of elimination of EBV-associated tumor cells warrants absolute specificity over all other lytic induction therapies. The current lytic analysis results also suggest that the function of EBNA1 as well as the role of EBV is associated with maintenance of tumor cell survival through suppression of the lytic cycle reactivation.

Experimental

General.

Unless otherwise stated, all chemicals were used as purchased without further purification. Full-length EBNA1 with an N-terminal His tag was purchased from Abcam (ab138345). Solvents were dried using standard procedures. Purification of $ZRL_5P_2$, $ZRL_5P_4$, and $ZRL_5P_6$ was performed on a Waters semi-preparative HPLC system. NMR spectra were recorded on a Bruker400 MHz NMR spectrometer, and the chemical shifts were referenced internally to tetramethylsilane or the corresponding solvent residues in parts per million (ppm); coupling constants are reported in hertz (Hz). High-resolution mass spectra, reported as m/z, were obtained on either a Bruker Autoflex MALDI-TOF or an Agilent 6450 UHD Accurate-Mass Q-TOF spectrometer. UV-visible absorption spectra were recorded on a Cary 8454 spectrometer.

Syntheses.

All new compounds were characterized by $^1H$ and $^{13}C$ NMR spectroscopy and HR MALDI-TOF MS.

Molecular Dynamics Simulation.

All-atom unbiased MD simulations in AMBER 14 with aff99SBildn force field were used. The system preparation and simulation procedures were the same as those reported previously. In brief, a periodic boundary, cubic, TIP3 explicit water box with a 20 Å buffer was used with charge neutralized by adding Cl⁻ ions. The system was then minimized and equilibrated by sander using three stages: (1) heating from 100 to 300 K in 20 ps; (2) adjusting the solvent density to 1 g/mL in 20 ps; and (3) equilibrating in 200 ps with NPT ensemble. A subsequent 100 ns NPT simulation was performed with CUDA-accelerated PMEMD. A 2 fs time step and SHAKE-enabled settings were used for all of the equilibration and production stages. A Berendsen thermostat was adopted for temperature control at all stages.

Luminescence Measurements.

Luminescence, excitation and emission spectra were recorded on a Horiba Fluorolog-3 spectrofluorometer equipped with a xenon lamp. Specifically, a luminescence titration assay of the selectivity of $ZRL_5P_4$ for metal ions was performed in HEPES buffer (0.05 M, pH 7.4)/$CH_3CN$ (50:50) using perchlorate salts as the metal source [Zn$(ClO_4)_2$, Cd$(ClO_4)_2$, Cu$(ClO_4)_2$, Co$(ClO_4)_2$, Ni$(ClO_4)_2$, Hg$(ClO_4)_2$ and Mg$(ClO_4)_2$]. The luminescence titration assay of the selective binding of $ZRL_5P_4$ with proteins was conducted in phosphate-buffered saline (PBS). Luminescence titration experiments were performed by gradually increasing the concentration of the analytes in the aqueous solution of $ZRL_5P_4$, such as $Zn^{2+}$, EBNA1 and HSA; the experiment was stopped when the change in $ZRL_5P_4$ luminescence ceased.

Expression and Purification of EBNA1 DBD.

Plasmids for the expression of EBNA1 DBDs of amino acids 379-641 fused with glutathione S-transferase were expressed in *Escherichia coli* and purified with glutathione sepharose 4B rinse (GE Dharmacon).

MBS-Cross-Linked Dimerization Assay.

Full-length EBNA1 (residues 1-641) with an N-terminal His tag (ab138345, Abcam) was used in this assay. Each 5 μg of EBNA1 was incubated without or with 10 μM $Zn^{2+}$ at room temperature in the presence of the cross-linking reagent 3-maleimidobenzoylN-hydroxysuccinimide ester (MBS) and probe (buffer/$L_2P_4$/$ZRL_5P_4$) for 2 h to allow the pre-existing dimer to be covalently cross-linked. After incubation, SDS loading buffer was added to each system, which were then separated using denaturing SDS-PAGE, transferred onto a nitrocellulose membrane, which was blotted with antibody; the obtained protein bands provided information of dimerization inhibition.

Luciferase Reporter Assay for EBNA1-oriPI Dependent Transactivation.

To study EBNA1-dependent transactivation, the luciferase vector J988F containing the EBV C promoter and oriPI (family of repeats, FR) was constructed. The EBV C promoter and oriPI (nucleotides 7447-11412) regions were subcloned from the previously described plasmid pgCp(−3889)CAT as a HindIII fragment into the pGL3Basic luciferase vector (Promega). Correct sequences were ascertained by Sanger sequencing using the ABI PRISM Big Dye terminator cycle sequencing kit (Applied Biosystems). EBV-positive C666-1 and NPC43 cells were then transiently transfected with the J988F reporter plasmid. Cells were seeded in 12-well plates and co-transfected with the J988F plasmid (2 μg/well) and a pRL Renilla luciferase control reporter (500 ng/well) (Promega) using Lipofectamine 2000 (Invitrogen). After 24 h, the cells were treated with $ZRL_5P_4$, $L_2P_4$, EDTA or TPEN (10 μM) for another 8 h. Cells were lysed with Passive Lysis Buffer (Promega), and the lysate was then transferred onto a white, opaque, 96-well plate. The luciferase activities were measured using the Dual Luciferase Reporter Assay System (Promega) with the Glo-Max 96 Microplate Luminometer (Promega). The pRL Renilla luciferase reporter was used as an internal control to normalize the transfection efficiency among the samples.

Cell Culture.

Five cell lines were used in this work: the EBV-negative HK-1 and HONE-1 lines and the EBV-positive NPC43, C666-1and Raji lines. HK-1, HONE-1, C666-1 and Raji cells were grown in RPMI 1640 medium supplemented with 10% fetal bovine serum (FBS), 1% penicillin and streptomycin at 37° C. and 5% $CO_2$. NPC43 cells were maintained in RPMI 1640 with 10% FBS and 4 μM Y27362 (inhibitor of Rho-associated, coiled-coil-containing protein kinase; Enzo Life Sciences).

MTT Assay.

All cells were sub-cultured in 96-well plates at the optimal growth density (HK-1, $1\times10^4$ cells/100 μl per well; HONE-1, $8\times10^3$ cells/100 μl per well; NPC43, $8\times10^3$ cells/100 μl per well; C666-1, $3\times10^4$ cells/100 μl per well; Raji, $1\times10^4$ cells/100 μl per well) for 24 h. The growth medium was then replaced by solutions of $ZRL_5P_2$, $ZRL_5P_4$, or $ZRL_5P_6$ at concentrations of 1, 5, 10, 20, 50 and 100 μM for EBV-negative cells, or at concentrations of 1, 3, 5, 10, 15 and 20 μM for EBV-positive cells (for the suspensions of C666-1 and Raji cells, the 96-well plate was centrifuged at 1000 rpm for 3 min before each replacement/withdrawal of medium and operated with care during the assay). After culturing for a further 5 days (half of the volume of medium was replaced every 4 days with fresh medium containing the appropriate drug concentration), the cells were rinsed with PBS and then incubated with a solution of 3-(4,5-dimethylthiazol-2-yl)-2,5-diphenyltetrazolium bromide (MTT, 0.5 mg/ml, 50 μl) in PBS at 37° C. for 3 h. Then, 70% of the medium was carefully removed, DMSO (100 μl) was added, and the plate was shaken for 30 min to solubilize the formazan produced by the living cells. The optical densities were measured with a dual-wavelength Labsystem Multiskan microplate reader (Merck Eurolab) at wavelengths of 540 and 690 nm and expressed as a percentage relative to control cells (cells without drug treatment served as the control). Measurements were performed in triplicate and repeated twice. Cell viability (%) was calculated according to Eq. (2):

$$Viability(\%) = (OD_t/OD_c) \times 100\% \qquad (2)$$

Where $OD_t$ and $OD_c$ are the optical densities of the surviving cells treated with or without drug, respectively.

Two-Photon Imaging and Co-Staining.

Cells were incubated with $ZRL_5P_2$/$ZRL_5P_4$/$ZRL_5P_6$ (10 μM) for 3 h and then co-stained with DRAQ5 (5 μM) for 30 min. Images were acquired using a Leica TCS SP8 confocal laser-scanning microscope equipped with a coherent femtosecond laser (680-1050 nm), argon laser (432, 457 and 488 nm), He—Ne laser (632 nm), ultraviolet lamp and a controlled $CO_2$-content stage-top tissue culture chamber (37° C., 2-7% $CO_2$). In vitro images of $ZRL_5P_2$/$ZRL_5P_4$/$ZRL_5P_6$ were obtained under two-photon excitation ($\mu_{ex}$=700 nm), whereas images of DRAQ5 were acquired under single-photon excitation ($\mu_{ex}$=638 nm).

Nude Mice Xenograft and Intratumoral Injection.

C666-1 cells ($8\times10^6$) suspended in 100 μl of serum-free RPMI medium were injected into the right flanks of 6- to 8-week-old male BALB/c nude mice. After 21 days of inoculation, when tumor shad grown to an average volume of approximately 220 mm³, mice were assigned to treatment groups (n=5 per group) such that the average tumor volumes varied between groups by no more than 10%. Twice weekly, mice received 4 µg/tumor intra-tumoral injections of $ZRL_5P_2$, $ZRL_5P_4$, or $ZRL_5P_6$ in 0.1% using a 29-gauge syringe. Mice that received an equivalent volume of 0.1% DMSO alone served as controls. The treatment period lasted for 18 days. Body weight and tumor volumes were measured twice weekly, and tumor volumes were calculated as (length×width$^2$)/2. At the end of the treatment period, mice were sacrificed, and their tumors and major organs were harvested and weighed. The investigators were blind to treatment grouping during the experiments and analysis of data. All animal experiments were approved by the Department of Health of the Hong Kong Government and the Animal Subjects Ethics Sub-Committee of Hong Kong Polytechnic University.

Quantitative Polymerase Chain Reaction Gene Expression Analysis.

qPCR was performed as reported.

Western Blot Analysis.

Western blot analysis of BRLF1 (Rta), BMRF1, and gp350/220 was performed as reported. The Rta antibody was supplied from Argene (Verniolle, France) and the β-actin antibody for loading control was supplied from Cell Signaling Technology (Danvers, Mass., US). Antibodies against BMRF1 and gp350/220 were generously given by Prof Jaap M. Middeldorp (VU University Medical Center, The Netherlands). A 1:400 dilution of the primary antibodies was used.

Preparation of Formalin-Fixed, Paraffin-Embedded (FFPE) Tumor Tissues, Hematoxylin and Eosin (H & E) Stain, and Immunohistochemistry (IHC)

The transplanted tumor tissues were fixed with formalin, and embedded in paraffin accordingly to the general practice. The histologic sections were prepared and stained with H & E. The lytic protein markers were stained with IHC antibodies against Zta and dBMF1. The BZLF1 (Zta) antibody was supplied from Argene and the BMRF1 antibody was the one used for Western blot analysis. The slides were incubated with the primary antibodies (1:100 dilution) for IHC as previously described.

EBV Infection Assay

The HONE-1-EBV cell line was used to produce the infectious EBV particles for the lytic analysis, this cell line was generated by introducing a green fluorescent protein (GFP) open reading frame in the recombinant Akata EBV genome into the EBV-negative NPC cell line HONE-1. The procedures of production of viral particles and quantitation of virus titers were followed as previously described. In brief, after incubation with various EBNA1 probes for 96 hours, the supernatants were filtered through 0.45 µM pore filters and the viral particles were enriched by centrifugation at 20,000 g for 2 hours. The relative virus titers were determined by the Raji cell assay and were quantified with the GFP expression of Raji cells infected with the virus stocks to be analyzed. The Raji cells (1×10$^5$) were incubated in 96-well plates and cultivated for 3 days at 37° C. to allow expression of GFP. The number of GFP-positive cells was counted by ultraviolet microscopy.

Synthesis of diethyl 4-nitrobenzylphosphonate (1)

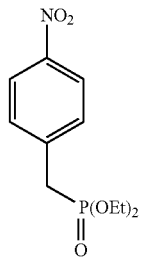

1

Synthesis of diethyl 4-nitrobenzylphosphonate (1). Compound 1 was prepared according to a previous report. A mixture of 4-nitrobenzyl bromide (200 mg, 0.93 mmol) and triethylphosphite (216 mg, 1.30 mmol) was heated at 160° C. under a nitrogen atmosphere for 2 h. Excess triethylphosphite was removed under reduced pressure to provide 1 as a brown oil (241 mg, 95%). $^1$H NMR (400 MHz, CDCl$_3$): δ 8.19 (dd, J=8.8, 0.8 Hz, 2H), 7.48 (dd, J=8.8, 2.4 Hz, 2H), 4.07 (dq, J=7.6, 0.4 Hz, 2H), 4.05 (dq, J=7.6, 0.4 Hz, 2H), 3.25 (d, J=22.4 Hz, 2H), 1.27 ppm (t, J=6.8 Hz, 6H); $^{13}$C NMR (100 MHz, CDCl$_3$): δ 139.7 (d, $^2J_{(C,P)}$=8.9 Hz), 130.6 (d, $^3J_{(C,P)}$=6.4 Hz), 123.7 (d, $^4J_{(C,P)}$=2.9 Hz), 62.4 (d, $^2J_{(C,P)}$=6.7 Hz), 34.0 (d, $^1J_{(C,P)}$=136.7 Hz), 16.4 ppm (d, $^3J_{(C,P)}$=5.9 Hz); HRMS (MALDI-TOF): m/z: calcd for $C_{11}H_{16}NO_5P$ 273.0766 [M]$^+$; found: 273.0755.

Synthesis of di-(2-picolyl)amine (2)

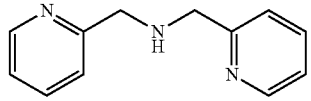

2

A solution of 2-picolylamine (5.0 g, 46.24 mmol) in absolute EtOH (100 ml) was added dropwise to a suspension of 2-pyridinecarboxaldehyde (4.9 g, 46.05 mmol) in absolute EtOH (100 ml) at 0° C. After the addition, the reaction solution was stirred for 4 h and then cooled to 0° C. NaBH$_4$ (3.5 g, 92.10 mmol) was added into the cooled solution in small portions. The reaction was stirred for another 12 h at room temperature. Then, HCl (5 N, 120 ml) was added slowly and the mixture was stirred for 1 h. Aqueous NaOH (2 N) was then added until the pH reached 11. The mixture was extracted with DCM (6×50 ml), and the combined organic phases were dried over anhydrous MgSO$_4$ and filtered. Removal of the solvent afforded 2 in analytical purity as a brown oil (7.8 g, 85%). $^1$H NMR (400 MHz, CD$_3$OD): δ 8.49 (qd, J=4.8, 0.8 Hz, 2H), 7.81 (dt, J$_1$=7.6, 1.6 Hz, 2H), 7.51 (d, J=8.0 Hz, 2H), 7.31 (m, 2H), 3.93 ppm (s, 4H); $^{13}$C NMR (100 MHz, CD$_3$OD): δ 160.3, 149.8, 138.7, 124.1, 123.8, 54.8 ppm; HRMS (MALDI-TOF): calcd for $C_{12}H_{14}N_3$ 200.1188 [M+H]$^+$; found: 200.1326.

Synthesis of (E)-methyl 4-(4-nitrostyryl)benzoate (3)

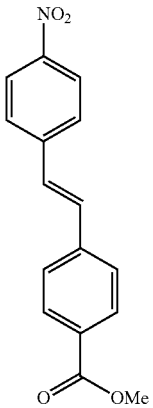

A solution of diethyl 4-nitrobenzylphosphonate (200 mg, 0.73 mmol) and methyl 4-formylbenzoate (120 mg, 0.73 mmol) in THF (3 ml) was added to a suspension of sodium methoxide (79 mg, 1.46 mmol) in THF (6 ml). The mixed solution was stirred for 20 min at 0° C. The solvent was removed under reduced pressure. $H_2O$ (100 ml) was added, and the resulting aqueous solution was neutralized with HCl (0.1 N), followed by extraction with DCM (3×50 mL). The combined organic phases were dried over anhydrous $MgSO_4$ and filtered. Then, the solvents were removed under reduced pressure. The pure product 3 (yellow solid) was obtained by filtering the crude material through silica gel with DCM as the eluent (182 mg, 88%). $^1H$ NMR (400 MHz, $CDCl_3$): δ 8.25 (dd, $J_1$=6.8, 2 Hz, 2H), 8.07 (dd, $J_1$=6.8, 1.6 Hz, 2H), 7.67 (dd, $J_1$=7.2, 2 Hz, 2H), 7.61 (d, J=8.4 Hz, 2H), 7.28-7.26 (2H, coincided with residual $CHCl_3$), 3.94 ppm (s, 3H); $^{13}C$ NMR (100 MHz, $CDCl_3$): δ 166.7, 147.2, 143.2, 140.5, 132.1, 130.2, 130.0, 128.7, 127.2, 126.9, 124.2, 52.2 ppm; HRMS (MALDI-TOF): m/z: calcd for $C_{16}H_{14}NO_4$ 284.0923 $[M+H]^+$; found: 284.0895.

Synthesis of (E)-methyl 4-(4-aminostyryl)benzoate (4)

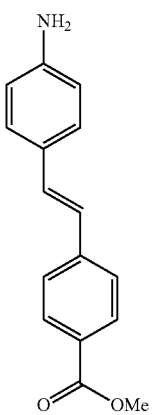

A solution of 3 (200 mg, 0.71 mmol) in EtOAc (10 ml) was stirred under a nitrogen atmosphere at 75° C. Stannous chloride dihydrate (801 mg, 3.55 mmol) was added and the mixture was heated at 75° C. and stirred overnight. After the reaction was complete (determined by TLC, thin-layer chromatography), the mixture was allowed to cool to room temperature, followed by the addition of aqueous $NaHCO_3$ until the pH reached 8. The suspension was filtered through a pad of celite and washed with EtOAc. The filtrate was washed with $H_2O$ (twice) and brine, then dried over anhydrous $MgSO_4$ and filtered and concentrated under reduced pressure to afford 4 as an orange-yellow solid (144 mg, 80%). $^1H$ NMR (400 MHz, $CDCl_3$): δ 7.99 (d, J=8.0 Hz, 2H), 7.51 (d, J=8.4 Hz, 2H), 7.36 (d, J=8.4 Hz, 2H), 7.13 (d, J=16.4 Hz, 1H), 6.93 (d, J=16.4 Hz, 1H), 6.69 (d, J=8.4 Hz, 2H), 3.92 ppm (s, 3H); $^{13}C$ NMR (100 MHz, $CDCl_3$): δ 167.0, 146.7, 142.6, 131.3, 130.0, 128.2, 128.1, 127.4, 125.8, 123.8, 115.2, 52.0 ppm. HRMS (MALDI-TOF): m/z: calcd for $C_{16}H_{15}NO_2$ 253.1103 $[M]^+$; found: 253.1084.

Synthesis of (E)-methyl 4-[4-(2-chloroacetamido) styryl]benzoate (5)

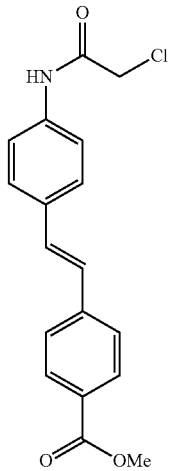

A solution of 2-chloroacetyl chloride (53 mg, 0.47 mmol) in DCM (3 ml) was added dropwise to a solution of 4 (100 mg, 0.39 mmol) and 4-(dimethylamino)pyridine (81 mg, 0.66 mmol) in DCM (15 ml) at 0° C. and stirred under a nitrogen atmosphere. After stirring for 2 h at room temperature, the solvent was removed under reduced pressure. The obtained pale-yellow solid was purified by silica gel with DCM as the eluent to give 5 as an orange solid (109 mg, 85%). $^1H$ NMR (400 MHz, $CDCl_3$): δ 8.28 (s, 1H), 8.03 (d, J=8.4 Hz, 2H), 7.60-7.53 (m, 6H), 7.19 (d, J=16.4 Hz, 1H), 7.09 (d, J=16.4 Hz, 1H), 4.22 (s, 2H), 3.93 ppm (S, 3H); $^{13}C$ NMR (100 MHz, $CDCl_3$): δ 167.8, 163.7, 141.7, 136.5, 133.7, 130.2, 130.0, 128.9, 127.5, 127.3, 126.2, 120.1, 52.1, 42.9 ppm; HRMS (MALDI-TOF): m/z: calcd for $C_{18}H_{16}ClNO_3$ 329.0819 $[M]^+$; found: 329.0807.

Synthesis of (E)-methyl 4-(4-{2-[bis(pyridine-2-ylmethyl)amino]acetamido}styryl)benzoate (6)

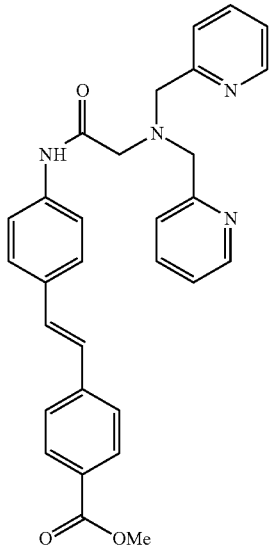

Compound 5 (50 mg, 0.15 mmol), di(2-picolyl)amine (DPA, 36 mg, 0.18 mmol), N,N-diisopropylethylamine (DIPEA, 33 mg, 0.26 mmol), and potassium iodide (16 mg, 0.67 mmol) were added to MeCN (25 ml). After stirring and heating at reflux overnight under a nitrogen atmosphere, the mixture was allowed to cool to room temperature, and the solvent was removed under reduced pressure to give a yellow-brown solid. The crude material was then purified by silica gel column chromatography using DCM/MeOH (100:1; the DCM was extracted with aqueous $NH_3$ before use, DCM/$NH_3$ 200:1 v/v) to obtain 6 (59 mg, 80%). $^1$H NMR (400 MHz, $CDCl_3$): δ 11.04 (s, 1H), 8.64 (qd, $J_1$=4.8, 0.8 Hz, 2H), 8.02 (d, J=8.4 Hz, 2H), 7.82 (d, J=8.4 Hz, 2H), 7.64 (dt, J=7.6, 2.0 Hz, 2H), 7.56 (d, J=8 Hz, 2H), 7.53 (d, J=8.4 Hz, 2H), 7.29 (d, J=7.6 Hz, 2H), 7.22-7.18 (m, 3H), 7.07 (d, J=16.4 Hz, 1H), 3.95 (s, 4H), 3.93 (S, 3H), 3.49 ppm (S, 2H); $^{13}$C NMR (100 MHz, $CDCl_3$): δ 169.8, 166.9, 158.0, 149.4, 142.0, 138.7, 136.7, 132.2, 130.8, 130.0, 127.4, 126.2, 126.1, 123.3, 122.6, 119.8, 60.4, 58.7, 52.1 ppm; HRMS (MALDI-TOF): m/z: calcd for $C_{30}H_{28}N_4NaO_3$ 515.2059 [M+Na]$^+$; found: 515.2654.

Synthesis of $ZRL_5$ (7)

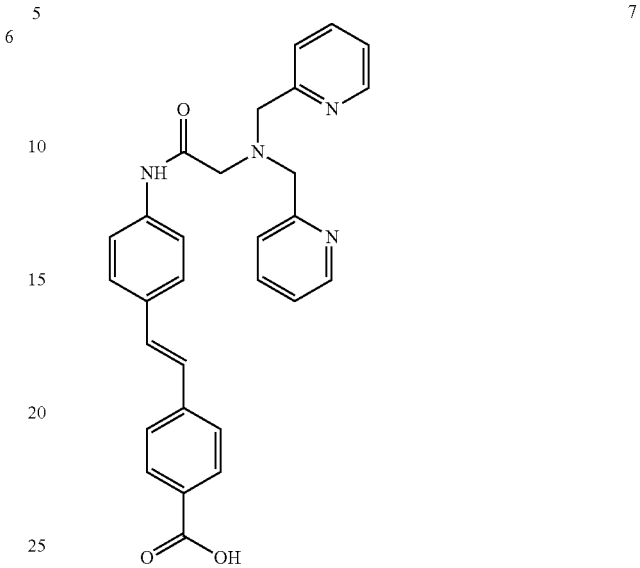

Synthesis of $ZRL_5$ (7). KOH (114 mg, 2.03 mmol) was added to a suspension of 6 (200 mg, 0.41 mmol) in EtOH/$H_2O$ (1:1, 8 ml). After stirring and heating at reflux overnight, the reaction mixture was allowed to cool to room temperature. The solvent volume was reduced to approximately 50%, and then HCl (1 N) was added until the solution became acidic. The resulting precipitate was filtered and collected to give 7 as a yellow solid (157 mg, 78%). $^1$H NMR (400 MHz, $CDCl_3$): δ 10.74 (s, 1H), 8.68 (d, J=4.4 Hz, 2H), 8.00 (d, J=8.4 Hz, 2H), 7.73 (d, J=8.4 Hz, 2H), 7.67 (dt, J=7.6, 1.6 Hz, 2H), 7.51 (d, J=8.4 Hz, 2H), 7.43 (d, J=8.8 Hz, 2H), 7.33 (d, J=7.6 Hz, 2H), 7.26-7.22 ppm (m, 2H), 7.16 (d, J=16.4 Hz, 1H), 7.02 (d, J=16.4 Hz, 1H), 4.02 (s, 4H), 3.54 ppm (s, 2H); $^{13}$C NMR (100 MHz, $CDCl_3$): δ 169.4, 157.4, 149.1, 142.4, 138.5, 137.2, 132.4, 130.9, 130.5, 127.3, 126.3, 126.1, 123.7, 122.9, 120.1, 60.3, 59.0 ppm; HRMS (MALDI-TOF): m/z: calcd for $C_{29}H_{26}N_4NaO_3$ 501.1903 [M+Na]$^+$; found: 501.1902.

Synthesis of $ZRL_5P_2$/$ZRL_5P_4$/$ZRL_5P_6$

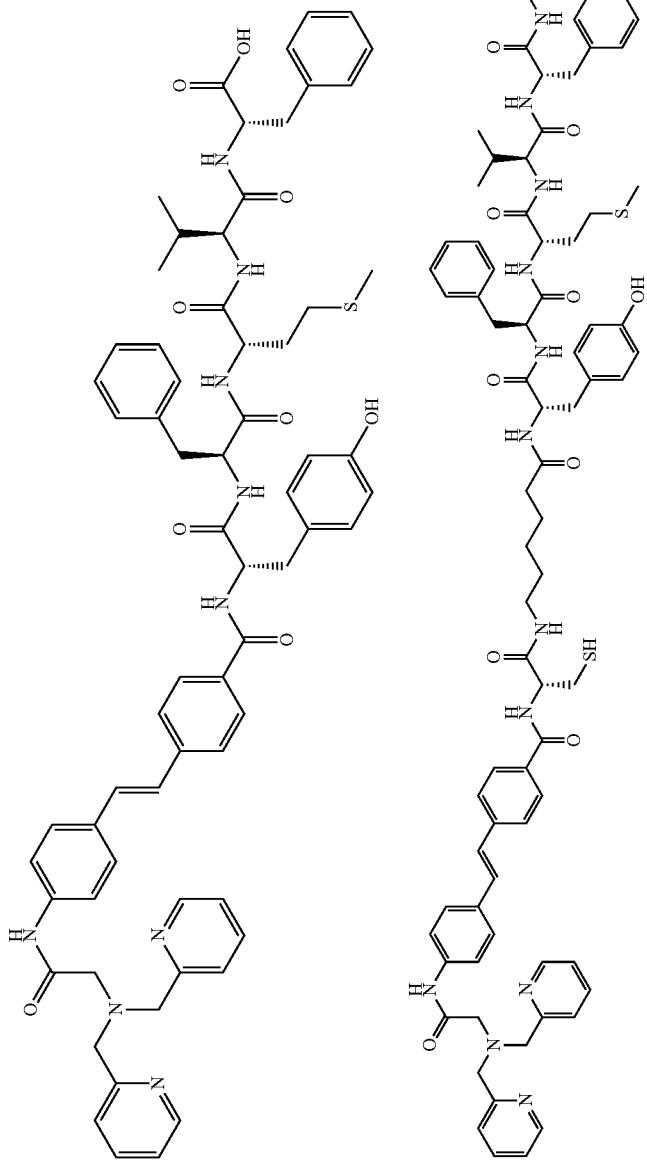

Conjugation.

A solution of 7 (148 mg, 0.30 mmol) and (benzotriazol-1-yloxy)tripyrrolidinophosphonium hexafluorophosphate (PyBOP, 156 mg, 0.3 mmol) was dissolved in DMF (3 ml). DIPEA (90 mg, 0.70 mmol) was added and the solution was stirred for 1 min. The solution was added to the appropriate peptide ($P_2/P_4/P_6$, 0.1 mmol) loaded onto Wang resin on an 8 ml solid-phase extraction (SPE) cartridge with PE frits. The peptide resin was allowed to swell in DMF overnight, and the chamber was drained before addition. The resulting mixture was agitated on a shaker for 45 min, and the solution was then filtered and washed with DMF three times. A second round of coupling was performed according to the same procedures, and a blank coupling cycle with PyBOP (156 mg, 0.3 mmol) and DIPEA (90 mg, 0.70 mmol) in DMF (3 mL) was performed. After 45 min, the solution was filtered and washed as described above.

Cleavage of the resin. A mixture of TFA/$H_2O$/TIPS (0.95:0.25:0.25; TFA, trifluoroacetic acid; TIPS, triisopropylsilane) was added to the crude resin shrunken with diethyl ether. The mixture was agitated on a shaker for 3 h. The resin was then removed by filtration and washed with MeOH three times. The combined filtrate was then concentrated under reduced pressure to give the crude $ZRL_5P_2$/$ZRL_5P_4$/$ZRL_5P_6$, which was then purified by preparative HPLC (Table 2).

The compounds provided herein can be purified using any conventional purification technique. In certain embodiments, the compounds provided herein are purified using preparative HPLC. Table 2 below exemplary preparative HPLC purification conditions.

TABLE 2

The gradient of the solvent for preparative HPLC. Solvent A is DI $H_2O$ with 0.5% TFA, and solvent B is HPLC grade MeCN.

| Time/min | Flow/ml · min | % A | % B |
|---|---|---|---|
| 0 | 8 | 80 | 20 |
| 35 | 8 | 20 | 80 |
| 37 | 8 | 0 | 100 |
| 40 | 8 | 80 | 20 |

$ZRL_5P_2$.

Retention time, 24.061 min. HRMS (Q-TOF): calcd for $[M+H]^+$ 1166.5174, found: 1166.5195; calcd for [M+2H]/2 583.7626, found: 583.7619.

$ZRL_5P_4$.

Retention time, 16.845 min. HRMS (MALDI-TOF): calcd for [M+H] 2094.0552, found: 2094.2452.

$ZRL_5P_6$.

Retention time, 17.319 min. HRMS (Q-TOF): calcd for [M+2H]/2 987.0487, found: 987.0501; calcd for [M+3H]/3 658.3684, found: 658.3686; calcd for [M+4H]/4 494.0282, found: 494.0280.

DSS-Cross-Linked Dimerization Assay.

Full-length EBNA1 (a.a. 1-641) with N-terminal His tag (ab138345, Abcam) was used in this assay. Each 5 Dg of EBNA1 was incubated without (−) or with (+) $Zn^{2+}$ at room temperature in the presence of DSS-cross-linker and analyzed probes (buffer/$L_2P_4$/$ZRL_5P_4$) for 2 hours to allow a preexisting dimer to be covalently cross-linked. After incubation, SDS loading buffer was added to each system, which were separated on SDS-PAGE denaturing gel, transferred onto the nitrocellulose membrane, and blotted with antibody, with the obtained protein bands providing information on dimerization inhibition.

Molecular Dynamic (MD) Simulations

Modeling and Simulations of $P_4$-EBNA1 Complex.

$P_4$ (CAhxYFMVFGGRrRK, SEQ ID NO:4) was docked into the dimeric interface of the putative EBNA1 DBD monomer from a previous work with the online CABS-dock tool. 10 $P_4$-EBNA1 complex models were generated and subjected to constant pressure and temperature (NPT) simulations in AMBER 14 with CUDA acceleration. Through observing the fluctuation of $P_4$ in the each complex (data not shown), the most stable complex model was chosen and subjected to an additional 500 ns NPT simulations. The results showed that $P_4$ stably occupied the dimeric interface of the putative EBNA1 DBD monomer, suggesting it is a potent EBNA1 dimerization inhibitor (FIG. 7A-F). The representative $P_4$-EBNA1 DBD monomer complex structure was obtained with the conformational clustering analysis. Well consistent with the previous work, the hydrophobic packing effect mediated by YFMVF (SEQ ID NO:2) and the salt bridging formed by RrRK contributed to the $P_4$-EBNA1 DBD monomer binding (FIG. 16).

Modeling of $Zn^{2+}$-$ZRL_5$ Complex.

The 3D models of $ZRL_5$ in both $Zn^{2+}$-free (denoted as L5 in FIGS. 8 and 17) and $Zn^{2+}$-coordinated (denoted as $Zn^{2+}$-L5 in FIGS. 8 and 17) scenarios were built by the Molecular Operation Environment (MOE, version 2012.10). MMFF94x force field (FF) was used to minimize the energy, besides, the LowModeMD was employed to identify the global energy minimum conformation (FIG. 8A-E). The partial charge of $ZRL_5$ and $Zn^{2+}$-$ZRL_5$ was calculated by online RED server, and their atom types were manually determined with output from parmchk tool (FIG. 17A-D). Besides, the missing FF parameters of $ZRL_5$ and $Zn^{2+}$-$ZRL_5$ were determined from comparable atoms in GAFF or measurements of RED-derived results (Table 3 and Table 4).

TABLE 3

The modified AMBER force field parameters for zinc-free $ZRL_5$ residues.

| Non-standard residues | Type | Item | Parameters |
|---|---|---|---|
| $ZRL_5$ | Bonded | CA-CD | k = 361.3 kcal/(mol*Å$^2$), $d_0$ = 1.4763 Å |
| | | CA-N | k = 384.2 kcal/(mol*Å$^2$), $d_0$ = 1.4121 Å |
| | Angle | CA-C-N | k = 67.68 kcal/(mol*rad$^{-2}$), $\theta_0$ = 115.25 |
| | | CA-C-O | k = 68.72 kcal/(mol*rad$^{-2}$), $\theta_0$ = 122.60 |
| | | CA-CA-CD | k = 64.50 kcal/(mol*rad$^{-2}$), $\theta_0$ = 120.82 |
| | | CA-CA-N | k = 67.87 kcal/(mol*rad$^{-2}$), $\theta_0$ = 120.19 |
| | | CA-CA-NC | k = 68.83 kcal/(mol*rad$^{-2}$), $\theta_0$ = 122.94 |
| | | CT-CA-NC | k = 67.30 kcal/(mol*rad$^{-2}$), $\theta_0$ = 116.68 |
| | | H4-CA-NC | k = 51.88 kcal/(mol*rad$^{-2}$), $\theta_0$ = 116.03 |
| | | CA-CD-CD | k = 63.68 kcal/(mol*rad$^{-2}$), $\theta_0$ = 127.52 |
| | | CA-CD-HA | k = 46.96 kcal/(mol*rad$^{-2}$), $\theta_0$ = 115.13 |
| | | C-CT-NT | k = 66.32 kcal/(mol*rad$^{-2}$), $\theta_0$ = 111.14 |
| | | CA-CT-H1 | k = 46.99 kcal/(mol*rad$^{-2}$), $\theta_0$ = 109.56 |
| | | CA-CT-NT | k = 66.22 kcal/(mol*rad$^{-2}$), $\theta_0$ = 112.16 |
| | | C-N-CA | k = 63.82 kcal/(mol*rad$^{-2}$), $\theta_0$ = 123.71 |
| | | CT-C-N | k = 66.79 kcal/(mol*rad$^{-2}$), $\theta_0$ = 115.18 |
| | | N-C-OH | k = 74.29 kcal/(mol*rad$^{-2}$), $\theta_0$ = 112.82 |
| | | CA-NC-CA | k = 68.35 kcal/(mol*rad$^{-2}$), $\theta_0$ = 117.22 |
| | Dihedral | CA-CA-CD-CD | v = 26.6 kcal/(mol*rad$^{-2}$), phase = 180.0, period = 2 |
| | | CA-CA-CD-HA | v = 26.6 kcal/(mol*rad$^{-2}$), phase = 180.0, period = 2 |
| | | CA-N-C-OH | v = 10.0 kcal/(mol*rad$^{-2}$), phase = 180.0, period = 2 |
| | | CA-N-C-CT | v = 10.0 kcal/(mol*rad$^{-2}$), phase = 180.0, period = 2 |
| | | N-CA-CA-HA | v = 14.5 kcal/(mol*rad$^{-2}$), phase = 180.0, period = 2 |
| | | N-CA- | v = 14.5 kcal/(mol*rad$^{-2}$), phase = |

TABLE 3-continued

The modified AMBER force field parameters for zinc-free $ZRL_5$ residues.

| Non-standard residues | Type | Item | Parameters |
|---|---|---|---|
| | | CA-CA | 180.0, period = 2 |
| | | N-C-OH-HO | v = 4.60 kcal/(mol*rad$^{-2}$), phase = 180.0, period = 2 |
| | | N-C-CT-H1 | v = 0.00 kcal/(mol*rad$^{-2}$), phase = 180.0, period = 2 |
| | | N-C-CT-NT | v = 0.00 kcal/(mol*rad$^{-2}$), phase = 180.0, period = 2 |
| | | CA-CA-N-C | v = 1.80 kcal/(mol*rad$^{-2}$), phase = 180.0, period = 2 |

TABLE 4

The modified AMBER force field parameters for $Zn^{2+}$—$ZRL_5$ residues.

| Non-standard residues | Type | Item | Parameters |
|---|---|---|---|
| $Zn^{2+}$—$ZRL_5$ | Bonded | NE-ZN | k = 640.0 kcal/(mol*Å$^2$), d$_0$ = 2.048 Å |
| | | NF-ZN | k = 640.0 kcal/(mol*Å$^2$), d$_0$ = 2.201 Å |
| | | NG-ZN | k = 640.0 kcal/(mol*Å$^2$), d$_0$ = 2.049 Å |
| | Angle | CA-C-N | k = 70.790 kcal/(mol*rad$^{-2}$), θ$_0$ = 115.08 |
| | | CA-NE-ZN | k = 50.0 kcal/(mol*rad$^{-2}$), θ$_0$ = 121.90 |
| | | CM-NE-ZN | k = 50.0 kcal/(mol*rad$^{-2}$), θ$_0$ = 114.0 |
| | | NE-ZN-NF | k = 50.0 kcal/(mol*rad$^{-2}$), θ$_0$ = 81.2 |
| | | NE-ZN-NG | k = 50.0 kcal/(mol*rad$^{-2}$), θ$_0$ = 118.0 |
| | | CT-NF-ZN | k = 50.0 kcal/(mol*rad$^{-2}$), θ$_0$ = 105.0 |
| | | NF-ZN-NG | k = 50.0 kcal/(mol*rad$^{-2}$), θ$_0$ = 81.30 |
| | | CA-NG-ZN | k = 50.0 kcal/(mol*rad$^{-2}$), θ$_0$ = 120.0 |
| | | NG-ZN-NG | k = 50.0 kcal/(mol*rad$^{-2}$), θ$_0$ = 117.40 |
| | Dihedral | X-NE-ZN-X | v = 0.00 kcal/(mol*rad$^{-2}$), phase = 0.0, period = 2 |
| | | X-ZN-NT-X | v = 0.00 kcal/(mol*rad$^{-2}$), phase = 0.0, period = 2 |
| | | X-ZN-NC-X | v = 0.00 kcal/(mol*rad$^{-2}$), phase = 0.0, period = 2 |
| | | X-CA-NE-X | v = 0.00 kcal/(mol*rad$^{-2}$), phase = 0.0, period = 2 |
| | | X-NE-ZN-X | v = 0.00 kcal/(mol*rad$^{-2}$), phase = 0.0, period = 2 |
| | | X-NE-CA-X | v = 0.00 kcal/(mol*rad$^{-2}$), phase = 0.0, period = 2 |
| | | X-CM-NE-X | v = 0.00 kcal/(mol*rad$^{-2}$), phase = 0.0, period = 2 |
| | | X-NC-ZN-X | v = 0.00 kcal/(mol*rad$^{-2}$), phase = 0.0, period = 2 |
| | | X-ZN-NF-X | v = 0.00 kcal/(mol*rad$^{-2}$), phase = 0.0, period = 2 |
| | | X-NF-ZN-X | v = 0.00 kcal/(mol*rad$^{-2}$), phase = 0.0, period = 2 |
| | | X-ZN-NG-X | v = 0.00 kcal/(mol*rad$^{-2}$), phase = 0.0, period = 2 |
| | | X-CA-NG-X | v = 0.00 kcal/(mol*rad$^{-2}$), phase = 0.0, period = 2 |

TABLE 4-continued

The modified AMBER force field parameters for $Zn^{2+}$—$ZRL_5$ residues.

| Non-standard residues | Type | Item | Parameters |
|---|---|---|---|
| | | X-CT-NF-X | v = 0.00 kcal/(mol*rad$^{-2}$), phase = 0.0, period = 2 |
| | | X-NG-ZN-X | v = 0.00 kcal/(mol*rad$^{-2}$), phase = 0.0, period = 2 |
| | | X-CT-NF-X | v = 0.00 kcal/(mol*rad$^{-2}$), phase = 0.0, period = 2 |

Modeling and Simulations of $ZRL_5P_4$-EBNA1 and $Zn^{2+}$-$ZRL_5P_4$-EBNA1 Complex.

The initial structure of $ZRL_5P_4$-EBNA1 (denoted as L5P4-EBNA1 in the FIG. 10, 11, 14 and $Zn^{2+}$-$ZRL_5P_4$-EBNA1 (denoted as $Zn^{2+}$-L5P4-EBNA1 in the FIG. 12, 13, 14 complex was built based on the $P_4$-EBNA1 complex structure and putative $Zn^{2+}$-$ZRL_5$ structure, with CAhx linking the $ZRL_5P_4$/$Zn^{2+}$-$ZRL_5P_4$ to $P_4$. It was then arranged for the 200 ns, all atoms unbiased MD simulations in AMBER 14 with ff99SBildn force field. System preparation and simulation procedures were the same as the previous work. Briefly, the periodic boundary, cubic, TIP3 explicit water box with a 20 Å buffer was employed with neutralized charge by adding Cl$^-$. The system was then minimized and equilibrated by sander following three stages: (1) heated from 100 K to 300 K in 20 ps; (2) adjusting solvent density to 1 g/mL in 20 ps; and (3) equilibrated in 200 ps with NPT ensemble. A subsequent 100 ns NPT simulation was carried out with CUDA-accelerated PMEMD. A 2 fs time step and SHAKE-enabled setting were used for all equilibration and production stages. Berendsen thermostat was adopted for temperature control for all stages.

Post-Simulation Analysis.

10 conformational clusters of $P_4$-EBNA1 DBD complex were calculated via cpptraj by using default settings with distance defined by main chain atoms root-mean-square deviation (RMSD). The representative conformation of most abundant cluster (cluster 0) was saved for $P_4$-EBNA1 DBD interaction analysis. The binding free energies for whole production trajectory were calculated by MMPBSA. The time intervals were adjusted to make sure 200 frames were included in the calculation. The mbondi2 was used and the salt concentration was set to 0.1 M in Generalized Born (GB) calculation; the radii from the prmtop file was used and the ion strength was set to 0.1 mM for Poisson-Boltzman (PB) calculation.

INDUSTRIAL APPLICABILITY

The present disclosure is in the field of pharmaceuticals and chemical industries. More particularly, the present disclosure relates to zinc binding EBNA1-specific compounds with responsive imaging and inhibition of EBNA1 for the treatment of EBV-positive cells, such as cancer.

What we claim:

1. A compound of Formula I:

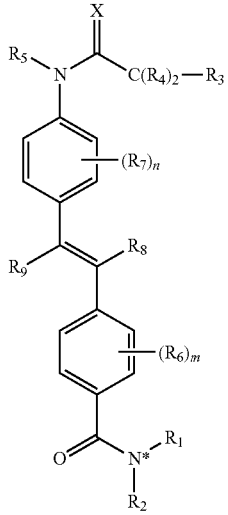

I or a pharmaceutically acceptable salt thereof, wherein m is a whole number selected from 0-4;

n is a whole number selected from 0-4;

p is a whole number selected from 0-4;

X is $H_2$, S, or O;

each instance of R is independently H or alkyl;

$R_1$ is a polypeptide selected from the group consisting of SEQ ID NO:1, SEQ ID NO:2, SEQ ID NO:3, SEQ ID NO:4, SEQ ID NO:5, and SEQ ID NO:6, wherein N* represents the N-terminal nitrogen of the polypeptide;

$R_2$ is H or alkyl;

$R_3$ is selected from the group consisting of:

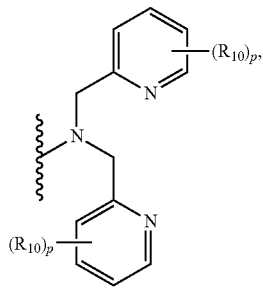

-continued

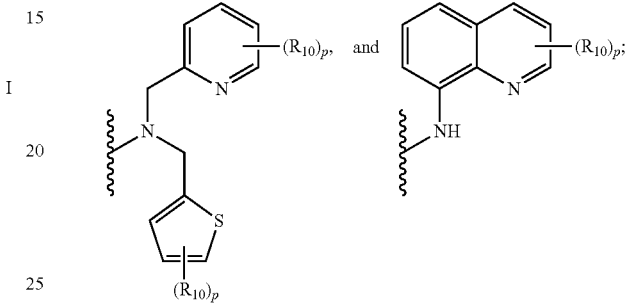

each instance of $R_4$ is independently H or alkyl;

$R_5$ is H or alkyl;

each instance of $R_6$ is independently alkene, alkyne, cycloalkyl, aryl, heteroaryl, halide, nitrile, nitro, OR, or $NR_2$;

each instance of $R_7$ is independently alkene, alkyne, cycloalkyl, aryl, heteroaryl, halide, nitrile, nitro, OR, or $NR_2$;

each of $R_8$ and $R_9$ is independently H or alkyl; and each instance of $R_{10}$ is independently alkene, alkyne, cycloalkyl, aryl, heteroaryl, halide, nitrile, nitro, OR, or $NR_2$.

2. The compound of claim 1, wherein each of $R_6$, $R_7$, and $R_{10}$ for each occurrence is independently selected from the group consisting of alkyl halide, nitrile, and nitro.

3. The compound of claim 1, wherein each of $R_2$ and $R_5$ is H.

4. The compound of claim 1, wherein each of $R_4$, $R_8$, and $R_9$ is H.

5. The compound of claim 1, wherein X is O and $R_3$ is:

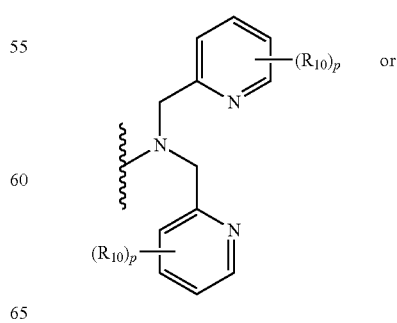

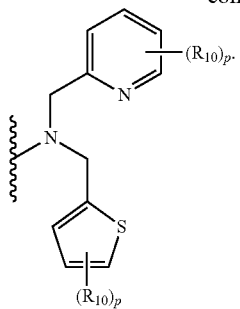

6. The compound of claim 5, wherein $R_6$, $R_7$, and $R_{10}$ for each occurrence is independently selected from the group consisting of alkyl, halide, nitrile, and nitro.

7. The compound of claim 6, wherein each of $R_4$, $R_8$, and $R_9$ is H.

8. The compound of claim 1, wherein the compound has Formula II:

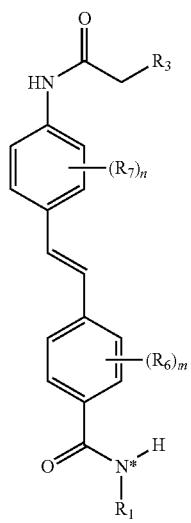

II or a pharmaceutically acceptable salt thereof, wherein
m is a whole number selected from 0-4;
n is a whole number selected from 0-4;
p is a whole number selected from 0-4;
$R_1$ is a polypeptide selected from the group consisting of SEQ ID NO:1, SEQ ID NO:2, SEQ ID NO:3, SEQ ID NO:4, SEQ ID NO:5, and SEQ ID NO:6, wherein N* represents the N-terminal nitrogen of the polypeptide;
$R_3$ is selected from the group consisting of:

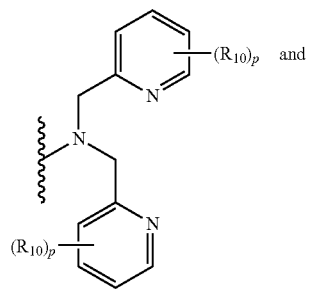

and

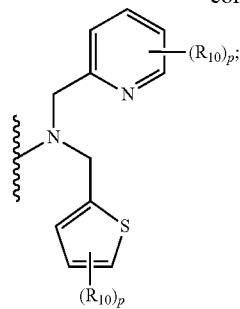

each instance of $R_6$ is independently alkyl, alkene, alkyne, cycloalkyl, aryl, heteroaryl, halide, nitrile, nitro, OR, or $NR_2$;

each instance of $R_7$ is independently alkyl, alkene, alkyne, cycloalkyl, aryl, heteroaryl, halide, nitrile, nitro, OR, or $NR_2$;

each of $R_8$ and $R_9$ is independently H or alkyl; and each instance of $R_{10}$ is independently alkyl, alkene, alkyne, cycloalkyl, aryl, heteroaryl, halide, nitrile, nitro, OR, or $NR_2$.

9. The compound of claim 1, wherein the compound has the Formula III:

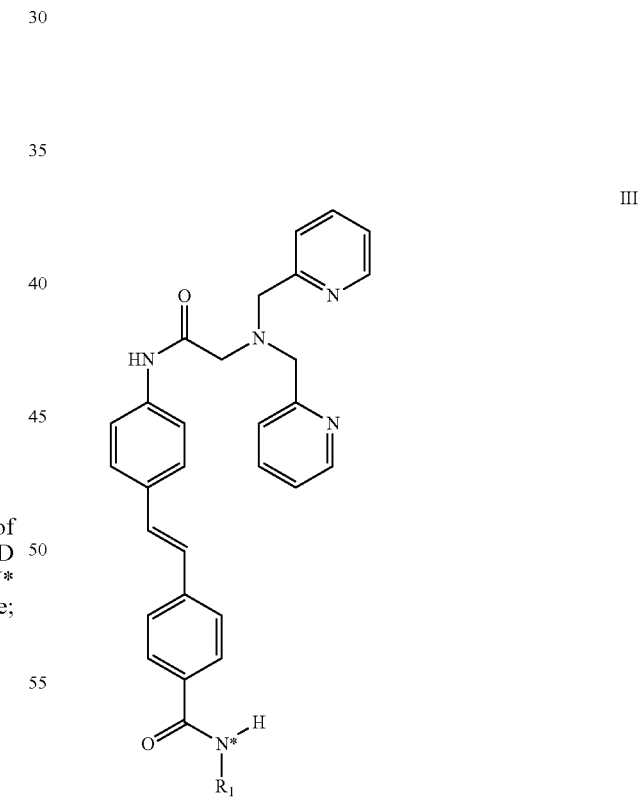

III or a pharmaceutically acceptable salt thereof, wherein
$R_1$ is a polypeptide selected from the group consisting of SEQ ID NO:1, SEQ ID NO:2, SEQ ID NO:3, SEQ ID NO:4, SEQ ID NO:5, and SEQ ID NO:6, and wherein N* represents the N-terminal nitrogen of the polypeptide.

10. The compound of claim 1, wherein X is H2 and R3 is:

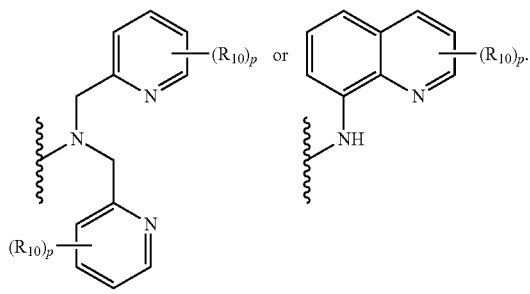

11. The compound of claim 10, wherein each of $R_6$, $R_7$, and $R_{10}$, for each occurrence is independently selected from the group consisting of alkyl, halide, nitrile, and nitro.

12. The compound of claim 11, wherein each of $R_2$ and $R_5$ is H.

13. The compound of claim 12, wherein each of $R_4$, $R_8$, and $R_9$ is H.

14. The compound of claim 13, wherein each of m, n, and p is 0.

15. A method of treating an Epstein-Barr virus (EBV)-positive cell in a patient in need thereof comprising administering a therapeutically effective amount of a compound of claim 1 to the patient.

16. The method of claim 15, wherein the EBV-postive cell is a cancerous cell.

17. The method of claim 16, wherein the cancerous cell is Burkitt's lymphoma, non-Hodgkin's lymphoma, Hodgkin's disease, T-cell lymphoma, B-cell lymphoma, transplant-associated lymphoproliferative disorders, nasopharyngeal carcinoma, gastric adenocarcinoma, parotid carcinoma, or leiomyosarcoma.

18. The method of claim 14, wherein the compound as the Formula III:

or a pharmaceutically acceptable salt thereof, wherein $R_1$ is a polypeptide selected from the group consisting of SEQ ID NO:1, SEQ ID NO:2, SEQ ID NO:3, SEQ ID NO:4, SEQ ID NO:5, and SEQ ID NO:6, and wherein N* represents the N-terminal nitrogen of the polypeptide.

19. A method of imaging an EBV-positive cell comprising the step of contacting the EBV-positive cell with a compound of claim 1 and measuring the fluorescence of the compound.

20. The method of claim 19, wherein the compound has the Formula III:

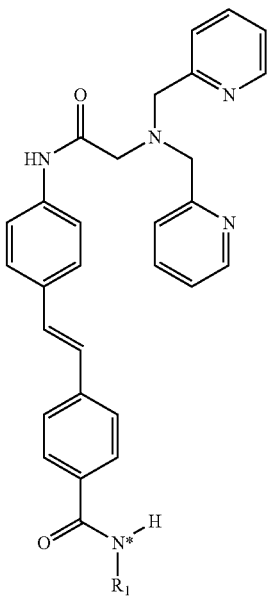

or a pharmaceutically acceptable salt thereof, wherein $R_1$ is a polypeptide selected from the group consisting of SEQ ID NO: 1, SEQ ID NO: 2, SEQ ID NO:3, SEQ ID NO:4, SEQ ID NO:5, and SEQ ID NO:6, and wherein N* represents the N-terminal nitrogen of the poly peptide.

* * * * *

SEQUENCE LISTING

<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide prepared in the lab.

<400> SEQUENCE: 1

Cys Tyr Phe Met Val Phe
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide prepared in the lab.

<400> SEQUENCE: 2

Tyr Phe Met Val Phe
1               5

<210> SEQ ID NO 3
<211> LENGTH: 13
<212> TYPE: PRT
<213> ORGANISM: Artificial Sequence
<220> FEATURE:
<223> OTHER INFORMATION: Synthetic peptide prepared in the lab.
<220> FEATURE:
<221> NAME/KEY: Xaa is 6-Aminocaproic acid
<222> LOCATION: (2)..(2)
<220> FEATURE:
<221> NAME/KEY: Xaa is D-arginine
<222> LOCATION: (4)..(4)
<223> OTHER INFORMATION: Xaa is D-arginine

<400> SEQUENCE: 3

Cys Xaa Arg Xaa Arg Lys Gly Gly Tyr Phe Met Val Phe
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic peptide prepared in the lab.
<220> FEATURE:
<221> NAME/KEY: Xaa is 6-aminohexanoic acid
<222> LOCATION: (2)..(2)
<220> FEATURE:
<221> NAME/KEY: Xaa is D-arginine
<222> LOCATION: (11)..(11)

<400> SEQUENCE: 4

Cys Xaa Tyr Phe Met Val Phe Gly Gly Arg Xaa Arg Lys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide prepared in the lab.
<220> FEATURE:
<221> NAME/KEY: Xaa is 6-aminohexanoic acid
<222> LOCATION: (1)..(1)
<220> FEATURE:
<221> NAME/KEY: Xaa is D-arginine
<222> LOCATION: (10)..(10)

<400> SEQUENCE: 5

Xaa Tyr Phe Ile Val Phe Gly Gly Arg Xaa Arg Lys
1               5                   10

<210> SEQ ID NO 6

```
<211> LENGTH: 5
<212> TYPE: PRT
<213> ORGANISM: Artificial Sequence
<220> FEATURE:
<223> OTHER INFORMATION: Synthetic peptide prepared in the lab.

<400> SEQUENCE: 6

Tyr Phe Ile Val Phe
1               5
```